(12) United States Patent
Bauer et al.

(10) Patent No.: US 6,413,509 B1
(45) Date of Patent: *Jul. 2, 2002

(54) METHODS OF EX-VIVO EXPANSION OF HEMATOPOIETIC CELLS USING INTERLEUKIN-3 MUTANT POLYPEPTIDES WITH OTHER HEMATOPOIETIC GROWTH FACTORS

(76) Inventors: S. Christopher Bauer, 4656 Orchard Rd., New Haven, MO (US) 63068; Mark Allen Abrams, 7723 Blackberry Ave., St. Louis, MO (US) 63130; Sarah Ruth Braford-Goldberg, 4111 W. Pine #10, St. Louis, MO (US) 63108; Maire Helena Caparon, 109 Beechwood Ct., Chesterfield, MO (US) 63017; Alan Michael Easton, 2317 Seven Pines Dr. #7, Maryland Heights, MO (US) 63146; Barbara Kure Klein, 12917 Topping Estates, St. Louis, MO (US) 63131; John P. McKearn, 18612 Babler Meadows Dr., Glencoe, MO (US) 63038; Peter O. Olins, 10625 Goose Haven, Lafayette, CO (US) 80026; Kumnan Paik, 636 Illinois Rd., Wilmette, IL (US) 60091; John Thomas, 13426 Mason Valley Ct., Town & Country, MO (US) 63131

( * ) Notice: Subject to any disclaimer, the term of this patent is extended or adjusted under 35 U.S.C. 154(b) by 0 days.

This patent is subject to a terminal disclaimer.

(21) Appl. No.: 08/761,907

(22) Filed: Dec. 9, 1996

Related U.S. Application Data

(63) Continuation-in-part of application No. 08/446,871, filed as application No. PCT/US95/01184 on Feb. 4, 1995, which is a continuation-in-part of application No. 08/193,373, filed on Feb. 4, 1994, now Pat. No. 6,153,183, which is a continuation-in-part of application No. 08/411,795, filed as application No. PCT/US93/11197 on Nov. 22, 1993, now Pat. No. 5,604,116, which is a continuation-in-part of application No. 07/981,044, filed on Nov. 24, 1992, now abandoned.

(51) Int. Cl.[7] .................. A61K 45/00; A61K 38/21; C12N 5/08

(52) U.S. Cl. .................. 424/85.1; 424/85.2; 424/85.4; 435/372

(58) Field of Search .................. 424/85.4, 85.1, 424/85.2, 93.21, 93.71; 435/372, 372.3

(56) References Cited

U.S. PATENT DOCUMENTS 4,438,032 A  3/1984  Golde et al.

(List continued on next page.)

FOREIGN PATENT DOCUMENTS

EP  EP 018 3350  6/1986

(List continued on next page.)

OTHER PUBLICATIONS

Haylock, D.N., et al. (1992) *Blood* 80(6): 1405–12.*

(List continued on next page.)

*Primary Examiner*—Gary L. Kunz
*Assistant Examiner*—Robert S. Landsman
(74) *Attorney, Agent, or Firm*—Dennis A. Bennett; S. Christopher Bauer

(57) ABSTRACT

The present invention relates to methods of ex-vivo expansion of hematopoietic cells by culturing hematopoietic cells in a growth medium comprising a variant of human interleukin-3 (hIL-3), which contains multiple amino acid substitutions and which may have portions of the native hIL-3 molecule deleted, and a hematopoietic growth factor. The present invention also relates to the ex-vivo expansion of hematopoietic cells for gene therapy. Additionally, the present invention relates to the use of the expanded hematopoietic cells for treating patients having a hematopoietic disorder.

35 Claims, 4 Drawing Sheets

```
    1              5                    10
ATG GCT CCA ATG ACT CAG ACT ACT TCT CTT AAG ACT TCT
Met Ala Pro Met Thr Gln Thr Thr Ser Leu Lys Thr Ser
              15                  20              25
TGG GTT AAC TGC TCT AAC ATG ATC GAT GAA ATT ATA ACA
Trp Val Asn Cys Ser Asn Met Ile Asp Glu Ile Ile Thr
                       30                  35
CAC TTA AAG CAG CCA CCT TTG CCT TTG CTG GAC TTC AAC
His Leu Lys Gln Pro Pro Leu Pro Leu Leu Asp Phe Asn
         40                  45              50
AAC CTC AAT GGG GAA GAC CAA GAC ATT CTG ATG GAA AAT
Asn Leu Asn Gly Glu Asp Gln Asp Ile Leu Met Glu Asn
              55                  60
AAC CTT CGA AGG CCA AAC CTG GAG GCA TTC AAC AGG GCT
Asn Leu Arg Arg Pro Asn Leu Glu Ala Phe Asn Arg Ala
65                 70                  75
GTC AAG AGT TTA CAG AAT GCA TCA GCA ATT GAG AGC ATT
Val Lys Ser Leu Gln Asn Ala Ser Ala Ile Glu Ser Ile
              80                  85              90
CTT AAA AAT CTC CTG CCA TGT CTG CCC CTG GCC ACG GCC
Leu Lys Asn Leu Leu Pro Cys Leu Pro Leu Ala Thr Ala
                       95                  100
GCA CCC ACG CGA CAT CCA ATC CAT ATC AAG GAC GGT GAC
Ala Pro Thr Arg His Pro Ile His Ile Lys Asp Gly Asp
         105                110                 115
TGG AAT GAA TTC CGT CGT AAA CTG ACC TTC TAT CTG AAA
Trp Asn Glu Phe Arg Arg Lys Leu Thr Phe Tyr Leu Lys
              120                 125
ACC TTG GAG AAC GCG CAG GCT CAA CAG ACC ACT CTG TCG
Thr Leu Glu Asn Ala Gln Ala Gln Gln Thr Thr Leu Ser
130
CTA GCG ATC TTT TAA TAA    (SEQ ID NO:144)
Leu Ala Ile Phe END END    (SEQ ID NO:128)
```

U.S. PATENT DOCUMENTS

| | | | |
|---|---|---|---|
| 4,810,643 A | | 3/1989 | Souza |
| 4,877,729 A | | 10/1989 | Clark et al. |
| 4,959,455 A | * | 9/1990 | Clark .................. 530/351 |
| 4,999,291 A | | 3/1991 | Souza |
| 5,032,395 A | | 7/1991 | Clark et al. |
| 5,073,627 A | | 12/1991 | Curtis et al. |
| 5,199,942 A | * | 4/1993 | Gillis ....................... 604/4 |
| 5,218,092 A | | 6/1993 | Sasaki et al. |
| 5,516,512 A | * | 5/1996 | Dorssers et al. ........ 424/85.2 |
| 5,591,427 A | * | 1/1997 | Vadas et al. ............ 424/85.2 |
| 5,604,116 A | * | 2/1997 | Bauer et al. .......... 435/69.52 |

FOREIGN PATENT DOCUMENTS

| | | |
|---|---|---|
| EP | EP 03 37359 | 10/1989 |
| EP | EP 413 383 A1 | 2/1991 |
| JP | 4-63595 * | 2/1992 |
| WO | WO 90/01039 | 2/1990 |
| WO | WO 90/12877 | 11/1990 |
| WO | WO 88/05469 | 3/1991 |
| WO | WO 92/04455 | 3/1992 |
| WO | WO 92/06166 | 4/1992 |
| WO | WO 93/07171 | 4/1993 |

OTHER PUBLICATIONS

Brenner, M.K., et al. (1995) *Cytokines Mol. Ther.* 1: 3–9.*
Dorssers, L., et al. (1991) *J. Biol. Chem.* 266: 21310–17.*
Kaushansky, K., et al. (1992) *J. Clin. Invest.* 90: 1879–88.*
Aglietta, M., et al., Stem Cells Dayt 2 (83): 83–7 (1993).
Applebaum, F.R., Cancer, 72 (11 Suppl): 3387–92 (1993).
Bodine, D.M. et al., Blood 78 (4): 914–20 (1991).
Brandt, J., et al., Blood 79 (3): 634–641 (1992).
Brandt, J.E., et al., Blood 83 (6): 1507–1514 (1994).
Briddell, R.A., et al., Blood 76 (3): 516–522 (1990).
Broxmeyer, H.E., et al., J.Immun 141: 3852–3862 (1988).
Broxmeyer, H.E., et al., Blood 77 (10): 2142–2149 (1991).
Brugger, W., et al., Blood 81 (10): 2679–2584 (1993).
Bruno, E., et al., Blood 73 (3): 671–677 (1989).
Bruno E., et al., Blood 77 (11): 2339–2346.
Donahue, R.E., et al., Science 241: 1820–1823 (1988).
Donahue, R.E. et al., Annals N.Y. Acad. Of Sci 51: 10–16 (1987).
Emerson, S.G., et al., J. Clin. Invest. 82: 1282–1287 (1988).
Farese, A.M., et al., Blood 82 (10): 3012–3018 (1993).
Ganser, A., et al., Blood 79 (10): 2583–2591 (1992).
Gordon, M.S., et al., Blood 80 (2): 302–307 (1992).
Grosh, W.W. et al., Clin Immunol Immunopathol 62 (1 Pt 2): s25–38 (1992).
Heyworht, C.M., et al., Growht Factors 2 (2–3): 197–211 (1990).
Iscova, N.N., et al., J. Immun 142: 2332–2337 (1989).
Ikebuchi, K., et al., Proc. Natl. Acad. Sci. USA 84: 9035–9039 (1987).
Jacobsen, S.E.W. et al., Blood 80 (3): 678–687 (1992).
Jacobsen, F.W., et al., Blood 84 (3): 775–779 (1994).
Jacobsen, S.E.W., et al., J. Exp. Med. 181:1357–1363 (1995).
Kaushansky, K., et a., Proc. Natl. Acad. Sci. USA 92: 3234–3238 (1995).
Kawano, Y., et al., Blood 77 (10): 2118–2121 (1991).
Kawano, Y., et al., Stem Cells 12: 514–520 (1994).
Krumwieh, D. et al., Int J. Cell Cloning 1 (229): 229–47 (1990).
Lopez, A.F., et al., Proc. Natl. Acad. Sci. USA 89: 11842–11846 (1992).
Mayani, H., et al., Blood 81 (12): 3252–3258 (1993).
MacVittie, T.J., et al., Blood 84 (8): 2515–2522 (1994).
Metcalf, D. et al., Blood 79 (11): 2861–2866 (1992).
Metcalf, D. Stem Cells Dayt 2 (1): 1–11 (1993).
Metcalf, D. Blood 82 (12): 3515–3523 (1993).
Moore, M.A. Cancer 65 (3 Suppl): 836–44 (1990).
Moore, M.A. Blood 78 (1): 1–19 (1991).
Nand, S., et al., Blood 83 (2): 357–360 (1994).
Neidhart, J.A. Cancer Supplement 72 (11): 3381–3386 (1993).
Ogawa, M. Blood 81 (11): 2844–53 (1993).
Pietsch, T., et al., Blood 80 (5): 1199–206 (1992).
Ploemacher, R.E., et al., Leukemia 7 (9): 1381–1388 (1993).
Rennick, D., et al., Expermintal Hematology 22: 136–141 (1994).
Robinson, B.E., et al., J. Clin. Invest. 79:1648–1652 (1987).
Sekhsaria, S. et al., Blood 81 (8): 2152–2130 (1993).
Sieff, C.A., et al., Blood 73 (3): 688–693 (1989).
Smith, S.L., et al., Exp. Hem. 21 (7): 870–7 (1993).
Sonoda, Y., et al., Proc. Natl. Acd. Sci. USA 85:4360–4364 (1988).
Stahl, C.P., et al., Blood 80(10): 1479–2485 (1992).
Sutherland, H.J., et al., Blood 81 (6): 1465–1470 (1993).
Takaue, Y., et al., Blood 76 (2): 330–5 (1990).
Tsuji, K., et al., Blood 79 (11): 2855–60 (1992).
Warren, D.J., et al., J. of Immunology 140: 94–99 (1988).

* cited by examiner

FIG. 1

```
      1                         5                          10
ATG   GCT   CCA   ATG   ACT   CAG   ACT   ACT   TCT   CTT   AAG   ACT   TCT
Met   Ala   Pro   Met   Thr   Gln   Thr   Thr   Ser   Leu   Lys   Thr   Ser
                  15                         20                         25
TGG   GTT   AAC   TGC   TCT   AAC   ATG   ATC   GAT   GAA   ATT   ATA   ACA
Trp   Val   Asn   Cys   Ser   Asn   Met   Ile   Asp   Glu   Ile   Ile   Thr
                        30                         35
CAC   TTA   AAG   CAG   CCA   CCT   TTG   CCT   TTG   CTG   GAC   TTC   AAC
His   Leu   Lys   Gln   Pro   Pro   Leu   Pro   Leu   Leu   Asp   Phe   Asn
      40                         45                         50
AAC   CTC   AAT   GGG   GAA   GAC   CAA   GAC   ATT   CTG   ATG   GAA   AAT
Asn   Leu   Asn   Gly   Glu   Asp   Gln   Asp   Ile   Leu   Met   Glu   Asn
                              55                         60
AAC   CTT   CGA   AGG   CCA   AAC   CTG   GAG   GCA   TTC   AAC   AGG   GCT
Asn   Leu   Arg   Arg   Pro   Asn   Leu   Glu   Ala   Phe   Asn   Arg   Ala
65                                  70                         75
GTC   AAG   AGT   TTA   CAG   AAT   GCA   TCA   GCA   ATT   GAG   AGC   ATT
Val   Lys   Ser   Leu   Gln   Asn   Ala   Ser   Ala   Ile   Glu   Ser   Ile
                  80                         85                         90
CTT   AAA   AAT   CTC   CTG   CCA   TGT   CTG   CCC   CTG   GCC   ACG   GCC
Leu   Lys   Asn   Leu   Leu   Pro   Cys   Leu   Pro   Leu   Ala   Thr   Ala
                              95                         100
GCA   CCC   ACG   CGA   CAT   CCA   ATC   CAT   ATC   AAG   GAC   GGT   GAC
Ala   Pro   Thr   Arg   His   Pro   Ile   His   Ile   Lys   Asp   Gly   Asp
            105                        110                        115
TGG   AAT   GAA   TTC   CGT   CGT   AAA   CTG   ACC   TTC   TAT   CTG   AAA
Trp   Asn   Glu   Phe   Arg   Arg   Lys   Leu   Thr   Phe   Tyr   Leu   Lys
                        120                        125
ACC   TTG   GAG   AAC   GCG   CAG   GCT   CAA   CAG   ACC   ACT   CTG   TCG
Thr   Leu   Glu   Asn   Ala   Gln   Ala   Gln   Gln   Thr   Thr   Leu   Ser
130
CTA   GCG   ATC   TTT   TAA   TAA         (SEQ ID NO:144)
Leu   Ala   Ile   Phe   END   END         (SEQ ID NO:128)
```

METHODS OF EX-VIVO EXPANSION OF HEMATOPOIETIC CELLS USING INTERLEUKIN-3 MUTANT POLYPEPTIDES WITH OTHER HEMATOPOIETIC GROWTH FACTORS

This is a continuation-in-part of U.S. Ser. No. 08/446,871, filed Jun. 06, 1995; which was filed as international application PCT/US95/01184 on Feb. 4, 1995 and which entered the U.S. national stage under 35 U.S.C. § 371 on Jun. 6, 1995; which in turn, is a continuation-in-part of U.S. Ser. No. 08/193,373, filed Feb. 4, 1994, now U.S. Pat. No. 6,153,183; which is a continuation-in-part of U.S. Ser. No. 08/411,795, filed Apr. 6, 1995, now U.S. Pat. No. 5,604,116; which was filed as international application PCT/US93/11197 on Nov. 22, 1993, and which entered the U.S. national stage under 35 U.S.C § 371 on Apr. 6, 1995; which, in turn, is a continuation-in-part of U.S. Ser. No. 07/981,044, filed Nov. 24, 1992, which is now abandoned. The noted applications are incorporated herein by reference.

FIELD OF THE INVENTION

The present invention relates to methods of ex-vivo expansion of hematopoietic cells by culturing hematopoietic cells in a growth medium comprising a variant of human interleukin-3 (hIL-3) and another colony stimulating factors, cytokines, lymphokines, interleukins, hematopoietic growth factors or IL-3 variants and uses for the expanded cells for treating patients having a hematopoietic disorders.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies (when erythropoietin is added).

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and/or chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., *CELL* 47:3, 1986).

Murine IL-3 (mIL-3) was first identified by Ihle, et al., (*J. IMMUNOL.* 126:2184, 1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., *NATURE* 307:233, 1984) and Yokota, et al., *PROC. NATL. ACAD. SCI. USA* 81:1070, 1984). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., (*CELL* 47:3, 1986). The human sequence reported by Yang, et al., included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., (*GENE* 55:115, 1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,455 disclose human IL-3 and gibbon IL-3 cDNAs and the protein sequences for which they code. The hIL-3 disclosed has serine rather than proline at position 8 in the protein sequence.

Clark-Lewis, et al., *SCIENCE* 231:134 (1986) performed a functional analysis of murine IL-3 analogs synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140} \rightarrow Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., *PROC. NATL. ACAD. SCI. USA* 85:7897, 1988).

International Patent Application (PCT) WO 88/00598 discloses gibbon- and human-like IL-3. The hIL-3 contains a $Ser^8 \rightarrow Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1 \rightarrow Asp^1$, $Trp^{13} \rightarrow Arg^{13}$ (pGB/IL-302) and $Ala^1 \rightarrow Asp^1$, $Met^3 \rightarrow Thr^3$ (pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in *Saccharomyces cerevisiae* by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are $Met^2 \rightarrow Ile^2$ and $Ile^{131} \rightarrow Leu^{131}$. It is not disclosed whether the contemplated neutralities were obtained for these two mutations.

WO 91/00350 discloses nonglycosylated hIL-3 analog proteins, for example, hIL-3 ($Pro^8Asp^{15}Asp^{70}$), $Met^3$ rhuIL-3 ($Pro^8Asp^{15}Asp^{70}$); $Thr^4$ rhuIL-3 ($Pro^8Asp^{15}Asp^{70}$) and $Thr^6$ rhuIL-3 ($Pro^8Asp^{15}Asp^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at $Met^3$, $Thr^4$, or $Thr^6$.

WO 90/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/07988 discloses a method to increase megakaryocyte production comprised of administration of G-CSF with IL-3 or GM-CSF. Also disclosed is a method for increasing platelet production comprised of administration of IL-6 with IL-3, G-CSF or GM-CSF.

Hematopoietic growth factors, such as hIL-3, have been administered alone, co-administered with other hematopoietic growth factors, or in combination with bone marrow transplants subsequent to high dose chemotherapy to treat the neutropenia and thrombocytopenia which are often the result of such treatment. However the period of severe neutropenia and thrombocytopenia may not be totally eliminated. The myeloid lineage, which is comprised of monocytes (macrophages), granulocytes (including neutrophils) and megakaryocytes, is critical in preventing infections and bleeding which can be life-threatening. Neutropenia and thrombocytopenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow or other is limited, 2) Graft Versus Host Disease, 3) graft rejection and 4) possible contamination with tumor cells. Stem cells make up a very small percentage of the nucleated cells in the bone marrow, spleen and peripheral blood. It is clear that a dose response exits such that a greater number of stem cells will enhance hematopoietic recovery. Therefore, the ex-vivo expansion of stem cells should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogenic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells.

The limited number of stem cells may be overcome by ex-vivo expansion of the stem cells. In addition, stem cells can be specifically isolated selected based on the presence of specific surface antigen such as CD34+ in order to decrease tumor cell contamination of the marrow graft.

The following patents contain further details on separating stem cells, CD34+ cells, culturing the cells with hematopoietic factors, the use of the cells for the treatment of patients with hematopoietic disorders and the use of hematopoietic factors for cell expansion and gene therapy.

U.S. Pat. No. 5,061,620 relates to compositions comprising human hematopoietic stem cells provided by separating the stem cells from dedicated cells.

U.S. Pat. No. 5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM-CSF, IL-1, GM-CSF/IL-3 fusion protein and combinations thereof; (3) administering cellular preparation to a patient.

U.S. Pat. No. 5,240,856 relates to a cell separator that includes apparatus for automatically controlling the cell separation process.

U.S. Pat. No. 5,240,856 relates to a cell separator that includes apparatus for automatically controlling the cell separation process.

U.S. Pat. No. 5,409,813 describes methods of positive and negative selection of a cell population from a mixture of cell populations utilizing a magnetically stabilized fluidized bed.

U.S. Pat. No. 5,409,825 relates to a method of growing hematopoietic stem cells in a liquid culture medium using mast cell growth factor (MGF) and optionally at least one cytokine selected from the group consisting of IL-3, GM-CSF and IL-3/GM-CSF fusion protein.

U.S. Pat. No. 5,459,069 relates to devices for maintaining and growing human stem cells and/or hematopoietic cells in culture.

U.S. Pat. No. 5,541,103 describes peripheral blood progenitor cells obtained by enriching blood progenitors expressing the cd34 antigen and culture the cells in a growth medium consisting of IL-1, IL-3, IL-6, erythropoietin and stem cell growth factor.

U.S. Pat. No. 5,464,753 describes a method of purifying pluripotent hematopoietic stem cells expressing P-glycoprotein from a mixture of blood or bone marrow cells.

U.S. Pat. No. 5,547,687 relates to a method of enriching CD34 cells from a cell mixture by density centrifugation.

U.S. Pat. No. 5,571,686 depicts the use of megapoietin (c-mpl ligand) for the in vitro expansion of stem cells as a source of platelets for transplantation and for increasing the storage life of platelets.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from a mixed population of cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1α, IL-3, IL-6 or GM-CSF is discussed in Brandt et al., *J. Clin. Invest.* 86:932–941, 1990.

SUMMARY OF THE INVENTION

The present invention encompasses the use of recombinant human interleukin-3 (hIL-3) variant or mutant proteins (muteins) with other colony stimulating factors (CSFs), cytokines, lymphokines, interleukins, hematopoietic growth factors (herein after collectively referred to as "hematopoietic growth factors") for the ex-vivo expansion of hematopoietic cells. Ex-vivo expansion of hematopoietic cells and the transplanting of the these cells into a patient may have the potential for therapeutic use in restoring hematopoietic cells to normal amounts in those cases where the number of cells has been reduced due to diseases or to therapeutic treatments such as radiation and/or chemotherapy. Coadministration or sequential use of IL-3 variants of the present invention with other colony stimulating factors for ex-vivo expansion may enhance therapeutic value due to the synergistic effects of the proteins that make up the culture medium. Coadministration or sequential treatment may have the usual activity of the peptides forming the mixture or it may be further characterized by having a biological or physiological activity greater than simply the additive function of the presence of IL-3 or the other growth factors alone. Coadministration or sequential treatment may also unexpectedly provide an enhanced effect on the activity or an activity different from that expected by the presence of IL-3 or the other growth factors.

The present invention includes the use of variants of hIL-3 in which from 1 to 14 amino acids have been deleted from the N-terminus and/or from 1 to 15 amino acids have been deleted from the C-terminus, containing multiple amino acid substitutions, which are used with other growth factors or IL-3 variant for the ex-vivo expansion of hematopoietic cells. Preferred IL-3 variants of the present invention include variants in which amino acids 1 to 14 have been deleted from the N-terminus, amino acids 126 to 133 have been deleted from the C-terminus and contain from about four to about twenty-six amino acid substitutions in the polypeptide sequence.

The present invention is directed to methods for ex vivo expansion of stem cells, comprising the steps of;

(a) culturing said stem cells with a selected growth medium comprising a human interleukin-3 mutant polypeptide of (SEQ ID NO:1)

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to 44 of the amino acids designated by Xaa are different from the corresponding amino acids of native (1–133) human interleukin-3;wherein from 1 to 14 amino acids can be deleted from the N-terminus and/or from 1 to 15 amino acids can be deleted from the C-terminus; and said interleukin-3 mutant polypeptide can additionally be immediately preceded by Methionine$^{-1}$, Alanine$^{-1}$ or Methionine$^{-2}$ Alanine$^{-1}$; and a hematopoietic growth factor; and (b) harvesting said cultured stem cells.

Additionally, the present invention encompasses methods of ex-vivo expansion of stem cells comprising the steps of (a) separating stem cells from a mixed population of cells; (b) culturing said separated stem cells with a growth medium comprising a human interleukin-3 mutant polypeptide and one or more other hematopoietic growth factors; (c) harvesting said cultured cells.

The present invention includes methods for treatment of a patient having a hematopoietic disorder, comprising the steps of; (a) removing stem cells from said patient or a blood donor; (b) culturing said stem cells with a growth medium comprising a human interleukin-3 mutant polypeptide and one or more other hematopoietic growth factors; (c) harvesting said cultured cells; and (d) transplanting said cultured cells into said patient.

The present invention also includes methods for treatment of a patient having a hematopoietic disorder, comprising the steps of; (a) removing stem cells from said patient or a blood donor; (b) separating stem cells from a mixed population of cells; (c) culturing said separated stem cells with a growth medium comprising a human interleukin-3 mutant polypeptide and one or more other hematopoietic growth factors; (d) harvesting said cultured cells; and (e) transplanting said cultured cells into said patient.

It is also envisioned that a patient could be given a hematopoietic growth factor, preferably a early acting factor, prior to removing stem cells for ex-vivo expansion to increase the number of early progenitors. It is also envisioned that a portion of the stem cells removed from a patient could be frozen and transplanted with the expanded stem cells to provide more early progenitors.

It is envisioned that the present invention includes methods of human gene therapy, comprising the steps of; (a) removing stem cells from a patient or blood donor; (b) culturing said stem cells with a selected growth medium comprising a human interleukin-3 mutant polypeptide and one or more other hematopoietic growth factors; (c) introducing DNA into said cultured cells; (d) harvesting said transduced cells; and (e) transplanting said transduced cells into said patient.

It is also envisioned that the present invention includes methods of human gene therapy, comprising the steps of; (a) removing stem cells from a patient or blood donor; (b) separating said stem cells from a mixed population cells; (c) culturing said separated stem cells with a selected growth medium comprising a human interleukin-3 mutant polypeptide and one or more other hematopoietic growth factors; (d) introducing DNA into said cultured cells; (e) harvesting said transduced cells; and (f) transplanting said transduced cells into said patient.

The present invention also includes the cultured stem cells obtained by the selective ex vivo expansion of stem cells with a human interleukin-3 mutant polypeptide and one or more other hematopoietic growth factors. Additionally, transduced stem cells obtained from culturing stem cells with a human interleukin-3 mutant polypeptide and one or more other hematopoietic growth factors and transducing the cells with a DNA sequence encoding a desired gene product are included in the present invention.

BRIEF DESCRIPTION OF THE DRAWINGS

FIG. 1 is the human IL-3 gene for *E.coli* expression (pMON5873), encoding the polypeptide sequence of natural (wild type) human IL-3 [SEQ ID NO:128], plus an initiator methionine, as expressed in *E. coli*, with the amino acids numbered from the N-terminus of the natural hIL-3.

DETAILED DESCRIPTION OF THE INVENTION

Figure 2:
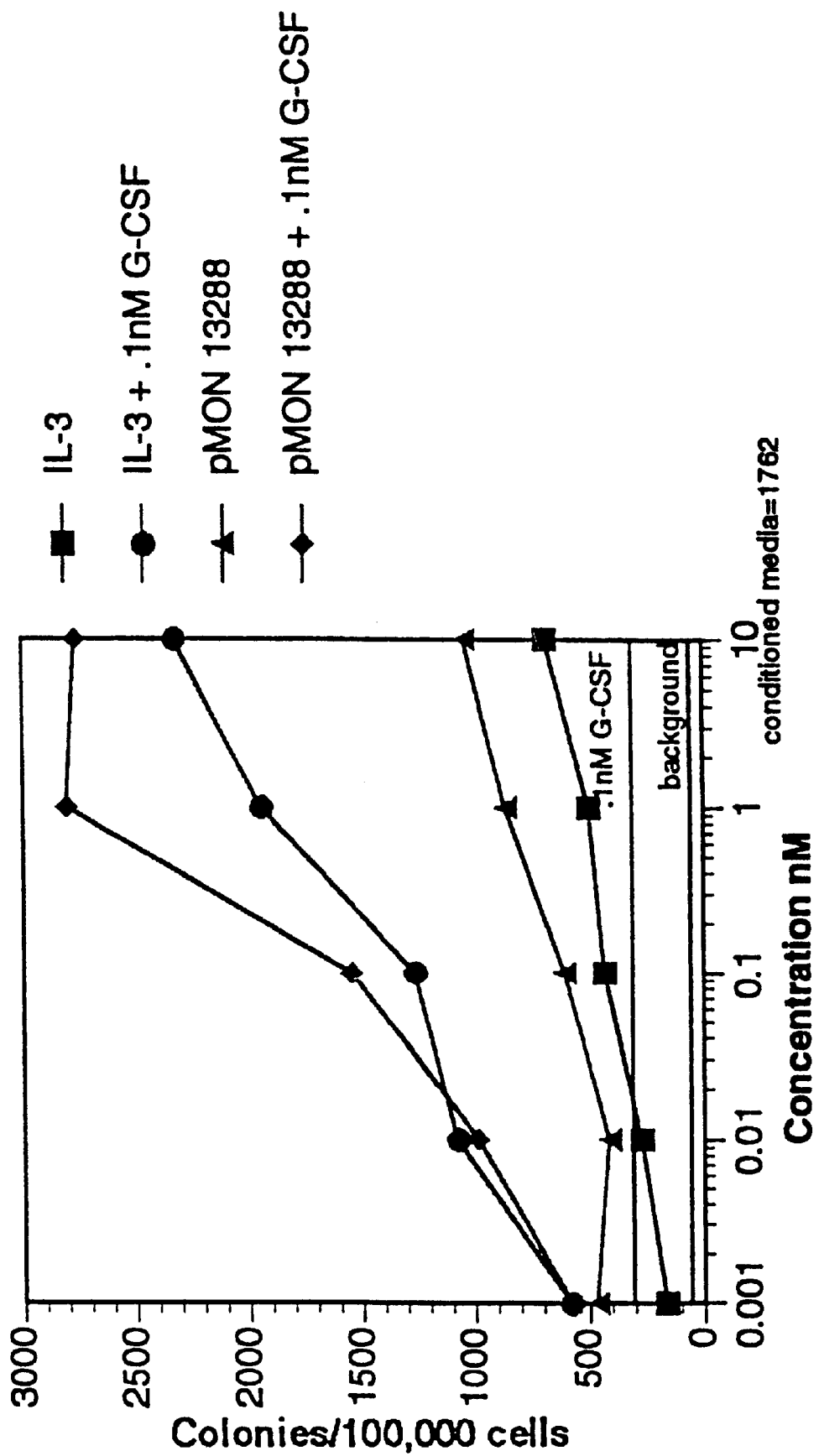
FIG. 2 shows the synergistic effects, in the methylcellulose assay, of the IL-3 variant, pMON13288, with G-CSF compared to the synergy of native IL-3 with G-CSF. Also shown are the effects of native IL-3 and the IL-3 variant, pMON13288, alone. The concentration of IL-3 is plotted versus the colony counts per 100,000 starting CD34+ cells.

The present invention encompasses methods for the ex-vivo expansion of hematopoietic cells by culturing the cells in a growth medium which comprises a recombinant human interleukin-3 (hIL-3) variant or mutant proteins (muteins) other colony stimulating factors (CSFs), cytokines, lymphokines, interleukins, hematopoietic growth factors and variants thereof (herein after collectively referred to as "hematopoietic growth factors"). The hIL-3 variant may be used either together or sequentially with the other hematopoietic growth factors. The present invention also includes methods for treatment of a patient having a hematopoietic disorder using hematopoeitic cells that were expanded using the hIL-3 variants of the present invention with other hematopoietic growth factors. Additionally, the present invention includes methods of human for treatment of a patient having a hematopoietic disorder using hematopoeitic cells that were expanded using the hIL-3 variants of the present invention with other hematopoietic growth factors.

Hematopoiesis requires a complex series of cellular events in which stem cells generate continuously into large populations of maturing cells in all major lineages. There are currently at least 20 known regulators with hematopoietic proliferative activity. Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, *Nature* 339:27, 1989). Other mechanisms could explain synergy. For example, if one signaling pathway is limited by an intermediate activation of an additional signaling pathway by a second factor may result in a superadditive response. In some cases, activation of one receptor type can induce a enhanced expression of other receptors (Metcalf, *Blood* 82(12):3515–3523 1993). Two or more factors may result in a different pattern of cell lineages then from a single factor. The use of more than one hematopoietic growth factor may have the potential clinical advantage resulting from a proliferative response that is not possible by any single factor.

Hematopoietic and other growth factors can be grouped in to two distinct families of related receptors: (1) tyrosine kinase receptors, including those for epidermal growth factor, M-CSF (Sherr, 1990) and SCF (Yarden et al., *EMBO J* 6:3341, 1987): and (2) hematopoietic receptors, not containing a tyrosine kinase domain, but exhibiting obvious homology in their extracellular domain (Bazan, *Proc. Natl. Acad. Sci. U.S.A.* 87(18):6934–8 1990). Included in this later group are erythropoietin (EPO) (D'Andrea et al., *Cell* 57:277 1989), GM-CSF (Gearing et al., *EMBO J* 8:3667 1989), IL-3 (Kitamura et al., *Cell* 66:1165 1991), G-CSF (Fukunaga et al., *J. Biol. Chem.* 265(23):14008–15 1990), IL-4 (Harada et al., 1990), IL-5 (Takaki et al., *EMBO J* 9:4367 1990), IL-6 (Yamasaki et al., *Science* 241:825 1988), IL-7 (Goodwin et al., *Cell* 60(6):941–51 1990), LIF (Gearing et al., *EMBO J* 10:2839 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Kitamura et al., *Cell* 66:1165 1991, Takaki et al., *EMBO. J.* 10(10): 2833–8 1991) and receptor complexes for IL-6, LIF and IL-11 share a common β-chain (gp130) (Taga et al., *Cell* 58(3):573–81 1989; Gearing et al., *EMBO J* 10:2839 1992). The receptor complexes of IL-2, IL-4 and IL-7 share a common γ-chain (Kondo et al., *Science* 262:1874 1993; Russell et al., *Science* 262:1880 1993; Noguchi et al., *Science* 262:1877 1993).

GM-CSF accelerates recovery of neutrophils and maintains functional capacity, yet has little demonstrable effect on platelet recovery. In contrast IL-3 promotes a slower increase recovery in neutrophils and monocytes while accelerating the recovery of platelets.

Recent studies in normal primates indicate that when IL-3 was administered before GM-CSF that the combination of IL-3 and GM-CSF promoted a synergistic rise in peripheral white blood cells and platelets (Donahue R. E. et al., *Science* 241:1820, 1988; Krumwieh D. et al., *Int. J. Cell Cloning* 8;229, 1988; and Stahl C. P. et al., *Blood* 80:2479, 1992). The synergistic effect observed in the sequential combination of IL-3 before GM-CSF may result from the expansion of GM-CSF sensitive cells by IL-3 resulting in a more efficient production of neutrophils. The coadministration of GM-CSF and IL-3 resulted in diminished neutrophils production relative to GM-CSF alone (Farese et al., *Blood* 82:3012–3018, 1993). The coadministration of IL-3 and GM-CSF, may result in down regulation of GM-CSF receptors by IL-3 thereby dampening the GM-CSF induced increase in neutrophils. However the coadministration of IL-3 and GM-CSF in a marrow-ablated rhesus monkeys promoted accelerated platelets and neutrophil recovery relative to sequential cytokine treatment or with either IL-3 or GM-CSF alone (Farese et al., *Blood* 82:3012–3018, 1993).

The in vitro activity of both IL-3 and GM-CSF has been shown to be additive with respect to stimulating larger colonies than either cytokine alone (Robinson et al., *J. Clin Invest* 79:1548, 1987; Bruno et al., *Blood* 76:671, 1989; Metcalf et al., *Blood* 182:3515–3523, 1992; Bruno et al., *Blood* 77:2339, 1991; Bridell et al., *Blood* 76:516, 1990). Recently IL-12 has been shown to synergize with IL-3 and c-kit (stem cell factor) to enhance the recovery of hemopoietic stem cells in liquid culture (Ploemacher et al., *Leukimia* 7:1381–1388, 1993).

Recent in vitro (Emerson et al., *J. Clin. Invest.* 82:1282, 1988:Sonodo et al., *PNAS* 85:4360, 1988) and in vivo (Ganser et al., *Blood* 79:2583, 1992; Donahue R. E. et al., *Science* 241:1820 1988; Krumwieh D. et al., *Int. J. Cell Cloning* 8:229, 1988; and Stahl C. P. et al., *Blood* 80:2479, 1992) results of combined IL-3 and GM-CSF treatment suggests an increased clinical efficacy in cytokine combination treatment.

As mentioned earlier some of the factors that are involved in hematopoiesis are limited to a specific cell lineage and others have much broader effects and may result in the proliferation and support of multi-lineages and there may be considerable overlap between these factors but that the proliferative profiles are distinct. This suggests that the coadministration or sequential treatment with multiple factors may have a clinical advantage. IL-3 variants of the present invention that have an increased therapeutic index, compared to native IL-3, may have a distinct clinical advantage when coadministered or used sequentially in treatment.

A non-exclusive list of growth factors, colony stimulating factors (CSFs) including; cytokines, lymphokines, interleukins, hematopoietic growth factors, which can be used in coadministration or sequential treatment with the hIL-3 variant of the present invention include GM-CSF, CSF-1, G-CSF, G-CSF Ser$^{17}$, c-mpl ligand MGDF or TPO), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF) also known as steel factor or c-kit ligand and variants thereof.

The present invention relates to to methods of ex-vivo expansion of hematopoietic cells using novel variants of human interleukin-3 (hIL-3) in which amino acid substitutions have been made at four or more positions in amino acid sequence of the polypeptide used in sequential treatment or coadministration with other colony stimulating factors. Preferred IL-3 variants of the present invention which have deletions of amino acids 1 to 14 at the N-terminus and 126 to 133 at the C-terminus and which also have four or more amino acid substitutions in the polypeptide used in coadministered or sequential treatment with other colony stimulating factors or IL-3 variants. Among the preferred IL-3 variants are those having twenty-six amino acid substitutions. The present invention includes the use of mutant polypeptides comprising minimally amino acids 15 to 118 of hIL-3 with or without additional amino acid extensions to the N-terminus and/or C-terminus which further contain four or more amino acid substitutions in the amino acid sequence of the polypeptide for ex-vivo expansion of hematpoietic progenitor cells.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al., *J. Clin. Invest.* 85:1560, 1990; Ganser, A, et al., *Blood* 76:666, 1990; Falk, S., et al., *Hematopathology* 95:355, 1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Such hIL-3 properties may include one or more of the following biological characteristics and in vivo or in vitro activities. One property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 variant proteins of the present invention is determined by DNA synthesis by human acute myelogenous leukemia cells (AML). The factor-dependent cell line AML 193 was adapted for use in testing biological activity. The biological activity of hIL-3 and hIL-3 variant proteins of the present invention is also determined by counting the colony forming units in a bone marrow assay.

Other in vitro cell based assays may also be useful to determine the synergistic effect of multiple colony stimulating factors that comprise the mixture. The following are examples of other useful assays. TF-1 proliferation assay: The TF-1 cell line was derived from bone marrow of a patient with erythroleukemia (Kitamura et al., *J. Cellular Physiology* 140:323–334, 1989). TF-1 cells respond to IL-3, GM-CSF, EPO and IL-5. 32D proliferation assay: 32D is a murine IL-3 dependent cell line which does not respond to human IL-3 but does respond to human G-CSF which is not species restricted. T1165 proliferation assay: T1165 cells are a IL-6 dependent murine cell line (Nordan et al., Science 233:566, 1986) which respond to IL-6 and IL-11. Human Plasma Clot meg-CSF Assay: Used to assay megakaryocyte colony formation activity (Mazur et al., *Blood* 57:277–286, 1981).

One object of the present invention is to provide hIL-3 variant with four or more amino acid substitutions in the polypeptide sequence, which have similar or improved biological activity in relation to native hIL-3, or the other colony stimulating factors used in ex-vivo expansion of hematopoietic cells.

The hIL-3 variants of the present invention may have hIL-3 or hIL-3-like activity. For example, they may possess one or more of the biological activities of native hIL-3 and may be useful in stimulating the production of hematopoietic cells by human or primate progenitor cells. The IL-3 variants of the present invention and pharmaceutical compositions containing them may be useful in the treatment of conditions in which hematopoietic cell populations have been reduced or destroyed due to disease or to treatments such as radiation or chemotherapy.

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory, 1989. One method of creating the preferred hIL-3 (15–125) mutant genes is cassette mutagenesis (Wells, et al., Gene, 34:315–323, 1985) in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis (Zoller and Smith, *Nucleic Acid Research*, 10:6487–6500, 1982; Zoller and Smith, *Methods in Enzymology*, 100:468–500, 1983; Zoller and Smith, *DNA*, 3: 479, 1984 Smith M., *Ann. Rev. Genet.*, 19:423–462, 1985; Kunkel, *Proc. Natl. Acad. Sci. USA*, 82: 488–492, 1985, Taylor, et al., *Nucl. Acids Res.*, 13:8764–8785 (1985), Deng and Nickoloff, Anal-Biochem 200:81–88, 1992) or polymerase chain reaction (PCR) techniques (Saiki, *Science* 230:1350–1354, 1985).

Additional details about recombinant techniques for construction of DNA sequences that encode the hIL-3 variant proteins, plasmid DNA vectors for use in the expression of these novel hIL-3 variant proteins, methods for producing the hIL-3 variant proteins in bacterial cells, mammalian cells, or insect cells and the in-vitro and in-vivo biological activity of the IL-3 variants can be found in WO 94/12638. It is understood that the hIL-3 variant proteins of the present invention, used for the ex-vivo expansion of hematopoietic cells, can be made by other methods known to those skilled in the art. The biological activity of the IL-3 variants co-administered with other hematopoietic growth factors can be found in WO 95/20977.

Hematopoietic cells, that have been expanded ex-vivo using hIL-3 variants of the present invention with other hematopoietic growth factors, may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the IL-3 variants of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these expanded cells may avoid undesirable side effects caused by treatment with presently available drugs.

Hematopoietic cells that have been expanded ex-vivo may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

Additionally, hematopoietic cells that have been expanded ex-vivo may be useful in the treatment or prevention of thrombocytopenia. Currently the only therapy for thrombocytopenia is platelet transfusions which are costly and carry the significant risks of infection (HIV, HBV) and alloimunization. Administering the expanded cells may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenytoin or carbamazepine, antithyroids such as propylthiouracil and methimazole and diuretics. The use hematopoietic cells, that have been expanded ex-vivo, may be useful in preventing or treating the bone marrow suppression or hematopoietic deficiencies which often occur in patients treated with these drugs. Hematopoietic deficiencies may also occur as a result of viral, microbial or parasitic infections and as a result of treatment for renal disease or renal failure, e.g., dialysis. The use hematopoietic cells, that have been expanded ex-vivo, may be useful in treating such hematopoietic deficiency. Various immunodeficiencies e.g., in T and/or B lymphocytes, or immune disorders, e.g., rheumatoid arthritis, may also be beneficially affected by treatment with hematopoietic cells, that have been expanded ex-vivo. Immunodeficiencies may be the result of viral infections e.g. HTLVI, HTLVII, HTLVIII, severe exposure to radiation, cancer therapy or the result of other medical treatment. Hematopoietic cells, that have been expanded ex-vivo may also be employed, alone or in combination with other colony stimulating factors, in the treatment of blood cell deficiencies, including thrombocytopenia, neutropenia, or anemia.

Another projected clinical use of growth factors has been in the in vitro activation of hematopoietic progenitors and stem cells for gene therapy. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy.

Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, Science 270:404–410 (1995) include; 1) the treatment of many congenital metabolic disorders and immunodifiencies (Kay and Woo, *Trends Genet.* 10:253–257 (1994), 2) neurological disorders (Freedmann, Trends Genet. 10:210–214 (1994), 3) cancer (Culver and Blaese, *Trends Genet.* 10:174–178 (1994) and 4) infectious diseases (Gilboa and Smith, *Trends Genet.* 10:139–144 (1994). Due to the long life-span of hematopoietic progenitor cells and the distribution of their daughter cells throughout the entire body, hematopoietic progenitor cells are good candidates for ex vivo gene transfection include the treatment of many congenital metabolic disorders and immunodifiencies (Kay and Woo, Trends Genet. 10:253–257 (1994) neurological disorders (Freedmann, Trends Genet. 10:210–214 (1994), cancer (Culver and Blaese, Trends Genet. 10:174–178 (1994) and infectious diseases (Gilboa and Smith, Trends Genet. 10:139–144 (1994).

There are a variety of methods, known to those with skill in the art, for introducing genetic material into a host cell. A number of vectors, both viral and non-viral have been developed for transferring therapeutic genes into primary cells. Viral based vectors include; 1) replication-deficient recombinant retrovirus (Boris-Lawrie and Temin, *Curr. Opin. Genet. Dev.* 3:102–109 (1993), Boris-Lawrie and Temin, *Annal. New York Acad. Sci.* 716:59–71 (1994), Miller, Current Top. Microbiol. Immunol. 158:1–24 (1992) and replication-deficient recombinant adenovirus (Berkner, *BioTechniques* 6:616–629 (1988), Berkner, Current Top. Microbiol. Immunol. 158:39–66 (1992), Brody and Crystal, *Annal. New York Acad. Sci.* 716:90–103 (1994). Non-viral based vectors include protein/DNA complexes (Cristiano et al., *PNAS USA*. 90:2122–2126 (1993), Curiel et al., *PNAS USA* 88:8850–8854 (1991), Curiel, *Annal. New York Acad. Sci.* 716:36–58 (1994), electroporation and liposome mediated delivery such as cationic liposomes (Farhood et al., *Annal. New York Acad. Sci.* 716:23–35 (1994).

The present invention provides an improvement to the existing methods of expanding hematopoietic cells, which new genetic material has been introduced, in that it provides methods utilizing the co-administration or sequental use novel hIL-3 variants of the present invention that may have improved biological activity, with other hematopoietic growth factors, which together may including an activity not seen by any single hematopoietic growth factor.

The present invention includes methods of ex-vivo expansion of hematopoietic cells and uses of the expanded cells to treat patient having a hematopoietic disorder:

The dosage regimen involved in ex-vivo expansion of hematopoietic cells and methods for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 1 ng to 100 ng of non-glycosylated IL-3 protein per mL of culture medium and 1 ng/mL of other hematopoietic growth factors may be in the range of 1 ng to 100 ng per mL of culture medium. This dosage regimen is referenced to a standard level of biological activity which recognizes that native IL-3 generally possesses an EC50 at or about 10 picoMolar to 100 picoMolar in the AML proliferation assay described herein. Therefore, dosages would be adjusted relative to the activity of a given mutein vs. the activity of native (reference) IL-3 and it would not be unreasonable to note that dosage regimens may include doses as low as 0.1 ng and as high as 1 milligram per mL of culture medium. In addition, there may exist specific circumstances where dosages of IL-3 mutein would be adjusted higher or lower. Other hematopoietic growth factors could be used as low as 1 pg/mL and as high as 1 mg/mL depending on the IL-3 variant used, the various combination of hematopoietic growth factors used and the nature of the expanded hematopoietic cell population that is desired. Other factors that could effect the dosage of the IL-3 variants and other hematopoietic growth factors include; co-administration with chemotherapeutic drugs and/or radiation; the use of glycosylated IL-3 mutein; and various patient-related issues mentioned earlier in this section.

hIL-3 Sandwich ELISA

The IL-3 variant protein concentrations can be determined using a sandwich ELISA based on an affinity purified polyclonal goat anti-rhIL-3. Microtiter plates (Dynatech Immulon II) were coated with 150 µl goat-anti-rhIL-3 at a concentration of approximately 1 µg/ml in 100 mM NaHCO3, pH 8.2. Plates were incubated overnight at room temperature in a chamber maintaining 100% humidity. Wells were emptied and the remaining reactive sites on the plate were blocked with 200 1l of solution containing 10 mM PBS, 3% BSA and 0.05% Tween 20, pH 7.4 for 1 hour at 37° C. and 100% humidity. Wells were emptied and washed 4× with 150 mM NaCl containing 0.05% Tween 20 (wash buffer). Each well then receives 150 µl of dilution buffer (10 mM PBS containing 0.1% BSA, 0.01% Tween 20, pH 7.4), containing rhIL-3 standard, control, sample or dilution buffer alone. A standard curve was prepared with concentrations ranging from 0.125 ng/ml to 5 ng/ml using a stock solution of rhIL-3 (concentration determined by amino acid composition analysis). Plates were incubated 2.5 hours at 37° C. and 100% humidity. Wells were emptied and each plate was washed 4× with wash buffer. Each well then received 150 µl of an optimal dilution (as determined in a checkerboard assay format) of goat anti-rhIL-3 conjugated to horseradish peroxidase. Plates were incubated 1.5 hours at 37° C. and 100% humidity. Wells were emptied and each plate was washed 4× with wash buffer. Each well then received 150 µl of ABTS substrate solution (Kirkegaard and Perry). Plates were incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples were calculated from the standard curve using software supplied with the plate reader.

The following examples will illustrate the invention in greater detail although it will be understood that the invention is not limited to these specific examples.

EXAMPLE 1

AML Proliferation Assay for Bioactive Human Interleukin-3 The factor-dependent cell line AML 193 was obtained from the American Type Culture Collection (ATCC, Rockville, Md.). This cell line, established from a patient with acute myelogenous leukemia, was a growth factor dependent cell line which displayed enhanced growth in GM/CSF supplemented medium (Lange, B., et al., *Blood* 70:192, 1987; Valtieri, M., et al., *J. Immunol* 138:4042, 1987). The ability of AML 193 cells to proliferate in the presence of human IL-3 has also been documented. (Santoli, D., et al., *J. Immunol* 139:348, 1987). A cell line variant was used, AML 193 1.3, which was adapted for long term growth in IL-3 by washing out the growth factors and starving the cytokine dependent AML 193 cells for growth factors for 24 hours. The cells were then replated at $1 \times 10^5$ cells/well in a 24 well plate in media containing 100 U/ml IL-3. It took approximately 2 months for the cells to grow rapidly in IL-3. These cells were maintained as AML 193 1.3 thereafter by supplementing tissue culture medium (see below) with human IL-3.

AML 193 1.3 cells were washed 6 times in cold Hanks balanced salt solution (HBSS, Gibco, Grand Island, N.Y.) by centrifuging cell suspensions at 250×g for 10 minutes followed by decantation of supernatant. Pelleted cells were resuspended in HBSS and the procedure was repeated until six wash cycles were completed. Cells washed six times by this procedure were resuspended in tissue culture medium at a density ranging from $2 \times 10^5$ to $5 \times 10^5$ viable cells/ml. This medium was prepared by supplementing Iscove's modified Dulbecco's Medium (IMDM, Hazelton, Lenexa, Kans.) with albumin, transferrin, lipids and 2-mercaptoethanol. Bovine albumin (Boehringer-Mannheim, Indianapolis, Ind.) was added at 500 µg/ml; human transferrin (Boehringer-Mannheim, Indianapolis, Ind.) was added at 100 µg/ml; soybean lipid (Boehringer-Mannheim, Indianapolis, Ind.) was added at 50 µg/ml; and 2-mercaptoethanol (Sigma, St. Louis, Mo.) was added at $5 \times 10^{-5}$ M.

Serial dilutions of human interleukin-3 or human interleukin-3 variant protein (hIL-3 mutein) were made in triplicate series in tissue culture medium supplemented as stated above in 96 well Costar 3596 tissue culture plates. Each well contained 50 µl of medium containing interleukin-3 or interleukin-3 variant protein once serial dilutions were completed. Control wells contained tissue culture medium alone (negative control). AML 193 1.3 cell suspensions prepared as above were added to each well by pipetting 50 μl (2.5×10⁴ cells) into each well. Tissue culture plates were incubated at 37° C. with 5% $CO_2$ in humidified air for 3 days. On day 3, 0.5 μCi ³H-thymidine (2 Ci/mM, New England Nuclear, Boston, Mass.) was added in 50 μl of tissue culture medium. Cultures were incubated at 37° C. with 5% $CO_2$ in humidified air for 18–24 hours. Cellular DNA was harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Betaplate model 1205 scintillation counter (Pharmacia LKB, Gaithersburg, Md.) and data was expressed as counts per minute of ³H-thymidine incorporated into cells from each tissue culture well. Activity of each human interleukin-3 preparation or human interleukin-3 variant preparation was quantitated by measuring cell proliferation (³H-thymidine incorporation) induced by graded concentrations of interleukin-3 or interleukin-3 variant. Typically, concentration ranges from 0.05 pM–10⁵ pM were quantitated in these assays. Activity was determined by measuring the dose of interleukin-3 or interleukin-3 variant which provides 50% of maximal proliferation [$EC_{50}$=0.5× (maximum average counts per minute of ³H-thymidine incorporated per well among triplicate cultures of all concentrations of interleukin-3 tested—background proliferation measured by ³H-thymidine incorporation observed in triplicate cultures lacking interleukin-3]. This $EC_{50}$ value is also equivalent to 1 unit of bioactivity. Every assay was performed with native interleukin-3 as a reference standard so that relative activity levels could be assigned.

EXAMPLE 2

Methylcellulose Assay

This assay provides a reasonable approximation of the growth activity of colony stimulating factors to stimulate normal bone marrow cells to produce different types of hematopoietic colonies in vitro (Bradley et al., *Aust. Exp. Biol. Med. Sci.* 44:287–300 1966; Pluznik et al., *J Cell Comp Physiol* 66:319–324 1965).

Methods

Approximately 30 ml of fresh, normal, healthy bone marrow aspirate are obtained from individuals. Under sterile conditions samples are diluted 1:5 with a 1×PBS (#14040.059 Life Technologies, Gaithersburg, Md.) solution in a 50 ml conical tube (#25339–50 Corning, Corning Md.). Ficoll (Histopaque-1077 Sigma H-8889) is layered under the diluted sample and centrifuged, 300×g for 30 min. The mononuclear cell band is removed and washed two times in 1× PBS and once with 1% BSA PBS (CellPro Co., Bothel, Wash.). Mononuclear cells are counted and CD34+cells are selected using the Ceprate LC (CD34) Kit (CellPro Co., Bothel, Wash.) column. This fractionation is performed since all stem and progenitor cells within the bone marrow display CD34 surface antigen. Alternatively whole bone marrow or peripheral blood may be used.

Cultures are set up in triplicate wells with a final volume of 0.1 ml in 48 well tissue culture plates (#3548 CoStar, Cambridge, Mass.). Culture medium is purchased from Terry Fox Labs. (HCC-4330 medium (Terry Fox Labs, Vancouver, B.C., Canada)). 600–1000 CD34+ cells are added per well. Native IL-3 and IL-3 variants are added to give final concentrations ranging from 0.001 nM–10 nM. G-CSF and GM-CSF and C-Kit ligand are added at a final concentration of 0.1 nM. Native IL-3 and IL-3 variants are supplied in house. C-Kit Ligand (#255-CS), G-CSF (#214-CS) and GM-CSF (#215-GM) are purchased from R&D Systems (Minneapolis, Minn.).

Cultures are resuspended using an Eppendorf repeater and 0.1 ml is dispensed per well. Control (baseline response) cultures received no colony stimulating factors. Positive control cultures received conditioned media (PHA stimulated human cells:Terry Fox Lab. H2400). Cultures are incubated at 37° C., 5% CO2 in humidified air. Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

EXAMPLE 3

The synergistic effect of the IL-3 variant, pMON13288, with G-CSF was evaluated in the methylcellulose assay compared to that of native IL-3 with G-CSF. G-CSF was added to each culture at a concentration of 0.1 nM. Native IL-3 and the IL-3 variant, pMON13288, were added at final concentrations ranging from 0.001 nM to 10 nM. Colonies were counted on the day of peak response (days 10–11). pMON13288 activates more progenitor cells than native IL-3 (FIG. 2). Native IL-3 plus G-CSF and the IL-3 variant, pMON13288, plus G-CSF resulted in an increase in colony number greater than the additive effect of the individual proteins alone (FIG. 2). The synergistic effect of the IL-3 variant, pMON13288, with G-CSF was greater than that of native IL-3 with G-CSF. Hematopoietic colony forming activity of the IL-3 variant, pMON13288, was multi-lineage whereas G-CSF alone activates primarily granulocytic cells at molar equivalent doses. In FIG. 2 the concentration of IL-3 is plotted versus the colony counts per 100,000 starting CD34+ cells.

EXAMPLE 4

Figure 3:
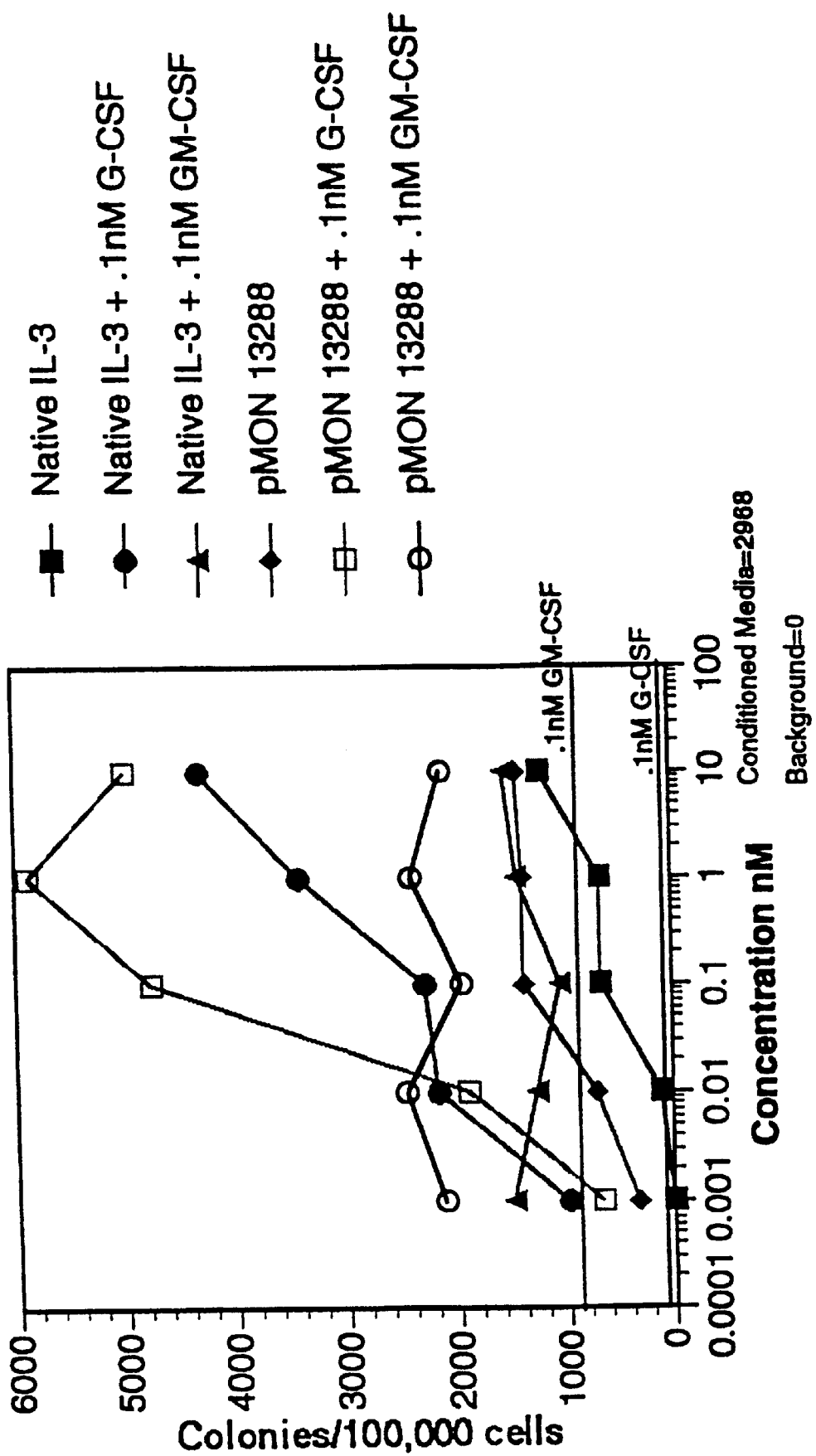
FIG. 3 shows the synergistic effects, in the methylcellulose assay, of the IL-3 variant, pMON13288, with GM-CSF compared to the synergy of native IL-3 with GM-CSF. Also shown are the effects of native IL-3 and the IL-3 variant, pMON13288, alone. The concentration of IL-3 is plotted versus the colony counts per 100,000 starting CD34+ cells.
Figure 4:
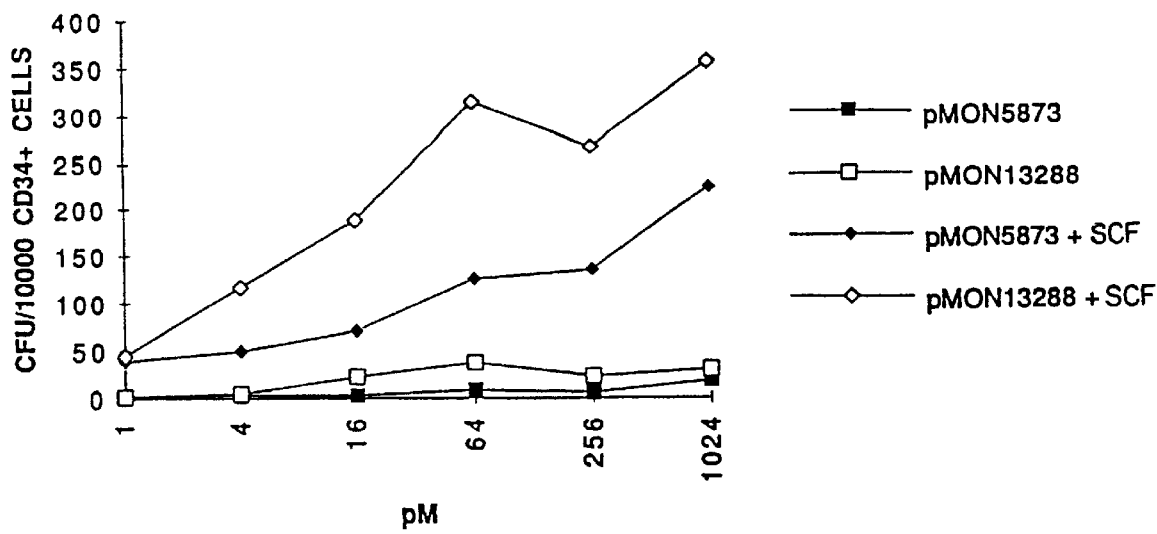
FIG. 4 shows the synergistic effects, in the cord blood assay, of the IL-3 variant, pMON13288, with stem cell factor (SCF) compared to the synergy of native IL-3 (pMON5873) with stem cell factor (SCF). Also shown are the effects of native IL-3 (pMON5873) and the IL-3 variant, pMON13288, alone. The concentration of IL-3 is plotted versus the colony counts (CFU) per 10,000 starting CD34+ cells.
Figure 5:
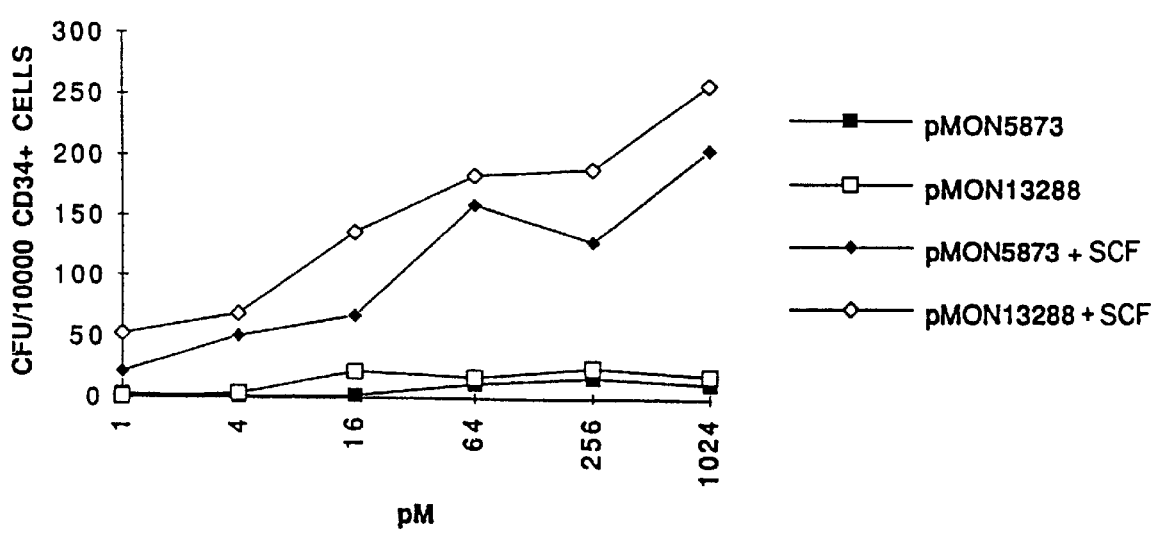
FIG. 5 shows the synergistic effects, in the cord blood assay, of the IL-3 variant, pMON13288, with stem cell factor (SCF) compared to the synergy of native IL-3 (PMON5873) with stem cell factor (SCF). Also shown are the effects of native IL-3 (PMON5873) and the IL-3 variant, pMON13288, alone. The concentration of IL-3 is plotted versus the colony counts (CFU) per 10,000 starting CD34+ cells.

The synergistic effect of the IL-3 variant, pMON13288, with GM-CSF was evaluated in the methylcellulose assay compared to that of native IL-3 with GM-CSF. GM-CSF was added to each culture at a concentration of 0.1 nM. Native IL-3 and the IL-3 variant, pMON13288, were added at final concentrations ranging from 0.001 nM to 10 nM. Colonies were counted on the day of peak response (days 10–11). pMON13288 activates more progenitor cells than native IL-3 (FIG. 3). Native IL-3 plus GM-CSF and the IL-3 variant, pMON13288, plus GM-CSF resulted in an increase in colony number greater than the effect of the individual proteins alone (FIG. 3). The synergistic effect of the IL-3 variant, pMON13288, with GM-CSF was greater than that of native IL-3 with GM-CSF. In FIG. 3 the concentration of IL-3 is plotted versus the colony counts per 100,000 starting CD34+ cells.

EXAMPLE 5

Methylcellulose assays for native IL-3, pMON5873, were carried out in methylcellulose, with or without EPO. Although EPO increased the total number of colonies, it didn't appear to increase CFU-GM, which are of more interest. The presence of erythroid colonies also made scoring more subjective, because one must distinguish between multifocal BFU-E vs several closely associated single focus CFU-E. EPO also gave a high background of total colonies, which would tend to obscure the dose dependent response of CFU-GM to other CSFs.

Methylcellulose assays comparing native IL-3 (pMON5873) to the IL-3 variant, pMON13288 were carried out in the presence of stem cell factor (SCF) without EPO. SCF gives no background response in these assays, but appears to increase the dose dependent response of CFU-GM to both native IL-3 (PMON5873) and the IL-3 variant, pMON13288. This result is consistent with reports in the literature of in vitro synergies between IL-3 and SCF (Migliaccio et al., 1992). The IL-3 variant, pMON13288, appears to be more potent in these assays, and gives a greater maximum number of colonies (also larger) than native IL-3 (PMON5873).

EXAMPLE 6

Human Cord Blood Hemopietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., 1992; Mayani et al., 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it should be possible to assay specifically for granulocyte/macrophage colonies (CFU-GM), for megakaryocyte CSF activity, or for high proliferative potential colony forming cell (HPP-CFC) activity.

Methods

Mononuclear cells (MNC) are isolated from cord blood within 24 hrs of collection, using a standard density gradient (1.077g/ml Histopaque). Cord blood MNC have been further enriched for stem cells and progenitors by several procedures, including immunomagnetic selection for CD14−, CD34+cells; panning for SBA−, CD34+fraction using coated flasks from Applied Immune Science (Santa Clara, Calif.); and CD34+selection using a CellPro (Bothell, Wash.) avidin column. Either freshly isolated or cryopreserved CD34+cell enriched fractions are used for the assay. Duplicate cultures for each serial dilution of sample (concentration range from 1 pM to 1204 pM) are prepared with 1×104 cells in 1 ml of 0.9% methycellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50ng/ml (Biosource International, Camarillo, Calif.) was added. After culturing for 7–9 days, colonies containing >30 cells are counted. In order to rule out subjective bias in scoring, assays are scored blind.

EXAMPLE 7

Analysis of c-mmpl ligand proliferative activity
Methods
1. Bone marrow proliferation assay
a. CD34+Cell Purification:

Between 15–20 ml bone marrow aspirates were obtained from normal allogeneic marrow donors after informed consent. Cells were diluted 1:3 in phosphate buffered saline (PBS, Gibco-BRL), 30 ml were layered over 15 ml Histopaque-1077 (Sigma) and centrifuged for 30 minutes at 300 RCF. The mononuclear interface layer was collected and washed in PBS. CD34+ cells were enriched from the mononuclear cell preparation using an affinity column per manufacturers instructions (CellPro, Inc, Bothell Wash.). After enrichment, the purity of CD34+ cells was 70% on average as determined by using flow cytometric analysis using anti CD34 monoclonal antibody conjugated to fluorescein and anti CD38 conjugated to phycoerythrin (Becton Dickinson, San Jose Calif.).

Cells were resuspended at 40,000 cells/ml in X-Vivo 10 media (Bio-Whittaker, Walkersville, Md.) and 1 ml was plated in 12-well tissue culture plates (Costar). The growth factor rhIL-3 was added at 100 ng/ml (pMON5873) was added to some wells. hIL3 variant, pMON13288 was used at 10 ng/ml or 100 ng/ml. Conditioned media from BHK cells transfected with plasmid encoding c-mpl ligand were tested by addition of 100 μl of supernatant added to 1 ml cultures (approximately a 10% dilution). Cells were incubated at 37° C. for 8–14 days at 5% CO2 in a 37° C. humidified incubator.

b. Cell Harvest and Analysis:

At the end of the culture period a total cell count was obtained for each condition. For fluorescence analysis and ploidy determination cells were washed in megakaryocyte buffer (MK buffer, 13.6 mM Sodium Citrate, 1 mM Theophylline, 2.2 μM PGE1, 11 mM Glucose, 3% w/v BSA, in PBS, pH 7.4,) [See Tomer et al., Blood 70, 1987, pp. 1736–42] resuspended in 500 μl of MK buffer containing anti-CD41a FITC antibody (1:200, AMAC, Westbrook, Me.) and washed in MK buffer. For DNA analysis cells were permeablized in MK buffer containing 0.5% Tween 20 (Fisher, Fair Lawn N.J.) for 20 min. on ice followed by fixation in 0.5% Tween-20 and 1% paraformaldehyde (Fisher Chemical) for 30 minutes followed by incubation in Propidium Iodide (Calbiochem La Jolla Calif.) (50 μg/ml) with RNA-ase (400 U/ml) in 55% v/v MK buffer (200 mOsm) for 1–2 hours on ice. Cells were analyzed on a FACScan or Vantage flow cytometer (Becton Dickinson, San Jose, Calif.). Green fluorescence (CD41a-FITC) was collected along with linear and log signals for red fluorescence (PI) to determine DNA ploidy. All cells were collected to determine the percent of cells that were CD41+. Data analysis was performed using software by LYSIS (Becton Dickinson, San Jose, Calif.). Percent of cells expressing the CD41 antigen was obtained from flow cytometry analysis (Percent). Absolute (Abs) number of CD41+ cells/ml was calculated by: (Abs)=(Cell Count)*(Percent)/100.

2. Megakaryocyte fibrin clot assay.

CD34+enriched population were isolated as described above. Cells were suspended at 25,000 cells/ml with/without cytokine(s) in a media consisting of a base Iscoves IMDM media supplemented with 0.3% BSA, 0.4mg/ml apo-transferrin, 6.67 μM $FeCl_2$, 25 μg/ml $CaCl_2$, 25 μg/ml L-asparagine, 500 μg/ml E-amino-n-caproic acid and Penicillin/Streptomycin. Prior to plating into 35 mm plates, thrombin was added (0.25 Units/ml) to initiate clot formation. Cells were incubated at 37° C. for 13 days at 5% $CO_2$ in a 37° C. humidified incubator.

At the end of the culture period plates were fixed with Methanol:Acetone (1:3), air dried and stored at −20° C. until staining. A peroxidase immunocytochemistry staining procedure was used (Zymed, Histostain-SP. San Francisco, Calif.) using a cocktail of primary monoclonal antibodies consisting of anti CD41a, CD42 and CD61. Colonies were counted after staining and classified as negative, CFU-MK (small colonies, 1–2 foci and less that approx. 25 cells), BFU-MK (large, multi-foci colonies with >25 cells) or mixed colonies (mixture of both positive and negative cells).

EXAMPLE 8

Co-administration of hIL-3 variant, p-MON13288, and c-mpl ligand (Meg-CSF) in liquid culture The co-administration of hIL-3 variant, pMON13288, and c-mpl ligand (Meg-CSF) has a more than additive effect on megakaryocyte expansion than either cytokine alone in the liquid culture assay CD34+ cells were isolated as described in the methods section. The assay was set up as described in the methods section except that cells were plated at 4000 cells/100 μl in a 96-well plate. pMON26448 or a mock transfectant was evaluated by adding 10 μl to each well (10% final). Supernatant from transfected BHK cells were tested +/− hIL3 variant, pMON13288 (10 ng/ml). At day 10 phenotypic analysis was performed by flow cytometry. Supernatant from pMON26448 induced selective expansion of CD41a+ cells. Total cell number increased from the 4000 cells plated to 22,000 at the end of the assay (Table 1). Addition of hIL3 variant, pMON13288 alone increased total cell numbers (19,000 cells at end of assay) with 17% of cells expressing CD41a. Combination of pMON26448 with hIL3 variant, pMON13288 resulted in 56% of cells expressing CD41a. Total cell expansion in the combination assay was more than additive with 86,000 cells/well. Both the increased total cell number and the higher percentage of cells expressing CD41a resulted in an increase in total number CD41+ cells that also was more than additive as compared to either cytokine alone (48,000 vs. 3,320 and 18,480).

TABLE 1

| Cytokine Treatment | Cells/Well | % CD41a Positive | # CD41+ Cells/Well |
| --- | --- | --- | --- |
| pMON13288 | 19,000 | 17 | 3,230 |
| pMON26448 | 22,000 | 84 | 18,480 |
| pMON26448 + pMON13288 | 86,000 | 56 | 48,160 |

In another experiment CD34+ cells were isolated from Human bone marrow using a CD34 affinity column (Cellpro). Purified CD34+ cells were resuspended in X-Vivo tissue culture media at 40,000 cells/ml. pMON26448 or a mock transfectant (10%) was evaluated with/without hIL3 variant, pMON13288 or native IL3. At day 8 phenotypic analysis was done using flow cytometry. As was seen in the table below (Table 2a–c). IL3, both concentrations of hIL3 variant, pMON13288 and pMON26448 increased total cell number substantially. Combination of cytokines further expanded cell populations. pMON26448 increased the percent of CD41+ cells from 2% in the control group to 35%. IL3 or hIL3 variant, pMON13288 increased the percent of CD41+ cells modestly (from 2% to 5%). Combining pMON26448 with IL3 or hIL3 variant, pMON13288 resulted in a more than additive number of CD41+cells as compared to the sum of either cytokine alone (Table 2c).

TABLE 2

| Cytokine treatment | Media | IL-3 (100 ng/ml) | pMON13288 (10 ng/ml) | pMON13288 (100 ng/ml) |
| --- | --- | --- | --- | --- |
| a. Total Cells/Well | | | | |
| Media | 30,000 | 112,000 | 275,000 | 150,000 |
| Mock | 10,000 | 153,000 | 235,000 | 260,000 |
| pMON26448 | 135,000 | 655,000 | 625,000 | 500,000 |
| b. % CD41a+ | | | | |
| Media | 2 | 7 | 5 | 5 |
| Mock | 2 | 14 | 5 | 9 |
| pMON26448 | 35 | 35 | 28 | 29 |
| c. Total CD41a+ Cells | | | | |
| Media | 600 | 7,840 | 13,750 | 7,500 |
| Mock | 200 | 21,420 | 11,750 | 23,400 |
| pMON26448 | 47,250 | 229,250 | 175,000 | 145,000 |

EXAMPLE 9

Co-administration of hIL-3 variant, pMON13288, and c-mdl ligand (Meg-CSF) in Fibrin Clot Assay The co-administration of hIL-3 variant, pMON13288, and c-mpl ligand (Meg-CSF) has a more than additive effect on megakaryocyte than either cytokine alone.

Fibrin clot cultures were set up as described in methods section. pMON26448 is the 1-153 form of c-mpl ligand (Meg-CSF). Incubation in the presence of hIL3 variant, pMON13288 gave rise to colonies that were predominantly negative for megakaryocyte markers (86/114, (Table 3)) except for number of small CFU-MK colonies (23/114). pMON26448 alone gave rise primarily to CFU-MK colonies (172/175) with only a few number of negative colonies (3/175). Combination of hIL3 variant, pMON13288 and pMON26448 gave rise to a large number of positive colonies (295/414) that were predominantly of the BFU-MK morphology. There were a negative colonies as well (119/414). Total number of positive colonies with co-administration was more than additive than with either cytokine alone.

TABLE 3.

| Cytokine treatment | Negative | CFU-MK | BFU-MK | Mixed | Total Colonies |
| --- | --- | --- | --- | --- | --- |
| | Colonies/Well | | | | |
| pMON13288 | 86 | 23 | 0 | 5 | 114 |
| pMON26448 | 3 | 73 | 98 | 1 | 175 |
| pMON26448 + pMON13288 | 119 | 29 | 244 | 22 | 414 |
| | Colonies/100,000 plated | | | | |
| pMON13288 | 344 | 92 | 0 | 20 | 456 |
| pMON26448 | 12 | 292 | 392 | 4 | 700 |
| pMON26448 + pMON13288 | 476 | 116 | 976 | 88 | 1656 |

EXAMPLE 10

Ex vivo Expansion of CD34+ cells From Peripheral Blood Using p-MON13288 vs. Native IL-3 +/− SCF Flow Cytometry Evaluation The percentage of CD34+ cells in the thawed peripheral blood cell population was determined by flow cytometry. Cells were removed from the selected cell population and placed into two centrifuge tube and washed once in 9/1% albumin Phosphate buffer (PAB). Twenty microliters of anti-CD34 monoclonal antibody (8G12-FITC) or mouse monoclonal antibody IgG-FITC control was added to the tube. The tubes were incubated for 15 minutes on ice. The cells were washed once with PAB and resuspended in approximately 0.5 mL PAB. Propidium iodide (2 ug/mL) was added to each tube just prior to the analysis on the FACSort or FACScan. Selected cells that contain greater than 80% CD34+ cells were used to initiate the cultures.

On day 12, cultures were harvested and evaluated with CD41A-FITC (a megakaryocyte marker), CD15-FITC and CD11b-PE (early to late neutrophil marker) and CD34 by flow cytometry, using the same processes of preparation and analysis as described above.

Colony Assay Evaluation

Colony assay evaluation was performed on day 0 with 500–1000 selected CD34+cells per dish and again on day 12 of culture with 5,000–10,000 cultured cells per dish. The cells were added to a colony assay culture tube containing 3 mL of Terry Fox Iscove's based methylcellulose and the following growth factors: 20 ng/mL SCF, 10 U/mL EPO, 300 U/mL GM-CSF, 300 U/mL G-CSF, 30 U/mL IL3 and 40 ng/mL IL6. Two 35mm tissue culture dishes containing 1 mL were set up. All dishes were incubated at 37° C., 5% carbon dioxide, 5% oxygen and high humidity for 13–15 days. The dishes were scored for myeloid (CFU-GM), erythroid (BFU-E) or mixed myeloid and erythroid colonies (CFU-mix) using a Nikon SMZU stereoscope.

Cell Morphology Evaluation

On day 12 of culture cells were analyzed for cell morphology after Wright-Giemsa staining. Cultured cells were cytocentrifuged onto slides at 1000 rpm for 4 minutes. Each slide contained approximately 10000–20000 cells. Slides were allowed to air dry before staining with 0.5 mL Wright-Giemsa for 1 minutes and 0.5 mL tap water for 1–2 minutes. Slides were cover-slipped and evaluated using a Microstar light microscope. A differential cell count of neutrophils, megakaryocytes and other blood cells was performed.

Results

CD34+ Selection

Studies were performed on CD34+ cells selected using the Isolex™ 300 magnetic Cell Separator from apheresis products from normal donors mobilized with G-CSF. The selected cells were stored in X-VIVO 10 +12.5%HSA containing 10% DMSO in liquid nitrogen until required. Cultures were initiated as described in the methods section.

Proliferation Index Of Cultures At Day 12

The proliferation index of cultures was calculated by diving the cell concentration at day 5–7 by $5 \times 10^4$ and then multiplying it by the cell concentration at day 12 divided by $1 \times 10^5$. A summary of the proliferation index obtained from these CD34+ cell cultures is shown in Table 4.

Flow Cytometry Evaluation Of Neutrophil Precursors

The percentage of neutrophil precursors in the CD34+ cell cultures at day 12 was assessed by flow cytometry using the CD15 marker for early to late neutrophil precursors and the CD11b marker found on late neutrophil precursors determined is shown in Table 4.

Flow Cytometry Evaluation Of Megakaryocytes

The percentage of Mks in the CD34+ cell cultures was assessed by flow cytometry using the CD41a marker for megakaryocytes. The percentage of Mks observed in the CD34+ cell cultures is shown in Table 4.

Flow Cytometry Evaluation Of CD34+ Cells

The percentage of CD34+ cells present in the cultures at day 12 was determined by flow cytometry. The percentage of CD34+ cells still remaining in the cultures at day 12 ranged from 0.103–19.3%, with no significant difference or patterns observed with the different growth factor combinations.

Total Number Of Megakaryocytes Generated In Culture

The total number of megakaryocytes present in each culture is calculated by multiplying the total number of cells at day 12 by the percentage of CD15+ cells and is shown in Table 4.

Colony Forming Unit Granulocyte-Macrophage (CFU-GM) Index

CFU-GM index is calculate by dividing the total number of GM-colonies obtained at day 12 by the number of GM-colonies obtained at day 0. A CFU-GM index of 1 indicates that the number of colonies at day 12 is equivalent to the number of colonies at the start of the culture. A summary of the CFU-GM index for these cultures is shown in Table 4.

Colony Forming Unit (CFU) Index

CFU index is calculated by dividing the total number of colonies (CFU-GM, BFU-E and mixed) obtained at day 12 by the total number of colonies obtained at day 0. A CFU index of 1 indicates that the number of colonies at day 12 is equivalent to the number of colonies at the start of the culture. A summary of the CFU index for these cultures is shown in Table 4.

TABLE 4

| | | Ex-vivo Expansion | | | | |
|---|---|---|---|---|---|---|
| Assay | Growth Factor | Donor #1 | Donor #2 | Donor #3 | Donor #4 | Donor #5 |
| Proliferation Index of CD34+ Cell Cultures at Day 12 | pMON13288 | 31.2 | 44.4 | 13.9 | 18.3 | 5 |
| | pMON13288 + SCF | 100 | 183 | 88 | 17.2 | 44.6 |
| | native hIL-3 | 9 | 4.1 | 10.7 | 1 | 1.42 |
| | native hIL-3 + SCF | 70.5 | 61.3 | 62.3 | 22.6 | 12.2 |
| Percentage CD15+ Cells at Day 12 of CD34+ Cultures | pMON13288 | 44 | 42.4 | 72.2 | 48.8 | 54.5 |
| | pMON13288 + SCF | 36.1 | 32.2 | 63.5 | 24.5 | 47.1 |
| | native hIL-3 | 25.6 | 10.5 | 43.3 | 26 | 18.2 |
| | native hIL-3 + SCF | 17.7 | 11.5 | 55 | 12.4 | 24.2 |
| Percentage CD41+ | pMON13288 | 9.2 | 13.7 | 2.3 | 1.4 | 3.1 |

TABLE 4-continued

Ex-vivo Expansion

| Assay | Growth Factor | Donor #1 | Donor #2 | Donor #3 | Donor #4 | Donor #5 |
|---|---|---|---|---|---|---|
| Cells at Day 12 of CD34+ Cultures | pMON13288 + SCF | 16.1 | 9.1 | 6.6 | 4.5 | 5.6 |
| | native hIL-3 | 18.9 | 14.1 | 13.7 | 4.2 | 5.5 |
| | native hIL-3 + SCF | 15.3 | 10.7 | 12.9 | 7.4 | 15 |
| Total Number of Megakaryoctes (E + 05) In Day 10–12 Cultures | pMON13288 | 11 | 24 | 1.3 | 1 | 0.6 |
| | pMON13288 + SCF | 65 | 75 | 23 | 3.1 | 7.7 |
| | native hIL-3 | 6.8 | 2.3 | 5.9 | 0.2 | 0.3 |
| | native hIL-3 + SCF | 43 | 26 | 32 | 16 | 7.4 |
| Colony Forming Unit Granulocyte Macrophage (CFU-GM) Index | pMON13288 | 1.1 | 2.5 | 0.06 | 1 | 0.1 |
| | pMON13288 + SCF | 0.6 | 8.4 | 0.4 | 1 | 1.7 |
| | native hIL-3 | 0.2 | 0.06 | 0.03 | 0.03 | 0.03 |
| | native hIL-3 + SCF | 1.9 | 1.1 | 0.3 | 0.6 | 0.3 |
| Colony Forming Unit-Index | pMON13288 | 1.6 | 3.7 | 0.1 | 0.8 | 0.2 |
| | pMON13288 + SCF | 0.8 | 11.5 | 1.7 | 0.9 | 2.6 |
| | native hIL-3 | 0.2 | 0.1 | 0.03 | 0.03 | 0.04 |
| | native hIL-3 + SCF | 2.7 | 1.5 | 0.3 | 0.5 | 0.4 |

EXAMPLE 11

Ex vivo Expansion of CD34+ Cells from Bone Marrow Using p-MON13288 vs. Native IL-3 +/− G-CSF Cells were cultured as in Example 10 except CD34+ cells were isolated from normal bone marrow. Native IL-3, IL-3 variant (pMON13288) and G-CSF were used at 50 ng/mL of culture medium. Starting cell number for each treatment was 20× 10E4. The total cell expansion is shown in Table 5.

TABLE 5

| Treatment | Donor 1 | Donor 2 |
|---|---|---|
| native IL-3 | 42 × 10E4 | 169 × 10E4 |
| pMON13288 | 114 × 10E4 | 259 × 10E4 |
| G-CSF | 14 × 10E4 | 32 × 10E4 |
| pMON13288 and G-CSF | 194 × 10E4 | 609 × 10E4 |

Amino acids are shown herein by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Additional details may be found in co-pending U.S. patent application Ser. No. 08/411,795 which is hereby incorporated by reference in its entirety as if written herein.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

What is claimed is:

1. A method for ex vivo expansion of stem cells, comprising the steps of;
  (a) culturing said stem cells with a growth medium comprising;
    (I) a human interleukin-3 mutant polypeptide selected from the group consisting of:
      (i) a human interleukin-3 mutant polypeptide of (SEQ ID NO:1);
      wherein
        Xaa at position 17 is Ser, Lys, Gly, Asp, Met, Gln, or Arg;
        Xaa at position 18 is Asn, His, Leu, Ile, Phe, Arg, or Gln;
        Xaa at position 19 is Met, Phe, Ile, Arg, Gly, Ala, or Cys;
        Xaa at position 20 is Ile, Cys, Gln, Glu, Arg, Pro, or Ala;
        Xaa at position 21 is Asp, Phe, Lys, Arg, Ala, Gly, Glu, Gln, Asn, Thr, Ser or Val;
        Xaa at position 22 is Glu, Trp, Pro, Ser, Ala, His, Asp, Asn, Gln, Leu, Val or Gly;
        Xaa at position 23 is Ile, Val, Ala, Leu, Gly, Trp, Lys, Phe, Ser, or Arg;
        Xaa at position 24 is Ile, Gly, Val, Arg, Ser, Phe, or Leu;
        Xaa at position 25 is Thr, His, Gly, Gln, Arg, Pro, or Ala;
        Xaa at position 26 is His, Thr, Phe, Gly, Arg, Ala, or Trp;
        Xaa at position 27 is Leu, Gly, Arg, Thr, Ser, or Ala;
        Xaa at position 28 is Lys, Arg, Leu, Gln, Gly, Pro, Val or Trp;
        Xaa at position 29 is Gln, Asn, Leu, Pro, Arg, or Val;
        Xaa at position 30 is Pro, His, Thr, Gly, Asp, Gln, Ser, Leu, or Lys;
        Xaa at position 31 is Pro, Asp, Gly, Ala, Arg, Leu, or Gln;
        Xaa at position 32 is Leu, Val, Arg, Gln, Asn, Gly, Ala, or Glu;
        Xaa at position 33 is Pro, Leu, Gln, Ala, Thr, or Glu;
        Xaa at position 34 is Leu, Val, Gly, Ser, Lys, Glu, Gln, Thr, Arg, Ala, Phe, Ile or Met;
        Xaa at position 35 is Leu, Ala, Gly, Asn, Pro, Gln, or Val;
        Xaa at position 36 is Asp, Leu, or Val;
        Xaa at position 37 is Phe, Ser, Pro, Trp, or Ile;
        Xaa at position 38 is Asn, or Ala;
        Xaa at position 40 is Leu, Trp, or Arg;
        Xaa at position 41 is Asn, Cys, Arg, Leu, His, Met, or Pro;
        Xaa at position 42 is Gly, Asp, Ser, Cys, Asn, Lys, Thr, Leu, Val, Glu, Phe, Tyr, Ile, Met or Ala;
        Xaa at position 43 is Glu, Asn, Tyr, Leu, Phe, Asp, Ala, Cys, Gln, Arg, Thr, Gly or Ser;
        Xaa at position 44 is Asp, Ser, Leu, Arg, Lys, Thr, Met, Trp, Glu, Asn, Gln, Ala or Pro;
        Xaa at position 45 is Gln, Pro, Phe, Val, Met, Leu, Thr, Lys, Trp, Asp, Asn, Arg, Ser, Ala, Ile, Glu or His;
        Xaa at position 46 is Asp, Phe, Ser, Thr, Cys, Glu, Asn, Gln, Lys, His, Ala, Tyr, Ile, Val or Gly;
        Xaa at position 47 is Ile, Gly, Val, Ser, Arg, Pro, or His;
        Xaa at position 48 is Leu, Ser, Cys, Arg, Ile, His, Phe, Glu, Lys, Thr, Ala, Met, Val or Asn;
        Xaa at position 49 is Met, Arg, Ala, Gly, Pro, Asn, His, or Asp;
        Xaa at position 50 is Glu, Leu, Thr, Asp, Tyr, Lys, Asn, Ser, Ala, Ile, Val, His, Phe, Met or Gln;
        Xaa at position 51 is Asn, Arg, Met, Pro, Ser, Thr, or His;
        Xaa at position 52 is Asn, His, Arg, Leu, Gly, Ser, or Thr;
        Xaa at position 53 is Leu, Thr, Ala, Gly, Glu, Pro, Lys, Ser, or Met;
        Xaa at position 54 is Arg, Asp, Ile, Ser, Val, Thr, Gln, Asn, Lys, His, Ala or Leu;
        Xaa at position 55 is Arg, Thr, Val, Ser, Leu, or Gly;
        Xaa at position 56 is Pro, Gly, Cys, Ser, Gln, Glu, Arg, His, Thr, Ala, Tyr, Phe, Leu, Val or Lys;
        Xaa at position 57 is Asn or Gly;
        Xaa at position 58 is Leu, Ser, Asp, Arg, Gln, Val, or Cys;
        Xaa at position 59 is Glu, Tyr, His, Leu, Pro, or Arg;
        Xaa at position 60 is Ala, Ser, Pro, Tyr, Asn, or Thr;
        Xaa at position 61 is Phe, Asn, Glu, Pro, Lys, Arg, or Ser;
        Xaa at position 62 is Asn, His, Val, Arg, Pro, Thr, Asp, or Ile;
        Xaa at position 63 is Arg, Tyr, Trp, Ser, His, Pro, or Val;
        Xaa at position 64 is Ala, Asn, Pro, Ser, or Lys;
        Xaa at position 65 is Val, Thr, Pro, His, Leu, Phe, or Ser;
        Xaa at position 66 is Lys, Ile, Arg, Val, Asn, Glu, or Ser;
        Xaa at position 67 is Ser, Ala, Phe, Val, Gly, Asn, Ile, Pro, or His;
        Xaa at position 68 is Leu, Val, Trp, Ser, Ile, Phe, Thr, or His;
        Xaa at position 69 is Gln, Ala, Pro, Thr, Glu, Arg, Trp, Gly, or Leu;
        Xaa at position 70 is Asn, Leu, Val, Trp, Pro, or Ala;
        Xaa at position 71 is Ala, Met, Leu, Pro, Arg, Glu, Thr, Gln, Trp, or Asn;
        Xaa at position 72 is Ser, Glu, Met, Ala, His, Asn, Arg, or Asp;
        Xaa at position 73 is Ala, Glu, Asp, Leu, Ser, Gly, Thr, or Arg;
        Xaa at position 74 is Ile, Met, Thr, Pro, Arg, Gly, Ala;
        Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1-133) human interleukin-3, with the proviso that no more than one of the amino acids at positions 63, 82, 87, 98, 112, and 121 are different from the corresponding amino acids in native human interleukin-3; wherein from 1 to 14 amino acids are optionally deleted from the N-terminus and/or from 1 to 15 amino acids are optionally deleted from the C-terminus of said interleukin-3 mutant polypeptide; and wherein said interleukin-3 mutant polypeptide has increased activity relative to native human interleukin-3, in at least one assay selected from the group consisting of: AML cell proliferation, TF-1 cell proliferation and Methylcellulose assay; and (ii) a polypeptide comprising an N-terminal methionine residue, alanine residue or methionine-alanine di-peptide immediately preceding said sequence according to (i); and (II) a hematopoietic growth factor; and (b) harvesting said cultured stem cells.

2. A method for ex vivo expansion of stem cells, comprising the steps of;

(a) culturing said stem cells with a growth medium comprising;

(I) a human interleukin-3 mutant polypeptide selected from the group consisting of:

(i) a human interleukin-3 mutant polypeptide of (SEQ ID NO:4);

wherein

Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, Met, or;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1-133) human interleukin-3 with the proviso that no more than one of the amino acids at positions 49, 68, 73, 84, 98 and 107 are different from the corresponding amino acids in native human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and (ii) a polypeptide comprising an N-terminal methionine residue, alanine residue or methionine-alanine di-peptide immediately preceding said sequence according to (i); and
(II) a hematopoietic growth factor; and
(b) harvesting said cultured stem cells.

3. A method for ex vivo expansion of stem cells, comprising the steps of;
(a) culturing said stem cells with a growth medium comprising;
(I) a human interleukin-3 mutant polypeptide of (SEQ ID NO:7);
wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn, Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, or Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to about forty-four of the amino acids designated by Xaa are different from the corres ponding amino acids of native human interleukin-3; and wherein said interleukin-3 mutant olypeptide has increased activity relative to native human interleukin-3, in at least one assay selected from the group consisting of: AML cell proliferation, TF-1 cell proliferation and Methylcellulose assay; and
(II) a hematopoietic growth factor; and
(b) harvesting said cultured stem cells.

4. A method for ex vivo expansion of stem cells, comprising the steps of;
(a) culturing said stem cells with a growth medium comprising;
(I) a human interleukin-3 mutant polypeptide of (SEQ ID NO:8);
wherein; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 4 6 is Ala or Ser; Xaa at position 48 is Asn, Val or Pro ; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Gln; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to about forty-four of the amino acids designated by Xaa are different from the corresponding amino acids of native (15-125)human interleukin-3; and wherein said interleukin-3 mutant polypeptide has increased activity relative to native human interleukin-3, in at least one assay selected from the croup consisting of: AML cell proliferation, TF-1 cell proliferation and Methylcellulose assay; and (II) a hematopoietic growth factor; and (b) harvesting said cultured stem cells.

5. The method of claim 2, wherein said human interleukin-3 mutant polypeptide is selected from the group consisting of:

Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:9);

Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:10);

Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:11);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Leu Ala Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:12);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Glu Ser Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:13);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Thr Pro Asn Leu Leu Ala Phe Val Arg Ala Val Lys His Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:14);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Arg Lys Leu Thr Phe Tyr Leu Lys Thr Leu Glu Asn Ala Gln Ala Gln Gln (SEQ ID NO:15);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Arg Lys Leu Thr Phe Tyr Leu Lys Thr Leu Glu Asn Ala Gln Ala Gln Gln (SEQ ID NO:16);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Glu Lys Leu Thr Phe Tyr Leu Val Thr Leu Glu Gln Ala Gln Glu Gln Gln (SEQ ID NO:17);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Glu Lys Leu Thr Phe Tyr Leu Val Ser Leu Glu His Ala Gln Glu Gln Gln (SEQ ID NO:18);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn

Leu Arg Arg Pro Asn Leu Glu Ala Phe Asn Arg Ala Val
Lys Ser Leu Gln Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:19);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:20);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:21);

Asn Cys Ser Ile Met Ile Asp Glu Ile Ile His His Leu Lys
Arg Pro Pro Ala Pro Leu Leu Asp Pro Asn Asn Leu Asn
Ala Glu Asp Val Asp Ile Leu Met Glu Arg Asn Leu Arg
Leu Pro Asn Leu Glu Ser Phe Val Arg Ala Val Lys Asn
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:22);

Asn Cys Ser Ile Met Ile Asp Glu Ile Ile His His Leu Lys
Arg Pro Pro Asn Pro Leu Leu Asp Pro Asn Asn Leu Asn
Ser Glu Asp Met Asp Ile Leu Met Glu Arg Asn Leu Arg
Thr Pro Asn Leu Leu Ala Phe Val Arg Ala Val Lys His
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:23);

Asn Cys Ser Ile Met Ile Asp Glu Ile Ile His His Leu Lys
Val Pro Pro Ala Pro Leu Leu Asp Ser Asn Asn Leu Asn
Ser Glu Asp Met Asp Ile Leu Met Glu Arg Asn Leu Arg
Leu Pro Asn Leu Leu Ala Phe Val Arg Ala Val Lys Asn
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:24);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:25);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:26);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:27);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:28);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:29);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:30);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:31);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:32);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:33);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:34);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:35);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:36);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:37);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:38);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:39);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Ser Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:40);

Met Ala Asn Cys Ser Ile Met Ile Asp Glu Ala Ile His His
Leu Lys Arg Pro Pro Ala Pro Ser Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:41);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:42);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:43);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Val Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:44);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:45);

Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Ala Pro Leu Leu Asp Pro Asn Asn Leu
Asn Ala Glu Asp Val Asp Ile Leu Met Glu Arg Asn Leu
Arg Leu Pro Asn Leu Glu Ser Phe Val Arg Ala Val Lys
Asn Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:46); and Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Asn Pro Leu Leu Asp Pro Asn Asn Leu
Asn Ser Glu Asp Met Asp Ile Leu Met Glu Arg Asn Leu
Arg Thr Pro Asn Leu Leu Ala Phe Val Arg Ala Val Lys
His Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:47).

6. The method of claim 5, wherein said human interleukin-3 mutant polypeptide is selected from the group consisting of:

Met Ala Asn Cys Ser Ile Met Ile Asp Glu Leu Ile His His
Leu Lys Ile Pro Pro Asn Pro Ser Leu Asp Ser Ala Asn

Leu Asn Ser Glu Asp Val Ser Ile Leu Met Glu Arg Asn Leu Arg Thr Pro Asn Leu Leu Ala Phe Val Arg Ala Val Lys His Leu Glu Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln (SEQ ID NO:48) and a polypeptide comprising residues 2-113 of SEQ ID NO:48.

7. The method of claim 1, 2, 3, 4, 5 or 6 wherein said hematopoietic growth factor selected from the group consisting of GM-CSF, CSF-1, G-CSF, G-CSF Ser$^{17}$, c-mpl (ligand TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

8. The method of claim 7 wherein said hematopoietic growth factor selected from the group consisting of G-CSF, G-CSF Ser$^{17}$, c-mpl (ligand TPO), MGDF, and flt3 ligand.

9. The method of claim 1 wherein said mutant human interleukin-3 polypeptide has at least three times greater activity than native human interleukin-3, in at least one assay selected from the group consisting of: AML cell proliferation, TF-1 cell proliferation and Methylcellulose assay.

10. The method of claim 7 wherein said mutant human interleukin-3 polypeptide has at least three times greater activity than native human interleukin-3, in at least one assay selected from the group consisting of: AML cell proliferation, TF-1 cell proliferation and Methylcellulose assay.

11. The method of claim 1 further comprising the step of separating the stem cells from other cells prior to culturing the stem cells.

12. The method of claim 11 wherein said stem cells are separated from other cells based on the stem cells having CD34 surface antigen.

13. A method of enhancing the efficiency of the transduction of cultured stem cells by a heterologous gene, comprising the steps of;
(a) culturing said stem cells with a growth medium comprising;
(I) a human interleukin-3 mutant polypeptide selected from the group consisting of:
(i) a human interleukin-3 mutant polypeptide of (SEQ ID NO:1)
wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;

Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1-133) human interleukin-3 with the proviso that no more than one of the amino acids at positions 63, 82, 87, 98, 112, and 121 are different from the corresponding amino acids in native human interleukin-3; wherein from 1 to 14 amino acids are optionally deleted from the N-terminus and/or from 1 to 15 amino acids are optionally deleted from the C-terminus of said interleukin-3 mutant polypeptide; and wherein said interleukin-3 mutant polypeptide has increased activity relative to native human interleukin-3, in at least one assay selected from the group consisting of: AML cell proliferation, TF-1 cell proliferation and Methylcellulose assay; and (ii) a polypeptide comprising an N-terminal methionine residue, alanine residue or methionine-alanine di-peptide immediately preceding said sequence according to (i); and (II) a hematopoietic growth factor;
(b) transducing DNA into said cultured cells; and
(c) harvesting said transduced cells.

14. A method of enhancing the efficiency of the transduction of cultured stem cells by a heterologous gene, comprising the steps of;
(a) culturing said stem cells with a growth medium comprising;
(I) a human interleukin-3 mutant polypeptide selected from the group consisting of:
(i) a human interleukin-3 mutant polypeptide of (SEQ ID NO:4)
wherein
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, Met, or;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;

Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1-133) human interleukin-3 with the proviso that no more than one of the amino acids at positions 49, 68, 73, 84, 98 and 107 are different from the corresponding amino acids in native human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and
(ii) a polypeptide comprising an N-terminal methionine residue, alanine residue or methionine-alanine di-peptide immediately preceding said sequence according to (i); and
(II) a hematopoietic growth factor;
(b) transducing DNA into said cultured cells; and
(c) harvesting said transduced cells.

15. A method of enhancing the efficiency of the transduction of cultured stem cells by a heterologous, comprising the steps of;
(a) culturing said stem cells with a growth medium comprising a human interleukin-3 mutant polypeptide of (SEQ ID NO:7)
wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, or Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to about forty-four of the amino acids designated by Xaa are different from the corresponding amino acids of native human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and (II) a hematopoietic growth factor;

(b) transducing DNA into said cultured cells; and (c) harvesting said transduced cells.

16. A method of enhancing the efficiency of the transduction of cultured stem cells by a heterologous gene, comprising the steps of;

(a) culturing said stem cells with a growth medium comprising;

(I) a human interleukin-3 mutant polypeptide of (SEQ ID NO:8);

wherein; Xaa at position 4 is Asn or Ile; Xaa at position 5 is Met, Ala or Ile : Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Gln; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to about forty-four of the amino acids designated by Xaa are different from the corresponding amino acids of native (15-125)human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and (II) a hematopoietic growth factor;

(b) transducing DNA into said cultured cells; and (c) harvesting said transduced cells.

17. The method of claim 14, wherein said human interleukin-3 mutant polypeptide is selected from the group consisting of:

Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:9);

Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:10);

Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:11);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Leu Ala Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:12);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Glu Ser Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:13);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Thr Pro Asn Leu Leu Ala Phe Val Arg Ala Val Lys His Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:14);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Arg Lys Leu Thr Phe Tyr Leu Lys Thr Leu Glu Asn Ala Gln Ala Gln Gln (SEQ ID NO:15);

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn

Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Arg Lys Leu Thr Phe Tyr Leu Lys Thr Leu
Glu Asn Ala Gln Ala Gln Gln (SEQ ID NO:16);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Glu Lys Leu Thr Phe Tyr Leu Val Thr
Leu Glu Gln Ala Gln Glu Gln Gln (SEQ ID NO:17);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Glu Lys Leu Thr Phe Tyr Leu Val Ser
Leu Glu His Ala Gln Glu Gln Gln (SEQ ID NO:18);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:19);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:20);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:21);

Asn Cys Ser Ile Met Ile Asp Glu Ile Ile His His Leu Lys
Arg Pro Pro Ala Pro Leu Leu Asp Pro Asn Asn Leu Asn
Ala Glu Asp Val Asp Ile Leu Met Glu Arg Asn Leu Arg
Leu Pro Asn Leu Glu Ser Phe Val Arg Ala Val Lys Asn
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:22);

Asn Cys Ser Ile Met Ile Asp Glu Ile Ile His His Leu Lys
Arg Pro Pro Asn Pro Leu Leu Asp Pro Asn Asn Leu Asn
Ser Glu Asp Met Asp Ile Leu Met Glu Arg Asn Leu Arg
Thr Pro Asn Leu Leu Ala Phe Val Arg Ala Val Lys His
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:23);

Asn Cys Ser Ile Met Ile Asp Glu Ile Ile His His Leu Lys
Val Pro Pro Ala Pro Leu Leu Asp Ser Asn Asn Leu Asn
Ser Glu Asp Met Asp Ile Leu Met Glu Arg Asn Leu Arg
Leu Pro Asn Leu Leu Ala Phe Val Arg Ala Val Lys Asn
Leu Glu Asn Ala Ser Ala Ile Glu Ser Ile Leu Lys Asn
Leu Leu Pro Cys Leu Pro Leu Ala Thr Ala Ala Pro Thr
Arg His Pro Ile His Ile Lys Asp Gly Asp Trp Asn Glu
Phe Arg Arg Lys Leu Thr Phe Tyr Leu Lys Thr Leu Glu
Asn Ala Gln Ala Gln Gln (SEQ ID NO:24);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:25);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:26);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:27);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:28);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:29);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:30);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:31);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:32);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:33);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:34);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:35);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:36);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:37);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:38);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:39);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Ser Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:40);

Met Ala Asn Cys Ser Ile Met Ile Asp Glu Ala Ile His His
Leu Lys Arg Pro Pro Ala Pro Ser Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:41);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:42);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:43);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Val Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:44);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala

Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:45);
Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Ala Pro Leu Leu Asp Pro Asn Asn Leu
Asn Ala Glu Asp Val Asp Ile Leu Met Glu Arg Asn Leu
Arg Leu Pro Asn Leu Glu Ser Phe Val Arg Ala Val Lys
Asn Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:46); and
Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Asn Pro Leu Leu Asp Pro Asn Asn Leu
Asn Ser Glu Asp Met Asp Ile Leu Met Glu Arg Asn Leu
Arg Thr Pro Asn Leu Leu Ala Phe Val Arg Ala Val Lys
His Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:47).

18. The method of claim 17, wherein said human interleukin-3 mutant polypeptide is selected from the group consisting of: Met Ala Asn Cys Ser Ile Met Ile Asp Glu Leu Ile His His Leu Lys Ile Pro Pro Asn Pro Ser Leu Asp Ser Ala Asn Leu Asn Ser Glu Asp Val Ser Ile Leu Met Glu Arg Asn Leu Arg Thr Pro Asn Leu Leu Ala Phe Val Arg Ala Val Lys His Leu Glu Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln (SEQ ID NO:48) and
a polypeptide comprising residues 2–113 of SEQ ID NO:48.

19. The method of claim 13, 14, 15, 16, 17 or 18 wherein said hematopoietic growth factor selected from the group consisting of GM-CSF, CSF-1, G-CSF, G-CSF Ser$^{17}$, c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

20. The method of claim 19 wherein said hematopoietic growth factor selected from the group consisting of G-CSF, G-CSF Ser$^{17}$, c-mpl ligand (TPO), MGDF, and flt3 ligand.

21. The method of claim 13 wherein said mutant human interleukin-3 polypeptide has at least three times greater activity than native human interleukin-3, in at least one assay selected from the group consisting of: AML cell proliferation, TF-1 cell proliferation and Methylcellulose assay.

22. The method of claim 19 wherein said mutant human interleukin-3 polypeptide has at least three times greater activity than native human interleukin-3, in at least one assay selected from the group consisting of: AML cell proliferation, TF-1 cell proliferation and Methylcellulose assay.

23. The method of claim 13 further comprising the step of separating the stem cells from other cells prior to culturing the stem cells.

24. The method of claim 23 wherein said stem cells are separated from other cells based on the stem cells having CD34 surface antigen.

25. A method for treatment of a patient having a hematopoietic disorder, comprising the steps of;

(a) removing stem cells from said patient or a blood donor;
(b) culturing said stem cells with a growth medium comprising;
  (I) a human interleukin-3 mutant polypeptide selected from the group consisting of:
    (i) a human interleukin-3 mutant polypeptide of (SEQ ID NO:1);
    wherein
    Xaa at position 17 is Ser, Lys, Gly, Asp, Met, Gln, or Arg;
    Xaa at position 18 is Asn, His, Leu, Ile, Phe, Arg, or Gln;
    Xaa at position 19 is Met, Phe, Ile, Arg, Gly, Ala, or Cys;
    Xaa at position 20 is Ile, Cys, Gln, Glu, Arg, Pro, or Ala;
    Xaa at position 21 is Asp, Phe, Lys, Arg, Ala, Gly, Glu, Gln, Asn, Thr, Ser or Val;
    Xaa at position 22 is Glu, Trp, Pro, Ser, Ala, His, Asp, Asn, Gln, Leu, Val or Gly;
    Xaa at position 23 is Ile, Val, Ala, Leu, Gly, Trp, Lys, Phe, Ser, or Arg;
    Xaa at position 24 is Ile, Gly, Val, Arg, Ser, Phe, or Leu;
    Xaa at position 25 is Thr, His, Gly, Gln, Arg, Pro, or Ala;
    Xaa at position 26 is His, Thr, Phe, Gly, Arg, Ala, or Trp;
    Xaa at position 27 is Leu, Gly, Arg, Thr, Ser, or Ala;
    Xaa at position 28 is Lys, Arg, Leu, Gln, Gly, Pro, Val or Trp;
    Xaa at position 29 is Gln, Asn, Leu, Pro, Arg, or Val;
    Xaa at position 30 is Pro, His, Thr, Gly, Asp, Gln, Ser, Leu, or Lys;
    Xaa at position 31 is Pro, Asp, Gly, Ala, Arg, Leu, or Gln;
    Xaa at position 32 is Leu, Val, Arg, Gln, Asn, Gly, Ala, or Glu;
    Xaa at position 33 is Pro, Leu, Gln, Ala, Thr, or Glu;
    Xaa at position 34 is Leu, Val, Gly, Ser, Lys, Glu, Gln, Thr, Arg, Ala, Phe, Ile or Met;
    Xaa at position 35 is Leu, Ala, Gly, Asn, Pro, Gln, or Val;
    Xaa at position 36 is Asp, Leu, or Val;
    Xaa at position 37 is Phe, Ser, Pro, Trp, or Ile;
    Xaa at position 38 is Asn, or Ala;
    Xaa at position 40 is Leu, Trp, or Arg;
    Xaa at position 41 is Asn, Cys, Arg, Leu, His, Met, or Pro;
    Xaa at position 42 is Gly, Asp, Ser, Cys, Asn, Lys, Thr, Leu, Val, Glu, Phe, Tyr, Ile, Met or Ala;
    Xaa at position 43 is Glu, Asn, Tyr, Leu, Phe, Asp, Ala, Cys, Gln, Arg, Thr, Gly or Ser;
    Xaa at position 44 is Asp, Ser, Leu, Arg, Lys, Thr, Met, Trp, Glu, Asn, Gln, Ala or Pro;
    Xaa at position 45 is Gln, Pro, Phe, Val, Met, Leu, Thr, Lys, Trp, Asp, Asn, Arg, Ser, Ala, Ile, Glu or His;
    Xaa at position 46 is Asp, Phe, Ser, Thr, Cys, Glu, Asn, Gln, Lys, His, Ala, Tyr, Ile, Val or Gly;
    Xaa at position 47 is Ile, Gly, Val, Ser, Arg, Pro, or His;
    Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1-133) human interleukin-3 with the proviso that no more than one of the amino acids at positions 63, 82, 87, 98, 112, and 121 are different from the corresponding amino acids in native human interleukin-3; wherein from 1 to 14 amino acids are optionally deleted from the N-terminus and/or from 1 to 15 amino acids are optionally deleted from the C-terminus of said interleukin-3 mutant polypeptide; and wherein said interleukin-3 mutant polypeptide has increased activity relative to native human interleukin-3, in at least one assay selected from the group consisting of: AML cell proliferation, TF-1 cell proliferation and Methylcellulose assay; and (ii) a polypeptide comprising an N-terminal methionine residue, alanine residue or methionine-alanine di-peptide immediately preceding said sequence according to (i); and (II) a hematopoietic growth factor;

(c) harvesting said cultured stem cells; and (d) transplanting said cultured stem cells into said patient.

26. A method for treatment of a patient having a hematopoietic disorder, comprising the steps of;

(a) removing stem cells from said patient or a blood donor;

(b) culturing said stem cells with a growth medium comprising;

(I) a human interleukin-3 mutant polypeptide selected from the group consisting of:

(i) a human interleukin-3 mutant polypeptide of (SEQ ID NO:4)

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, Met, or;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Ser, His, Pro, or Val;

Xaa at position 50 is Ala, Asn, Pro, Ser, or Lys;

Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1-133) human interleukin-3, with the proviso that no more than one of the amino acids at positions 49, 68, 73, 84, 98 and 107 are different from the corresponding amino acids in native human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and (ii) a polypeptide comprising an N-terminal methionine residue, alanine residue or methionine-alanine di-peptide immediately preceding said sequence according to (i); and (II) a hematopoietic growth factor;

(c) harvesting said cultured stem cells; and (d) transplanting said cultured stem cells into said patient.

27. A method for treatment of a patient having a hematopoietic disorder, comprising the steps of;

(a) removing stem cells from said patient or a blood donor;
(b) culturing said stem cells with a [selected] growth medium comprising;
  (I) a human interleukin-3 mutant polypeptide of (SEQ ID NO:7);
    wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, or Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to about forty-four of the amino acids designated by Xaa are different from the corresponding amino acids of native human interleukin-3; and wherein said interleukin-3 mutant polypeptide has increased activity relative to native human interleukin-3, in at least one assay selected from the group consisting of: AML cell Proliferation, TF-1 cell proliferation and Methylcellulose assay; and
  (II) a hematopoietic growth factor;
(c) harvesting said cultured stem cells; and
(d) transplanting said cultured stem cells into said patient.

28. A method for treatment of a patient having a hematopoietic disorder, comprising the steps of;
(a) removing stem cells from said patient or a blood donor;
(b) culturing said stem cells with a growth medium comprising;
  (I) a human interleukin-3 mutant polypeptide of (SEQ ID NO:8);
    wherein Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Gln; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to about forty-four of the amino acids designated by Xaa are different from the corresponding amino acids of native (15-125)human interleukin-3; and wherein said interleukin-3 mutant polypeptide has increased activity relative to native human interleukin-3, in at least one assay selected from the group consisting of: AML cell proliferation, TF-1 cell proliferation and Methylcellulose assay; and
  (II) a hematopoietic growth factor;
(c) harvesting said cultured stem cells; and
(d) transplanting said cultured stem cells into said patient.

29. The method of claim 26, wherein said human interleukin-3 mutant polypeptide is selected from the group consisting of:

Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:9);

Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:10);

Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln (SEQ ID NO:11);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Arg Asn Leu
Arg Leu Pro Asn Leu Leu Ala Phe Val Arg Ala Val Lys
Asn Leu Glu Asn Ala Ser Ala Ile Glu Ser Ile Leu Lys
Asn Leu Leu Pro Cys Leu Pro Leu Ala Thr Ala Ala Pro
Thr Arg His Pro Ile His Ile Lys Asp Gly Asp Trp Asn
Glu Phe Arg Arg Lys Leu Thr Phe Tyr Leu Lys Thr Leu
Glu Asn Ala Gln Ala Gln Gln (SEQ ID NO:12);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Arg Asn Leu
Arg Leu Pro Asn Leu Glu Ser Phe Val Arg Ala Val Lys
Asn Leu Glu Asn Ala Ser Ala Ile Glu Ser Ile Leu Lys
Asn Leu Leu Pro Cys Leu Pro Leu Ala Thr Ala Ala Pro
Thr Arg His Pro Ile His Ile Lys Asp Gly Asp Trp Asn
Glu Phe Arg Arg Lys Leu Thr Phe Tyr Leu Lys Thr Leu
Glu Asn Ala Gln Ala Gln Gln (SEQ ID NO:13);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Arg Asn Leu
Arg Thr Pro Asn Leu Leu Ala Phe Val Arg Ala Val Lys
His Leu Glu Asn Ala Ser Ala Ile Glu Ser Ile Leu Lys
Asn Leu Leu Pro Cys Leu Pro Leu Ala Thr Ala Ala Pro
Thr Arg His Pro Ile His Ile Lys Asp Gly Asp Trp Asn
Glu Phe Arg Arg Lys Leu Thr Phe Tyr Leu Lys Thr Leu
Glu Asn Ala Gln Ala Gln Gln (SEQ ID NO:14);

Asn Cys Ser Asn Met Ile Asp Glu Ile Ile Thr His Leu Lys
Gln Pro Pro Leu Pro Leu Leu Asp Phe Asn Asn Leu
Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Lys Leu Thr Phe Tyr Leu Lys Thr Leu

Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:26);

Met Ala Asn Cys Ser Asn Met Ile Asp Glu Ile Ile Thr His
Leu Lys Gln Pro Pro Leu Pro Leu Leu Asp Phe Asn Asn
Leu Asn Gly Glu Asp Gln Asp Ile Leu Met Glu Asn Asn
Leu Arg Arg Pro Asn Leu Glu Ala Phe Asn Arg Ala Val
Lys Ser Leu Gln Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:27);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:28);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:29);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Ala Ile Glu Ser Ile Leu
Lys Asn Leu Leu Pro Cys Leu Pro Leu Ala Thr Ala Ala
Pro Thr Arg His Pro Ile His Ile Lys Asp Gly Asp Trp
Asn Glu Phe Arg Arg Lys Leu Thr Phe Tyr Leu Lys Thr
Leu Glu Asn Ala Gln Ala Gln Gln (SEQ ID NO:30);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:31);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:32);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:33);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:34);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:35);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:36);

Met Ala Asn Cys Ser Ile Met Ile Asp Glu Ile Ile His His
Leu Lys Val Pro Pro Ala Pro Leu Leu Asp Ser Asn Asn
Leu Asn Ser Glu Asp Met Asp Ile Leu Met Glu Arg Asn
Leu Arg Leu Pro Asn Leu Leu Ala Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:37);

Met Ala Asn Cys Ser Ile Met Ile Asp Glu Ile Ile His His
Leu Lys Arg Pro Pro Asn Pro Leu Leu Asp Pro Asn Asn
Leu Asn Ser Glu Asp Met Asp Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:38);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Val Pro Cys Leu Pro Ser Ala Thr Ala Ala
Pro Ser Arg His Pro Ile Thr Ile Lys Ala Gly Asp Trp Gln
Glu Phe Arg Glu Lys Leu Thr Phe Tyr Leu Val Ser Leu
Glu His Ala Gln Glu Gln Gln (SEQ ID NO:39);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Ser Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:40);

Met Ala Asn Cys Ser Ile Met Ile Asp Glu Ala Ile His His
Leu Lys Arg Pro Pro Ala Pro Ser Leu Asp Pro Asn Asn
Leu Asn Asp Glu Asp Met Ser Ile Leu Met Glu Arg Asn

Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:41);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:42);

Met Ala Asn Cys Ser Ile Met Ile Asp Glu Ile Ile His His
Leu Lys Arg Pro Pro Ala Pro Leu Leu Asp Pro Asn Asn
Leu Asn Ala Glu Asp Val Asp Ile Leu Met Asp Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:43);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Val Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:44);

Met Ala Asn Cys Ser Ile Met Ile Asp Glu Ile Ile His His
Leu Lys Arg Pro Pro Ala Pro Leu Leu Asp Pro Asn Asn
Leu Asn Asp Glu Asp Met Ser Ile Leu Met Glu Arg Asn
Leu Arg Leu Pro Asn Leu Glu Ser Phe Val Arg Ala Val
Lys Asn Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:45);

Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Ala Pro Leu Leu Asp Pro Asn Asn Leu
Asn Ala Glu Asp Val Asp Ile Leu Met Glu Arg Asn Leu
Arg Leu Pro Asn Leu Glu Ser Phe Val Arg Ala Val Lys
Asn Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:46); and Met Ala Tyr Pro Glu Thr Asp Tyr Lys Asp Asp Asp Asp
Lys Asn Cys Ser Ile Met Ile Asp Glu Ile Ile His His Leu
Lys Arg Pro Pro Asn Pro Leu Leu Asp Pro Asn Asn Leu
Asn Ser Glu Asp Met Asp Ile Leu Met Glu Arg Asn Leu
Arg Thr Pro Asn Leu Leu Ala Phe Val Arg Ala Val Lys
His Leu Glu Asn Ala Ser Gly Ile Glu Ala Ile Leu Arg
Asn Leu Gln Pro Cys Leu Pro Ser Ala Thr Ala Ala Pro
Ser Arg His Pro Ile Ile Ile Lys Ala Gly Asp Trp Gln Glu
Phe Arg Glu Lys Leu Thr Phe Tyr Leu Val Thr Leu Glu
Gln Ala Gln Glu Gln Gln (SEQ ID NO:47).

30. The method of claim 29, wherein said human interleukin-3 mutant polypeptide is selected from the group consisting of:

Met Ala Asn Cys Ser Ile Met Ile Asp Glu Leu Ile His His
Leu Lys Ile Pro Pro Asn Pro Ser Leu Asp Ser Ala Asn
Leu Asn Ser Glu Asp Val Ser Ile Leu Met Glu Arg Asn
Leu Arg Thr Pro Asn Leu Leu Ala Phe Val Arg Ala Val
Lys His Leu Glu Asn Ala Ser Gly Ile Glu Ala Ile Leu
Arg Asn Leu Gln Pro Cys Leu Pro Ser Ala Thr Ala Ala
Pro Ser Arg His Pro Ile Ile Ile Lys Ala Gly Asp Trp Gln
Glu Phe Arg Glu Lys Leu Thr Phe Tyr Leu Val Thr Leu
Glu Gln Ala Gln Glu Gln Gln (SEQ ID NO:48) and a polypeptide comprising residues 2–113 of SEQ ID NO:48.

31. The method of claim 25, 26, 27, 28, 29 or 30 wherein said hematopoietic growth factor selected from the group consisting of GM-CSF, CSF-1, G-CSF, G-CSF Ser$^{17}$, c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

32. The method of claim 31 wherein said hematopoietic growth factor selected from the group consisting of G-CSF, G-CSF Ser$^{17}$, c-mpl ligand (TPO), MGDF, and flt3 ligand.

33. The method of claim 25 wherein said mutant human interleukin-3 polypeptide has at least three times greater activity than native human interleukin-3, in at least one assay selected from the group consisting of: AML cell proliferation, TF-1 cell proliferation and Methylcellulose assay.

34. The method of claim 25 further comprising the step of separating the stem cells from other cells prior to culturing the stem cells.

35. The method of claim 34 wherein said stem cells are separated from other cells based on the stem cells having CD34 surface antigen.

\* \* \* \* \*

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
      (A) LENGTH: 133 amino acids
      (B) TYPE: amino acid
      (D) TOPOLOGY: linear

```
(ii) MOLECULE TYPE: peptide (ix) FEATURE:
    (A) NAME/KEY: Modified-site
    (B) LOCATION: 1
    (D) OTHER INFORMATION: /note= "Met- may or may not precede the
        amino acid in position 1"

(ix) FEATURE:
    (A) NAME/KEY: Modified-site
    (B) LOCATION: 17
    (D) OTHER INFORMATION: /note= "Xaa at position 17 is Ser,
        Lys, Gly, Asp, Met, Gln, or Arg"

(ix) FEATURE:
    (A) NAME/KEY: Modified-site
    (B) LOCATION: 18
    (D) OTHER INFORMATION: /note= "Xaa at position 18 is Asn,
        His, Leu, Ile, Phe, Arg, or Gln"

(ix) FEATURE:
    (A) NAME/KEY: Modified-site
    (B) LOCATION: 19
    (D) OTHER INFORMATION: /note= "Xaa at positiion 19 is Met,
        Phe, Ile, Arg, Gly, Ala, or Cys"

(ix) FEATURE:
    (A) NAME/KEY: Modified-site
    (B) LOCATION: 20
    (D) OTHER INFORMATION: /note= "Xaa at position 20 is Ile,
        Cys, Gln, Glu, Arg, Pro, or Ala"

(ix) FEATURE:
    (A) NAME/KEY: Modified-site
    (B) LOCATION: 21
    (D) OTHER INFORMATION: /note= "Xaa at position 21 is Asp,
        Phe, Lys, Arg, Ala, Gly, Glu, Gln, Asn, Thr, Ser,
        or Val"

(ix) FEATURE:
    (A) NAME/KEY: Modified-site
    (B) LOCATION: 22
    (D) OTHER INFORMATION: /note= "Xaa at position 22 is Glu,
        Trp, Pro, Ser, Ala, His, Asp, Asn, Gln, Leu, Val,
        or Gly"

(ix) FEATURE:
    (A) NAME/KEY: Modified-site
    (B) LOCATION: 23
    (D) OTHER INFORMATION: /note= "Xaa at position 23 is Ile,
        Val, Ala, Leu, Gly, Trp, Lys, Phe, Ser, or
        Arg"

(ix) FEATURE:
    (A) NAME/KEY: Modified-site
    (B) LOCATION: 24
    (D) OTHER INFORMATION: /note= "Xaa at position 24 is Ile,
        Gly, Val, Arg, Ser, Phe, or Leu"

(ix) FEATURE:
    (A) NAME/KEY: Modified-site
    (B) LOCATION: 25
    (D) OTHER INFORMATION: /note= "Xaa at position 25 is Thr,
        His, Gly, Gln, Arg, Pro, or Ala"

(ix) FEATURE:
    (A) NAME/KEY: Modified-site
    (B) LOCATION: 26
    (D) OTHER INFORMATION: /note= "Xaa at position 26 is His,
        Thr, Phe, Gly, Arg, Ala, or Trp"

(ix) FEATURE:
    (A) NAME/KEY: Modified-site
    (B) LOCATION: 27
    (D) OTHER INFORMATION: /note= "Xaa at position 27 is Leu,
        Gly, Arg, Thr, Ser, or Ala"

(ix) FEATURE:
```

(A) NAME/KEY: Modified-site
              (B) LOCATION: 28
              (D) OTHER INFORMATION: /note= "Xaa at position 28 is Lys,
                  Arg, Leu, Gln, Gly, Pro, Val, or Trp"

(ix) FEATURE:
              (A) NAME/KEY: Modified-site
              (B) LOCATION: 29
              (D) OTHER INFORMATION: /note= "Xaa at position 29 is Gln,
                  Asn, Leu, Pro, Arg, or Val"

(ix) FEATURE:
              (A) NAME/KEY: Modified-site
              (B) LOCATION: 30
              (D) OTHER INFORMATION: /note= "Xaa at position 30 is Pro,
                  His, Thr, Gly, Asp, Gln, Ser, Leu, or Lys"

(ix) FEATURE:
              (A) NAME/KEY: Modified-site
              (B) LOCATION: 31
              (D) OTHER INFORMATION: /note= "Xaa at position 31 is Pro,
                  Asp, Gly, Ala, Arg, Leu, or Gln"

(ix) FEATURE:
              (A) NAME/KEY: Modified-site
              (B) LOCATION: 32
              (D) OTHER INFORMATION: /note= "Xaa at position 32 is Leu,
                  Val, Arg, Gln, Asn, Gly, Ala, or Glu"

(ix) FEATURE:
              (A) NAME/KEY: Modified-site
              (B) LOCATION: 33
              (D) OTHER INFORMATION: /note= "Xaa at position 33 is Pro,
                  Leu, Gln, Ala, Thr, or Glu"

(ix) FEATURE:
              (A) NAME/KEY: Modified-site
              (B) LOCATION: 34
              (D) OTHER INFORMATION: /note= "Xaa at position 34 is Leu,
                  Val, Gly, Ser, Lys, Glu, Gln, Thr, Arg, Ala, Phe,
                  Ile, or Met"

(ix) FEATURE:
              (A) NAME/KEY: Modified-site
              (B) LOCATION: 35
              (D) OTHER INFORMATION: /note= "Xaa at position 35 is Leu,
                  Ala, Gly, Asn, Pro, Gln, or Val"

(ix) FEATURE:
              (A) NAME/KEY: Modified-site
              (B) LOCATION: 36
              (D) OTHER INFORMATION: /note= "Xaa at position 36 is Asp,
                  Leu, or Val"

(ix) FEATURE:
              (A) NAME/KEY: Modified-site
              (B) LOCATION: 37
              (D) OTHER INFORMATION: /note= "Xaa at position 37 is Phe,
                  Ser, Pro, Trp, or Ile"

(ix) FEATURE:
              (A) NAME/KEY: Modified-site
              (B) LOCATION: 38
              (D) OTHER INFORMATION: /note= "Xaa at position 38 is Asn,
                  or Ala"

(ix) FEATURE:
              (A) NAME/KEY: Modified-site
              (B) LOCATION: 40
              (D) OTHER INFORMATION: /note= "Xaa at position 40 is Leu,
                  Trp, or Arg"

(ix) FEATURE:
              (A) NAME/KEY: Modified-site
              (B) LOCATION: 41
              (D) OTHER INFORMATION: /note= "Xaa at position 41 is Asn,
                  Cys, Arg, Leu, His, Met, or Pro"

(ix) FEATURE:

```
            (A) NAME/KEY: Modified-site
            (B) LOCATION: 42
            (D) OTHER INFORMATION: /note= "Xaa at position 42 is Gly,
                Asp, Ser, Cys, Asn, Lys, Thr, Leu, Val, Glu, Phe, Tyr,
                Ile, Met, or Ala"

(ix) FEATURE:
            (A) NAME/KEY: Modified-site
            (B) LOCATION: 43
            (D) OTHER INFORMATION: /note= "Xaa at position 43 is Glu,
                Asn, Tyr, Leu, Phe, Asp, Ala, Cys, Gln, Arg, Thr, Gly,
                or Ser"

(ix) FEATURE:
            (A) NAME/KEY: Modified-site
            (B) LOCATION: 44
            (D) OTHER INFORMATION: /note= "Xaa at position 44 is Asp,
                Ser, Leu, Arg, Lys, Thr, Met, Trp, Glu, Asn, Gln, Ala,
                or Pro"

(ix) FEATURE:
            (A) NAME/KEY: Modified-site
            (B) LOCATION: 45
            (D) OTHER INFORMATION: /note= "Xaa at position 45 is Gln,
                Pro, Phe, Val, Met, Leu, Thr, Lys, Trp, Asp, Asn, Arg,
                Ser, Ala, Ile, Glu, or His"

(ix) FEATURE:
            (A) NAME/KEY: Modified-site
            (B) LOCATION: 46
            (D) OTHER INFORMATION: /note= "Xaa at position 46 is Asp,
                Phe, Ser, Thr, Cys, Glu, Asn, Gln, Lys, His, Ala, Tyr,
                Ile, Val, or Gly"

(ix) FEATURE:
            (A) NAME/KEY: Modified-site
            (B) LOCATION: 47
            (D) OTHER INFORMATION: /note= "Xaa at position 47 is Ile,
                Gly, Val, Ser, Arg, Pro, or His"

(ix) FEATURE:
            (A) NAME/KEY: Modified-site
            (B) LOCATION: 48
            (D) OTHER INFORMATION: /note= "Xaa at position 48 is Leu,
                Ser, Cys, Arg, Ile, His, Phe, Glu, Lys, Thr, Ala, Met,
                Val, or Asn"

(ix) FEATURE:
            (A) NAME/KEY: Modified-site
            (B) LOCATION: 49
            (D) OTHER INFORMATION: /note= "Xaa at position 49 is Met,
                Arg, Ala, Gly, Pro, Asn, His, or Asp"

(ix) FEATURE:
            (A) NAME/KEY: Modified-site
            (B) LOCATION: 50
            (D) OTHER INFORMATION: /note= "Xaa at position 50 is Glu,
                Leu, Thr, Asp, Tyr, Lys, Asn, Ser, Ala, Ile, Val, His,
                Phe, Met, or Gln"

(ix) FEATURE:
            (A) NAME/KEY: Modified-site
            (B) LOCATION: 51
            (D) OTHER INFORMATION: /note= "Xaa at position 51 is Asn,
                Arg, Met, Pro, Ser, Thr, or His"

(ix) FEATURE:
            (A) NAME/KEY: Modified-site
            (B) LOCATION: 52
            (D) OTHER INFORMATION: /note= "Xaa at position 52 is Asn,
                His, Arg, Leu, Gly, Ser, or Thr"

(ix) FEATURE:
            (A) NAME/KEY: Modified-site
            (B) LOCATION: 53
            (D) OTHER INFORMATION: /note= "Xaa at position 53 is
                Leu, Thr, Ala, Gly, Glu, Pro, Lys, Ser, or Met"

(ix) FEATURE:
```

```
          (A) NAME/KEY: Modified-site
          (B) LOCATION: 54
          (D) OTHER INFORMATION: /note= "Xaa at position 54 is Arg,
              Asp, Ile, Ser, Val, Thr, Gln, Asn, Lys, His, Ala,
              or Leu"

(ix) FEATURE:
          (A) NAME/KEY: Modified-site
          (B) LOCATION: 55
          (D) OTHER INFORMATION: /note= "Xaa at position 55 is Arg,
              Thr, Val, Ser, Leu, or Gly"

(ix) FEATURE:
          (A) NAME/KEY: Modified-site
          (B) LOCATION: 56
          (D) OTHER INFORMATION: /note= "Xaa at position 56 is Pro,
              Gly, Cys, Ser, Gln, Glu, Arg, His, Thr, Ala, Tyr,
              Phe, Leu, Val, or Lys"

(ix) FEATURE:
          (A) NAME/KEY: Modified-site
          (B) LOCATION: 57
          (D) OTHER INFORMATION: /note= "Xaa at position 57 is Asn
              or Gly"

(ix) FEATURE:
          (A) NAME/KEY: Modified-site
          (B) LOCATION: 58
          (D) OTHER INFORMATION: /note= "Xaa at position 58 is Leu,
              Ser, Asp, Arg, Gln, Val, or Cys"

(ix) FEATURE:
          (A) NAME/KEY: Modified-site
          (B) LOCATION: 59
          (D) OTHER INFORMATION: /note= "Xaa at position 59 is Glu,
              Tyr, His, Leu, Pro, or Arg"

(ix) FEATURE:
          (A) NAME/KEY: Modified-site
          (B) LOCATION: 60
          (D) OTHER INFORMATION: /note= "Xaa at position 60 is Ala,
              Ser, Pro, Tyr, Asn, or Thr"

(ix) FEATURE:
          (A) NAME/KEY: Modified-site
          (B) LOCATION: 61
          (D) OTHER INFORMATION: /note= "Xaa at position 61 is Phe,
              Asn, Glu, Pro, Lys, Arg, or Ser"

(ix) FEATURE:
          (A) NAME/KEY: Modified-site
          (B) LOCATION: 62
          (D) OTHER INFORMATION: /note= "Xaa at position 62 is Asn,
              His, Val, Arg, Pro, Thr, Asp, or Ile"

(ix) FEATURE:
          (A) NAME/KEY: Modified-site
          (B) LOCATION: 63
          (D) OTHER INFORMATION: /note= "Xaa at position 63 is Arg,
              Tyr, Trp, Lys, Ser, His, Pro, or Val"

(ix) FEATURE:
          (A) NAME/KEY: Modified-site
          (B) LOCATION: 64
          (D) OTHER INFORMATION: /note= "Xaa at position 64 is Ala,
              Asn, Pro, Ser, or Lys"

(ix) FEATURE:
          (A) NAME/KEY: Modified-site
          (B) LOCATION: 65
          (D) OTHER INFORMATION: /note= "Xaa at position 65 is Val,
              Thr, Pro, His, Leu, Phe, or Ser"

(ix) FEATURE:
          (A) NAME/KEY: Modified-site
          (B) LOCATION: 66
          (D) OTHER INFORMATION: /note= "Xaa at position 66 is Lys,
              Ile, Arg, Val, Asn, Glu, or Ser"
```

-continued

```
(ix) FEATURE:
    (A) NAME/KEY: Modified-site
    (B) LOCATION: 67
    (D) OTHER INFORMATION: /note= "Xaa at position 67 is Ser,
        Ala, Phe, Val, Gly, Asn, Ile, Pro, or His"

(ix) FEATURE:
    (A) NAME/KEY: Modified-site
    (B) LOCATION: 68
    (D) OTHER INFORMATION: /note= "Xaa at position 68 is Leu,
        Val, Trp, Ser, Ile, Phe, Thr, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, Trp, Gly, or Leu"

(ix) FEATURE:
    (A) NAME/KEY: Modified-site
    (B) LOCATION: 70
    (D) OTHER INFORMATION: /note= "Xaa at position 70 is Asn,
        Leu, Val, Trp, Pro, or Ala"

(ix) FEATURE:
    (A) NAME/KEY: Modified-site
    (B) LOCATION: 71
    (D) OTHER INFORMATION: /note= "Xaa at position 71 is
        Ala, Met, Leu, Pro, Arg, Glu, Thr, Gln, Trp,
        or Asn"

(ix) FEATURE:
    (A) NAME/KEY: Modified-site
    (B) LOCATION: 72
    (D) OTHER INFORMATION: /note= "Xaa at position 72 is Ser,
        Glu, Met, Ala, His, Asn, Arg, or Asp"

(ix) FEATURE:
    (A) NAME/KEY: Modified-site
    (B) LOCATION: 73
    (D) OTHER INFORMATION: /note= "Xaa at position 73 is Ala,
        Glu, Asp, Leu, Ser, Gly, Thr, or Arg"

(ix) FEATURE:
    (A) NAME/KEY: Modified-site
    (B) LOCATION: 74
    (D) OTHER INFORMATION: /note= "Xaa at position 74 is Ile,
        Met, Thr, Pro, Arg, Gly, or Ala"

(ix) FEATURE:
    (A) NAME/KEY: Modified-site
    (B) LOCATION: 75
    (D) OTHER INFORMATION: /note= "Xaa at position 75 is
        Glu, Lys, Gly, Asp, Pro, Trp, Arg, Ser, Gln,
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Trp, Glu, Pro, Gly, or Asp"

(ix) FEATURE:
    (A) NAME/KEY: Modified-site
    (B) LOCATION: 77
    (D) OTHER INFORMATION: /note= "Xaa at position 77 is Ile,
        Ser, Arg, Thr, or Leu"

(ix) FEATURE:
    (A) NAME/KEY: Modified-site
    (B) LOCATION: 78
    (D) OTHER INFORMATION: /note= "Xaa at position 78 is Leu,
        Ala, Ser, Glu, Phe, Gly, or Arg"

(ix) FEATURE:
    (A) NAME/KEY: Modified-site
    (B) LOCATION: 79
    (D) OTHER INFORMATION: /note= "Xaa at position 79 is Lys, Thr,
        Asn, Met, Arg, Ile, Gly, or Asp"
```

```
(ix) FEATURE:
      (A) NAME/KEY: Modified-site
      (B) LOCATION: 80
      (D) OTHER INFORMATION: /note= "Xaa at position 80 is Asn,
          Trp, Val, Gly, Thr, Leu, Glu, or Arg"

(ix) FEATURE:
      (A) NAME/KEY: Modified-site
      (B) LOCATION: 81
      (D) OTHER INFORMATION: /note= "Xaa at position 81 is Leu,
          Gln, Gly, Ala, Trp, Arg, Val, or Lys"

(ix) FEATURE:
      (A) NAME/KEY: Modified-site
      (B) LOCATION: 82
      (D) OTHER INFORMATION: /note= "Xaa at position 82 is Leu,
          Gln, Lys, Trp, Arg, Asp, Glu, Asn, His, Thr, Ser, Ala,
          Tyr, Phe, Ile, Met, or Val"

(ix) FEATURE:
      (A) NAME/KEY: Modified-site
      (B) LOCATION: 83
      (D) OTHER INFORMATION: /note= "Xaa at position 83 is Pro,
          Ala, Thr, Trp, Arg, or Met"

(ix) FEATURE:
      (A) NAME/KEY: Modified-site
      (B) LOCATION: 84
      (D) OTHER INFORMATION: /note= "Xaa at position 84 is Cys,
          Glu, Gly, Arg, Met, or Val"

(ix) FEATURE:
      (A) NAME/KEY: Modified-site
      (B) LOCATION: 85
      (D) OTHER INFORMATION: /note= "Xaa at position 85 is Leu,
          Asn, Val, or Gln"

(ix) FEATURE:
      (A) NAME/KEY: Modified-site
      (B) LOCATION: 86
      (D) OTHER INFORMATION: /note= "Xaa at position 86 is Pro,
          Cys, Arg, Ala, or Lys"

(ix) FEATURE:
      (A) NAME/KEY: Modified-site
      (B) LOCATION: 87
      (D) OTHER INFORMATION: /note= "Xaa at position 87 is Leu,
          Ser, Trp, or Gly"

(ix) FEATURE:
      (A) NAME/KEY: Modified-site
      (B) LOCATION: 88
      (D) OTHER INFORMATION: /note= "Xaa at position 88 is Ala,
          Lys, Arg, Val, or Trp"

(ix) FEATURE:
      (A) NAME/KEY: Modified-site
      (B) LOCATION: 89
      (D) OTHER INFORMATION: /note= "Xaa at position 89 is Thr,
          Asp, Cys, Leu, Val, Glu, His, Asn, or Ser"

(ix) FEATURE:
      (A) NAME/KEY: Modified-site
      (B) LOCATION: 90
      (D) OTHER INFORMATION: /note= "Xaa at position 90 is Ala,
          Pro, Ser, Thr, Gly, Asp, Ile, or Met"

(ix) FEATURE:
      (A) NAME/KEY: Modified-site
      (B) LOCATION: 91
      (D) OTHER INFORMATION: /note= "Xaa at position 91 is Ala,
          Pro, Ser, Thr, Phe, Leu, Asp, or His"

(ix) FEATURE:
      (A) NAME/KEY: Modified-site
      (B) LOCATION: 92
      (D) OTHER INFORMATION: /note= "Xaa at position 92 is Pro,
          Phe, Arg, Ser, Lys, His, Ala, Gly, Ile, or Leu"
```

```
(ix) FEATURE:
    (A) NAME/KEY: Modified-site
    (B) LOCATION: 93
    (D) OTHER INFORMATION: /note= "Xaa at position 93 is Thr,
        Asp, Ser, Asn, Pro, Ala, Leu, or Arg"

(ix) FEATURE:
    (A) NAME/KEY: Modified-site
    (B) LOCATION: 94
    (D) OTHER INFORMATION: /note= "Xaa at position 94 is Arg,
        Ile, Ser, Glu, Leu, Val, Gln, Lys, His, Ala, or Pro"

(ix) FEATURE:
    (A) NAME/KEY: Modified-site
    (B) LOCATION: 95
    (D) OTHER INFORMATION: /note= "Xaa at position 95 is His,
        Gln, Pro, Arg, Val, Leu, Gly, Thr, Asn, Lys, Ser, Ala,
        Trp, Phe, Ile, or Tyr"

(ix) FEATURE:
    (A) NAME/KEY: Modified-site
    (B) LOCATION: 96
    (D) OTHER INFORMATION: /note= "Xaa at position 96 is Pro,
        Lys, Tyr, Gly, Ile, or Thr"

(ix) FEATURE:
    (A) NAME/KEY: Modified-site
    (B) LOCATION: 97
    (D) OTHER INFORMATION: /note= "Xaa at position 97 is Ile,
        Val, Lys, Ala, or Asn"

(ix) FEATURE:
    (A) NAME/KEY: Modified-site
    (B) LOCATION: 98
    (D) OTHER INFORMATION: /note= "Xaa at position 98 is His,
        Ile, Asn, Leu, Asp, Ala, Thr, Glu, Gln, Ser, Phe, Met,
        Val, Lys, Arg, Tyr, or Pro"

(ix) FEATURE:
    (A) NAME/KEY: Modified-site
    (B) LOCATION: 99
    (D) OTHER INFORMATION: /note= "Xaa at position 99 is Ile,
        Leu, Arg, Asp, Val, Pro, Gln, Gly, Ser, Phe,
        or His"

(ix) FEATURE:
    (A) NAME/KEY: Modified-site
    (B) LOCATION: 100
    (D) OTHER INFORMATION: /note= "Xaa at position 100 is
        Lys, Tyr, Leu, His, Arg, Ile, Ser, Gln, or Pro"

(ix) FEATURE:
    (A) NAME/KEY: Modified-site
    (B) LOCATION: 101
    (D) OTHER INFORMATION: /note= "Xaa at position 101 is
        Asp, Pro, Met, Lys, His, Thr, Val, Tyr, Glu, Asn, Ser,
        Ala, Gly, Ile, Leu, or Gln"

(ix) FEATURE:
    (A) NAME/KEY: Modified-site
    (B) LOCATION: 102
    (D) OTHER INFORMATION: /note= "Xaa at position 102 is Gly,
        Leu, Glu, Lys, Ser, Tyr, or Pro"

(ix) FEATURE:
    (A) NAME/KEY: Modified-site
    (B) LOCATION: 103
    (D) OTHER INFORMATION: /note= "Xaa at position 103 is Asp,
        or Ser"

(ix) FEATURE:
    (A) NAME/KEY: Modified-site
    (B) LOCATION: 104
    (D) OTHER INFORMATION: /note= "Xaa at position 104 is
        Trp, Val, Cys, Tyr, Thr, Met, Pro, Leu, Gln, Lys, Ala,
        Phe, or Gly"

(ix) FEATURE:
```

(A) NAME/KEY: Modified-site
          (B) LOCATION: 105
          (D) OTHER INFORMATION: /note= "Xaa at position 105 is
              Asn, Pro, Ala, Phe, Ser, Trp, Gln, Tyr, Leu, Lys, Ile,
              Asp, or His"

(ix) FEATURE:
          (A) NAME/KEY: Modified-site
          (B) LOCATION: 106
          (D) OTHER INFORMATION: /note= "Xaa at position 106 is Glu,
              Ser, Ala, Lys, Thr, Ile, Gly, or Pro"

(ix) FEATURE:
          (A) NAME/KEY: Modified-site
          (B) LOCATION: 108
          (D) OTHER INFORMATION: /note= "Xaa at position 108 is Arg,
              Lys, Asp, Leu, Thr, Ile, Gln, His, Ser, Ala, or Pro"

(ix) FEATURE:
          (A) NAME/KEY: Modified-site
          (B) LOCATION: 109
          (D) OTHER INFORMATION: /note= "Xaa at position 109 is Arg,
              Thr, Pro, Glu, Tyr, Leu, Ser, or Gly"

(ix) FEATURE:
          (A) NAME/KEY: Modified-site
          (B) LOCATION: 110
          (D) OTHER INFORMATION: /note= "Xaa at position 110 is Lys,
              Ala, Asn, Thr, Leu, Arg, Gln, His, Glu, Ser, or Trp"

(ix) FEATURE:
          (A) NAME/KEY: Modified-site
          (B) LOCATION: 111
          (D) OTHER INFORMATION: /note= "Xaa at position 111 is Leu,
              Ile, Arg, Asp, or Met"

(ix) FEATURE:
          (A) NAME/KEY: Modified-site
          (B) LOCATION: 112
          (D) OTHER INFORMATION: /note= "Xaa at position 112 is Thr,
              Val, Gln, Tyr, Glu, His, Ser, or Phe"

(ix) FEATURE:
          (A) NAME/KEY: Modified-site
          (B) LOCATION: 113
          (D) OTHER INFORMATION: /note= "Xaa at position 113 is Phe,
              Ser, Cys, His, Gly, Trp, Tyr, Asp, Lys, Leu, Ile, Val,
              or Asn"

(ix) FEATURE:
          (A) NAME/KEY: Modified-site
          (B) LOCATION: 114
          (D) OTHER INFORMATION: /note= "Xaa at position 114 is Tyr,
              Cys, His, Ser, Trp, Arg, or Leu"

(ix) FEATURE:
          (A) NAME/KEY: Modified-site
          (B) LOCATION: 115
          (D) OTHER INFORMATION: /note= "Xaa at position 115 is
              Leu, Asn, Val, Pro, Arg, Ala, His, Thr, Trp, or
              Met"

(ix) FEATURE:
          (A) NAME/KEY: Modified-site
          (B) LOCATION: 116
          (D) OTHER INFORMATION: /note= "Xaa at position 116 is Lys,
              Leu, Pro, Thr, Met, Asp, Val, Glu, Arg, Trp, Ser,
              Asn, His, Ala, Tyr, Phe, Gln, or Ile"

(ix) FEATURE:
          (A) NAME/KEY: Modified-site
          (B) LOCATION: 117
          (D) OTHER INFORMATION: /note= "Xaa at position 117 is Thr,
              Ser, Asn, Ile, Trp, Lys, or Pro"

(ix) FEATURE:
          (A) NAME/KEY: Modified-site
          (B) LOCATION: 118
          (D) OTHER INFORMATION: /note= "Xaa at position 118 is Leu, Ser, Pro, Ala, Glu, Cys, Asp, or Tyr"

(ix) FEATURE:
        (A) NAME/KEY: Modified-site
        (B) LOCATION: 119
        (D) OTHER INFORMATION: /note= "Xaa at position 119 is Glu,
            Ser, Lys, Pro, Leu, Thr, Tyr, or Arg"

(ix) FEATURE:
        (A) NAME/KEY: Modified-site
        (B) LOCATION: 120
        (D) OTHER INFORMATION: /note= "Xaa at position 120 is Asn,
            Ala, Pro, Leu, His, Val, or Gln"

(ix) FEATURE:
        (A) NAME/KEY: Modified-site
        (B) LOCATION: 121
        (D) OTHER INFORMATION: /note= "Xaa at position 121 is Ala,
            Ser, Ile, Asn, Pro, Lys, Asp, or Gly"

(ix) FEATURE:
        (A) NAME/KEY: Modified-site
        (B) LOCATION: 122
        (D) OTHER INFORMATION: /note= "Xaa at position 122 is
            Gln, Ser, Met, Trp, Arg, Phe, Pro, His, Ile, Tyr,
            or Cys"

(ix) FEATURE:
        (A) NAME/KEY: Modified-site
        (B) LOCATION: 123
        (D) OTHER INFORMATION: /note= "Xaa at position 123 is Ala,
            Met, Glu, His, Ser, Pro, Tyr, or Leu"

(xi) SEQUENCE DESCRIPTION: SEQ ID NO:1:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Asn Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Phe Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
    130

(2) INFORMATION FOR SEQ ID NO:2:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:

(A) NAME/KEY: Modified-site
                (B) LOCATION: 17
                (D) OTHER INFORMATION: /note= "Xaa at position 17 is Ser,
                    Gly, Asp, Met, or Gln"

(ix) FEATURE:
                (A) NAME/KEY: Modified-site
                (B) LOCATION: 18
                (D) OTHER INFORMATION: /note= "Xaa at position 18 is Asn,
                    His, or Ile"

(ix) FEATURE:
                (A) NAME/KEY: Modified-site
                (B) LOCATION: 19
                (D) OTHER INFORMATION: /note= "Xaa at position 19 is Met
                    or Ile"

(ix) FEATURE:
                (A) NAME/KEY: Modified-site
                (B) LOCATION: 21
                (D) OTHER INFORMATION: /note="Xaa at position 21 is Asp
                    or Glu"

(ix) FEATURE:
                (A) NAME/KEY: Modified-site
                (B) LOCATION: 23
                (D) OTHER INFORMATION: /note= "Xaa at position 23 is Ile,
                    Ala, Leu, or Gly"

(ix) FEATURE:
                (A) NAME/KEY: Modified-site
                (B) LOCATION: 24
                (D) OTHER INFORMATION: /note= "Xaa at position 24 is Ile,
                    Val, or Leu"

(ix) FEATURE:
                (A) NAME/KEY: Modified-site
                (B) LOCATION: 25
                (D) OTHER INFORMATION: /note= "Xaa at position 25 is Thr,
                    His, Gln, or Ala"

(ix) FEATURE:
                (A) NAME/KEY: Modified-site
                (B) LOCATION: 26
                (D) OTHER INFORMATION: /note= "Xaa at position 26 is His
                    or Ala"

(ix) FEATURE:
                (A) NAME/KEY: Modified-site
                (B) LOCATION: 29
                (D) OTHER INFORMATION: /note= "Xaa at position 29 is Gln,
                    Asn, or Val"

(ix) FEATURE:
                (A) NAME/KEY: Modified-site
                (B) LOCATION: 30
                (D) OTHER INFORMATION: /note= "Xaa at position 30 is Pro,
                    Gly, or Gln"

(ix) FEATURE:
                (A) NAME/KEY: Modified-site
                (B) LOCATION: 31
                (D) OTHER INFORMATION: /note= "Xaa at position 31 is Pro,
                    Asp, Gly, or Gln"

(ix) FEATURE:
                (A) NAME/KEY: Modified-site
                (B) LOCATION: 32
                (D) OTHER INFORMATION: /note= "Xaa at position 32 is Leu,
                    Arg, Gln, Asn, Gly, Ala, or Glu"

(ix) FEATURE:
                (A) NAME/KEY: Modified-site
                (B) LOCATION: 33
                (D) OTHER INFORMATION: /note= "Xaa at position 33 is Pro
                    or Glu"

(ix) FEATURE:
                (A) NAME/KEY: Modified-site

```
          (B) LOCATION: 34
          (D) OTHER INFORMATION: /note= "Xaa at position 34 is Leu,
               Val, Gly, Ser, Lys, Ala, Arg, Gln, Glu, Ile, Phe,
               Thr, or Met"

(ix) FEATURE:
          (A) NAME/KEY: Modified-site
          (B) LOCATION: 35
          (D) OTHER INFORMATION: /note= "Xaa at position 35 is Leu,
               Ala, Asn, Pro, Gln, or Val"

(ix) FEATURE:
          (A) NAME/KEY: Modified-site
          (B) LOCATION: 37
          (D) OTHER INFORMATION: /note= "Xaa at position 37 is Phe,
               Ser, Pro, or Trp"

(ix) FEATURE:
          (A) NAME/KEY: Modified-site
          (B) LOCATION: 38
          (D) OTHER INFORMATION: /note="Xaa at position 38 is Asn
               or Ala"

(ix) FEATURE:
          (A) NAME/KEY: Modified-site
          (B) LOCATION: 42
          (D) OTHER INFORMATION: /note= "Xaa at position 42 is Gly,
               Asp, Ser, Cys, Ala, Asn, Ile, Leu, Met, Tyr,
               or Arg"

(ix) FEATURE:
          (A) NAME/KEY: Modified-site
          (B) LOCATION: 44
          (D) OTHER INFORMATION: /note="Xaa at position 44 is Asp
               or Glu"

(ix) FEATURE:
          (A) NAME/KEY: Modified-site
          (B) LOCATION: 45
          (D) OTHER INFORMATION: /note= "Xaa at position 45 is Gln,
               Val, Met, Leu, Thr, Ala, Asn, Glu, Ser, or Lys"

(ix) FEATURE:
          (A) NAME/KEY: Modified-site
          (B) LOCATION: 46
          (D) OTHER INFORMATION: /note= "Xaa at position 46 is Asp,
               Phe, Ser, Thr, Ala, Asn, Gln, Glu, His, Ile,
               Lys, Tyr, Val, or Cys"

(ix) FEATURE:
          (A) NAME/KEY: Modified-site
          (B) LOCATION: 50
          (D) OTHER INFORMATION: /note= "Xaa at position 50 is Glu,
               Ala, Asn, Ser, or Asp"

(ix) FEATURE:
          (A) NAME/KEY: Modified-site
          (B) LOCATION: 51
          (D) OTHER INFORMATION: /note= "Xaa at position 51 is Asn,
               Arg, Met, Pro, Ser, Thr, or His"

(ix) FEATURE:
          (A) NAME/KEY: Modified-site
          (B) LOCATION: 54
          (D) OTHER INFORMATION: /note="Xaa at position 54 is Arg
               or Ala"

(ix) FEATURE:
          (A) NAME/KEY: Modified-site
          (B) LOCATION: 55
          (D) OTHER INFORMATION: /note= "Xaa at position 55 is Arg,
               Thr, Val, Leu, or Gly"

(ix) FEATURE:
          (A) NAME/KEY: Modified-site
          (B) LOCATION: 56
          (D) OTHER INFORMATION: /note= "Xaa at position 56 is Pro,
               Gly, Ser, Gln, Ala, Arg, Asn, Glu, Leu, Thr, Val,
               or Lys"
```

```
(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn,
        Pro, Thr, or Ile"

(ix) FEATURE:
    (A) NAME/KEY: Modified-site
    (B) LOCATION: 63
    (D) OTHER INFORMATION: /note= "Xaa at position 63 is Arg
        or Lys"

(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 66
    (D) OTHER INFORMATION: /note= "Xaa at position 66 is Lys
        or Arg"

(ix) FEATURE:
    (A) NAME/KEY: Modified-site
    (B) LOCATION: 67
    (D) OTHER INFORMATION: /note= "Xaa at position 67 is Ser
        Phe or His"

(ix) FEATURE:
    (A) NAME/KEY: Modified-site
    (B) LOCATION: 68
    (D) OTHER INFORMATION: /note= "Xaa at position 68 is Leu,
        Ile, Phe, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, or Gly"

(ix) FEATURE:
    (A) NAME/KEY: Modified-site
    (B) LOCATION: 71
    (D) OTHER INFORMATION: /note= "Xaa at position 71 is Ala,
        Pro, or Arg"

(ix) FEATURE:
    (A) NAME/KEY: Modified-site
    (B) LOCATION: 72
    (D) OTHER INFORMATION: /note= "Xaa at position 72 is Ser,
        Glu, Arg, or Asp"

(ix) FEATURE:
    (A) NAME/KEY: Modified-site
    (B) LOCATION: 73
    (D) OTHER INFORMATION: /note= "Xaa at position 73 is Ala
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Glu, Pro, or Gly"
```

(ix) FEATURE:
      (A) NAME/KEY: Modified-site
      (B) LOCATION: 77
      (D) OTHER INFORMATION: /note= "Xaa at position 77 is Ile
          or Leu"

(ix) FEATURE:
      (A) NAME/KEY: Modified-site
      (B) LOCATION: 79
      (D) OTHER INFORMATION: /note= "Xaa at position 79 is
          Lys, Thr, Gly, Asn, Met, Arg, Ile, or Asp"

(ix) FEATURE:
      (A) NAME/KEY: Modified-site
      (B) LOCATION: 80
      (D) OTHER INFORMATION: /note= "Xaa at position 80 is Asn,
          Gly, Glu, or Arg"

(ix) FEATURE:
      (A) NAME/KEY: Modified-site
      (B) LOCATION: 82
      (D) OTHER INFORMATION: /note= "Xaa at position 82 is Leu,
          Gln, Trp, Arg, Asp, Ala, Asn, Glu, His, Ile,
          Met, Phe, Ser, Thr, Tyr, or Val"

(ix) FEATURE:
      (A) NAME/KEY: Modified-site
      (B) LOCATION: 83
      (D) OTHER INFORMATION: /note= "Xaa at position 83 is Pro
          or Thr"

(ix) FEATURE:
      (A) NAME/KEY: Modified-site
      (B) LOCATION: 85
      (D) OTHER INFORMATION: /note= "Xaa at position 85 is Leu
          or Val"

(ix) FEATURE:
      (A) NAME/KEY: Modified-site
      (B) LOCATION: 87
      (D) OTHER INFORMATION: /note= "Xaa at position 87 is Leu
          or Ser"

(ix) FEATURE:
      (A) NAME/KEY: Modified-site
      (B) LOCATION: 88
      (D) OTHER INFORMATION: /note= "Xaa at position 88 is Ala
          or Trp"

(ix) FEATURE:
      (A) NAME/KEY: Modified-site
      (B) LOCATION: 91
      (D) OTHER INFORMATION: /note= "Xaa at position 91 is Ala
          or Pro"

(ix) FEATURE:
      (A) NAME/KEY: Modified-site
      (B) LOCATION: 93
      (D) OTHER INFORMATION: /note= "Xaa at position 93 is Thr,
          Asp, Ser, Pro, Ala, Leu, or Arg"

(ix) FEATURE:
      (A) NAME/KEY: Modified-site
      (B) LOCATION: 95
      (D) OTHER INFORMATION: /note= "Xaa at position 95 is His,
          Pro, Arg, Val, Leu, Gly, Asn, Phe, Ser, or Thr"

(ix) FEATURE:
      (A) NAME/KEY: Modified-site
      (B) LOCATION: 96
      (D) OTHER INFORMATION: /note= "Xaa at position 96 is Pro
          or Tyr"

(ix) FEATURE:
      (A) NAME/KEY: Modified-site
      (B) LOCATION: 97
      (D) OTHER INFORMATION: /note= "Xaa at position 97 is Ile
          or Val"

```
  (ix) FEATURE:
       (A) NAME/KEY: Modified-site
       (B) LOCATION: 98
       (D) OTHER INFORMATION: /note= "Xaa at position 98 is His,
           Ile, Asn, Leu, Ala, Thr, Arg, Gln, Lys,
           Met, Ser, Tyr, Val, or Pro"

(ix) FEATURE:
       (A) NAME/KEY: Modified-site
       (B) LOCATION: 99
       (D) OTHER INFORMATION: /note= "Xaa at position 99 is Ile,
           Leu, or Val"

(ix) FEATURE:
       (A) NAME/KEY: Modified-site
       (B) LOCATION: 100
       (D) OTHER INFORMATION: /note= "Xaa at position 100 is Lys,
           Arg, Ile, Gln, Pro, or Ser"

(ix) FEATURE:
       (A) NAME/KEY: Modified-site
       (B) LOCATION: 101
       (D) OTHER INFORMATION: /note= "Xaa at position 101 is Asp,
           Pro, Met, Lys, Thr, His, Asn, Ile, Leu, or Tyr"

(ix) FEATURE:
       (A) NAME/KEY: Modified-site
       (B) LOCATION: 104
       (D) OTHER INFORMATION: /note= "Xaa at position 104 is Trp
           or Leu"

(ix) FEATURE:
       (A) NAME/KEY: Modified-site
       (B) LOCATION: 105
       (D) OTHER INFORMATION: /note= "Xaa at position 105 is
           Asn, Pro, Ala, Ser, Trp, Gln, Tyr, Leu, Lys, Ile,
           Asp, or His"

(ix) FEATURE:
       (A) NAME/KEY: Modified-site
       (B) LOCATION: 106
       (D) OTHER INFORMATION: /note= "Xaa at position 106 is Glu
           or Gly"

(ix) FEATURE:
       (A) NAME/KEY: Modified-site
       (B) LOCATION: 108
       (D) OTHER INFORMATION: /note="Xaa at position 108 is Arg,
           Ala, or Ser"

(ix) FEATURE:
       (A) NAME/KEY: Modified-site
       (B) LOCATION: 109
       (D) OTHER INFORMATION: /note= "Xaa at position 109 is Arg,
           Thr, Glu, Leu, or Ser"

(ix) FEATURE:
       (A) NAME/KEY: Modified-site
       (B) LOCATION: 112
       (D) OTHER INFORMATION: /note= "Xaa at position 112 is Thr,
           Val, or Gln"

(ix) FEATURE:
       (A) NAME/KEY: Modified-site
       (B) LOCATION: 114
       (D) OTHER INFORMATION: /note= "Xaa at position 114 is Tyr
           or Trp"

(ix) FEATURE:
       (A) NAME/KEY: Modified-site
       (B) LOCATION: 115
       (D) OTHER INFORMATION: /note= "Xaa at position 115 is Leu
           or Ala"

(ix) FEATURE:
       (A) NAME/KEY: Modified-site
       (B) LOCATION: 116
       (D) OTHER INFORMATION: /note= "Xaa at position 116 is Lys,
           Thr, Val, Trp, Ser, Ala, His, Met, Phe, Tyr, or Ile"
```

```
        (ix) FEATURE:
              (A) NAME/KEY: Modified-site
              (B) LOCATION: 117
              (D) OTHER INFORMATION: /note= "Xaa at position 117 is Thr
                   or Ser"

(ix) FEATURE:
              (A) NAME/KEY: Modified-site
              (B) LOCATION: 120
              (D) OTHER INFORMATION: /note= "Xaa at position 120 is Asn,
                   Pro, Leu, His, Val, or Gln"

(ix) FEATURE:
              (A) NAME/KEY: Modified-site
              (B) LOCATION: 121
              (D) OTHER INFORMATION: /note= "Xaa at position 121 is Ala,
                   Ser, Ile, Asn, Pro, Asp, or Gly"

(ix) FEATURE:
              (A) NAME/KEY: Modified-site
              (B) LOCATION: 122
              (D) OTHER INFORMATION: /note= "Xaa at position 122 is
                   Gln, Ser, Met, Trp, Arg, Phe, Pro, His, Ile, Tyr,
                   or Cys"

(ix) FEATURE:
              (A) NAME/KEY: Modified-site
              (B) LOCATION: 123
              (D) OTHER INFORMATION: /note= "Xaa at position 123 is Ala,
                   Met, Glu, His, Ser, Pro, Tyr, or Leu"

(xi) SEQUENCE DESCRIPTION: SEQ ID NO:2:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Xaa Leu Lys Xaa Xaa Xaa Xaa
                20                  25                  30

Xaa Xaa Xaa Asp Xaa Xaa Asn Leu Asn Xaa Glu Xaa Xaa Xaa Ile Leu
            35                  40                  45

Met Xaa Xaa Asn Leu Xaa Xaa Xaa Asn Leu Glu Xaa Phe Xaa Xaa Xaa
    50                  55                  60

Xaa Xaa Xaa Xaa Xaa Asn Xaa Xaa Xaa Ile Glu Xaa Xaa Leu Xaa Xaa
65                  70                  75                  80

Leu Xaa Xaa Cys Xaa Pro Xaa Xaa Thr Ala Xaa Pro Xaa Arg Xaa Xaa
        85                  90                  95

Xaa Xaa Xaa Xaa Xaa Gly Asp Xaa Xaa Xaa Phe Xaa Xaa Lys Leu Xaa
            100                 105                 110

Phe Xaa Xaa Xaa Xaa Leu Glu Xaa Xaa Xaa Xaa Gln Gln Thr Thr Leu
        115                 120                 125

Ser Leu Ala Ile Phe
    130

(2) INFORMATION FOR SEQ ID NO:3:

(i) SEQUENCE CHARACTERISTICS:
              (A) LENGTH: 133 amino acids
              (B) TYPE: amino acid
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Met- may or may not precede
                   the amino acid in position 1"

(ix) FEATURE:
              (A) NAME/KEY: Modified-site
```

```
          (B) LOCATION: 17
          (D) OTHER INFORMATION: /note= "Xaa at position 17 is Ser,
              Gly, Asp, or Gln"

(ix) FEATURE:
          (A) NAME/KEY: Modified-site
          (B) LOCATION: 18
          (D) OTHER INFORMATION: /note= "Xaa at position 18 is Asn,
              His, or Ile"

(ix) FEATURE:
          (A) NAME/KEY: Modified-site
          (B) LOCATION: 23
          (D) OTHER INFORMATION: /note= "Xaa at position 23 is Ile,
              Ala, Leu, or Gly"

(ix) FEATURE:
          (A) NAME/KEY: Modified-site
          (B) LOCATION: 25
          (D) OTHER INFORMATION: /note= "Xaa at position 25 is Thr,
              His, or Gln"

(ix) FEATURE:
          (A) NAME/KEY: Modified-site
          (B) LOCATION: 26
          (D) OTHER INFORMATION: /note= "Xaa at position 26 is His
              or Ala"

(ix) FEATURE:
          (A) NAME/KEY: Modified-site
          (B) LOCATION: 29
          (D) OTHER INFORMATION: /note="Xaa at position 29 is Gln
              or Asn"

(ix) FEATURE:
          (A) NAME/KEY: Modified-site
          (B) LOCATION: 30
          (D) OTHER INFORMATION: /note= "Xaa at position 30 is Pro
              or Gly"

(ix) FEATURE:
          (A) NAME/KEY: Modified-site
          (B) LOCATION: 32
          (D) OTHER INFORMATION: /note= "Xaa at position 32 is Leu,
              Arg, Asn, or Ala"

(ix) FEATURE:
          (A) NAME/KEY: Modified-site
          (B) LOCATION: 34
          (D) OTHER INFORMATION: /note= "Xaa at position 34 is Leu,
              Val, Ser, Ala, Arg, Gln, Glu, Ile, Phe, Thr, or Met"

(ix) FEATURE:
          (A) NAME/KEY: Modified-site
          (B) LOCATION: 35
          (D) OTHER INFORMATION: /note= "Xaa at position 35 is Leu,
              Ala, Asn, or Pro"

(ix) FEATURE:
          (A) NAME/KEY: Modified-site
          (B) LOCATION: 38
          (D) OTHER INFORMATION: /note= "Xaa at position 38 is Asn
              or Ala"

(ix) FEATURE:
          (A) NAME/KEY: Modified-site
          (B) LOCATION: 42
          (D) OTHER INFORMATION: /note= "Xaa at position 42 is Gly,
              Asp, Ser, Ala, Asn, Ile, Leu, Met, Tyr, or Arg"

(ix) FEATURE:
          (A) NAME/KEY: Modified-site
          (B) LOCATION: 45
          (D) OTHER INFORMATION: /note= "Xaa at position 45 is Gln,
              Val, Met, Leu, Ala, Asn, Glu, or Lys"

(ix) FEATURE:
          (A) NAME/KEY: Modified-site
          (B) LOCATION: 46
```

```
            (D) OTHER INFORMATION: /note= "Xaa at position 46 is Asp,
                Phe, Ser, Gln, Glu, His, Val, or Thr"

(ix) FEATURE:
            (A) NAME/KEY: Modified-site
            (B) LOCATION: 50
            (D) OTHER INFORMATION: /note= "Xaa at position 50 is Glu,
                Asn, Ser, or Asp"

(ix) FEATURE:
            (A) NAME/KEY: Modified-site
            (B) LOCATION: 51
            (D) OTHER INFORMATION: /note= "Xaa at position 51 is Asn,
                Arg, Pro, Thr, or His"

(ix) FEATURE:
            (A) NAME/KEY: Modified-site
            (B) LOCATION: 55
            (D) OTHER INFORMATION: /note= "Xaa at position 55 is Arg,
                Leu, or Gly"

(ix) FEATURE:
            (A) NAME/KEY: Modified-site
            (B) LOCATION: 56
            (D) OTHER INFORMATION: /note= "Xaa at position 56 is Pro,
                Gly, Ser, Ala, Asn, Val, Leu, or Gln"

(ix) FEATURE:
            (A) NAME/KEY: Modified-site
            (B) LOCATION: 62
            (D) OTHER INFORMATION: /note= "Xaa at position 62 is Asn,
                Pro, or Thr"

(ix) FEATURE:
            (A) NAME/KEY: Modified-site
            (B) LOCATION: 64
            (D) OTHER INFORMATION: /note= "Xaa at position 64 is Ala
                or Asn"

(ix) FEATURE:
            (A) NAME/KEY: Modified-site
            (B) LOCATION: 65
            (D) OTHER INFORMATION: /note= "Xaa at position 65 is Val
                or Thr"

(ix) FEATURE:
            (A) NAME/KEY: Modified-site
            (B) LOCATION: 67
            (D) OTHER INFORMATION: /note= "Xaa at position 67 is Ser
                or Phe"

(ix) FEATURE:
            (A) NAME/KEY: Modified-site
            (B) LOCATION: 68
            (D) OTHER INFORMATION: /note= "Xaa at position 68 is Leu
                or Phe"

(ix) FEATURE:
            (A) NAME/KEY: Modified-site
            (B) LOCATION: 69
            (D) OTHER INFORMATION: /note= "Xaa at position 69 is Gln,
                Ala, Glu, or Arg"

(ix) FEATURE:
            (A) NAME/KEY: Modified-site
            (B) LOCATION: 76
            (D) OTHER INFORMATION: /note= "Xaa at position 76 is Ser,
                Val, Asn, Pro, or Gly"

(ix) FEATURE:
            (A) NAME/KEY: Modified-site
            (B) LOCATION: 77
            (D) OTHER INFORMATION: /note= "Xaa at position 77 is Ile
                or Leu"

(ix) FEATURE:
            (A) NAME/KEY: Modified-site
            (B) LOCATION: 79
            (D) OTHER INFORMATION: /note= "Xaa at position 79 is Lys,
```

Asn, Met, Arg, Ile, or Gly"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Asn, Glu, His, Met, Phe, Ser,
        Thr, Tyr, or Val"

(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Thr,
        Asp, or Ala"

(ix) FEATURE:
    (A) NAME/KEY: Modified-site
    (B) LOCATION: 95
    (D) OTHER INFORMATION: /note= "Xaa at position 95 is His,
        Pro, Arg, Val, Gly, Asn, Ser, or Thr"

(ix) FEATURE:
    (A) NAME/KEY: Modified-site
    (B) LOCATION: 98
    (D) OTHER INFORMATION: /note= "Xaa at position 98 is His,
        Ile, Asn, Ala, Thr, Gln, Glu, Lys, Met, Ser, Tyr,
        Val, or Leu"

(ix) FEATURE:
    (A) NAME/KEY: Modified-site
    (B) LOCATION: 99
    (D) OTHER INFORMATION: /note= "Xaa at position 99 is Ile
        or Leu"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Asn, Ile, Leu, or Tyr"

(ix) FEATURE:
    (A) NAME/KEY: Modified-site
    (B) LOCATION: 105
    (D) OTHER INFORMATION: /note= "Xaa at position 105 is Asn,
        Pro, Ser, Ile, or Asp"

(ix) FEATURE:
    (A) NAME/KEY:  Modified-site
    (B) LOCATION:  108

(D) OTHER INFORMATION: /note= "Xaa at position 108 is Arg,
            Ala, or Ser"

(ix) FEATURE:
        (A) NAME/KEY: Modified-site
        (B) LOCATION: 109
        (D) OTHER INFORMATION: /note= "Xaa at position 109 is Arg,
            Thr, Glu, Leu, or Ser"

(ix) FEATURE:
        (A) NAME/KEY: Modified-site
        (B) LOCATION: 112
        (D) OTHER INFORMATION: /note= "Xaa at position 112 is Thr
            or Gln"

(ix) FEATURE:
        (A) NAME/KEY: Modified-site
        (B) LOCATION: 116
        (D) OTHER INFORMATION: /note= "Xaa at position 116 is Lys,
            Val, Trp, Ala, His, Phe, Tyr, or Ile"

(ix) FEATURE:
        (A) NAME/KEY: Modified-site
        (B) LOCATION: 117
        (D) OTHER INFORMATION: /note= "Xaa at position 117 is Thr
            or Ser"

(ix) FEATURE:
        (A) NAME/KEY: Modified-site
        (B) LOCATION: 120
        (D) OTHER INFORMATION: /note= "Xaa at position 120 is Asn,
            Pro, Leu, His, Val, or Gln"

(ix) FEATURE:
        (A) NAME/KEY: Modified-site
        (B) LOCATION: 121
        (D) OTHER INFORMATION: /note= "Xaa at position 121 is Ala,
            Ser, Ile, Pro, or Asp"

(ix) FEATURE:
        (A) NAME/KEY: Modified-site
        (B) LOCATION: 122
        (D) OTHER INFORMATION: /note= "Xaa at position 122 is Gln,
            Met, Trp, Phe, Pro, His, Ile, or Tyr"

(ix) FEATURE:
        (A) NAME/KEY: Modified-site
        (B) LOCATION: 123
        (D) OTHER INFORMATION: /note= "Xaa at position 123 is Ala,
            Met, Glu, Ser, or Leu"

(xi) SEQUENCE DESCRIPTION: SEQ ID NO:3:

Ala Pro Met Thr Gln Thr Thr Ser Leu Lys Thr Ser Trp Val Asn Cys
1               5                   10                  15

Xaa Xaa Met Ile Asp Glu Xaa Ile Xaa Xaa Leu Lys Xaa Xaa Pro Xaa
                20                  25                  30

Pro Xaa Xaa Asp Phe Xaa Asn Leu Asn Xaa Glu Asp Xaa Xaa Ile Leu
            35                  40                  45

Met Xaa Xaa Asn Leu Arg Xaa Xaa Asn Leu Glu Ala Phe Xaa Arg Xaa
    50                  55                  60

Xaa Lys Xaa Xaa Xaa Asn Ala Ser Ala Ile Glu Xaa Xaa Leu Xaa Xaa
65                  70                  75                  80

Leu Xaa Pro Cys Leu Pro Xaa Xaa Thr Ala Xaa Pro Xaa Arg Xaa Pro
            85                  90                  95

Ile Xaa Xaa Xaa Xaa Gly Asp Trp Xaa Glu Phe Xaa Xaa Lys Leu Xaa
            100                 105                 110

Phe Tyr Leu Xaa Xaa Leu Glu Xaa Xaa Xaa Xaa Gln Gln Thr Thr Leu
            115                 120                 125

Ser Leu Ala Ile Phe
130

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

(ix) FEATURE:
        (A) NAME/KEY: Modified-site
        (B) LOCATION: 8
        (D) OTHER INFORMATION: /note= "Xaa at position 8 is Glu,
            Trp, Pro, Ser, Ala, His, Asp, Asn, Gln, Leu, Val,
            or Gly"

(ix) FEATURE:
        (A) NAME/KEY: Modified-site
        (B) LOCATION: 9
        (D) OTHER INFORMATION: /note= "Xaa at position 9 is
            Ile, Val, Ala, Leu, Gly, Trp, Lys, Phe, Ser or Arg"

(ix) FEATURE:
        (A) NAME/KEY: Modified-site
        (B) LOCATION: 10
        (D) OTHER INFORMATION: /note= "Xaa at position 10 is Ile,
            Gly, Val, Arg, Ser, Phe, or Leu"

(ix) FEATURE:
        (A) NAME/KEY: Modified-site
        (B) LOCATION: 11
        (D) OTHER INFORMATION: /note= "Xaa at position 11 is Thr,
            His, Gly, Gln, Arg, Pro, or Ala"

(ix) FEATURE:
        (A) NAME/KEY: Modified-site
        (B) LOCATION: 12
        (D) OTHER INFORMATION: /note= "Xaa at position 12 is His,
            Thr, Phe, Gly, Arg, Ala, or Trp"

```
(ix) FEATURE:
    (A) NAME/KEY: Modified-site
    (B) LOCATION: 13
    (D) OTHER INFORMATION: /note= "Xaa at position 13 is Leu,
        Gly, Arg, Thr, Ser, or Ala"

(ix) FEATURE:
    (A) NAME/KEY: Modified-site
    (B) LOCATION: 14
    (D) OTHER INFORMATION: /note= "Xaa at position 14 is Lys,
        Arg, Leu, Gln, Gly, Pro, Val, or Trp"

(ix) FEATURE:
    (A) NAME/KEY: Modified-site
    (B) LOCATION: 15
    (D) OTHER INFORMATION: /note= "Xaa at position 15 is Gln,
        Asn, Leu, Pro, Arg, or Val"

(ix) FEATURE:
    (A) NAME/KEY: Modified-site
    (B) LOCATION: 16
    (D) OTHER INFORMATION: /note= "Xaa at position 16 is Pro,
        His, Thr, Gly, Asp, Gln, Ser, Leu, or Lys"

(ix) FEATURE:
    (A) NAME/KEY: Modified-site
    (B) LOCATION: 17
    (D) OTHER INFORMATION: /note= "Xaa at position 17 is Pro,
        Asp, Gly, Ala, Arg, Leu, or Gln"

(ix) FEATURE:
    (A) NAME/KEY: Modified-site
    (B) LOCATION: 18
    (D) OTHER INFORMATION: /note= "Xaa at position 18 is Leu,
        Val, Arg, Gln, Asn, Gly, Ala, or Glu"

(ix) FEATURE:
    (A) NAME/KEY: Modified-site
    (B) LOCATION: 19
    (D) OTHER INFORMATION: /note= "Xaa at position 19 is Pro,
        Leu, Gln, Ala, Thr, or Glu"

(ix) FEATURE:
    (A) NAME/KEY: Modified-site
    (B) LOCATION: 20
    (D) OTHER INFORMATION: /note= "Xaa at position 20 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 21
    (D) OTHER INFORMATION: /note= "Xaa at position 21 is Leu,
        Ala, Gly, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp,
        Leu, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"
```

```
(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
        Gly, or Ser"

(ix) FEATURE:
    (A) NAME/KEY: Modified-site
    (B) LOCATION: 30
    (D) OTHER INFORMATION: /note= "Xaa at position 30 is Asp,
        Ser, Leu, Arg, Lys, Thr, Met, Trp, Glu, Asn, Gln,
        Ala, or Pro"

(ix) FEATURE:
    (A) NAME/KEY: Modified-site
    (B) LOCATION: 31
    (D) OTHER INFORMATION: /note= "Xaa at position 31 is Gln,
        Pro, Phe, Val, Met, Leu, Thr, Lys, Asp, Asn, Arg,
        Ser, Ala, Ile, Glu, His, or Trp"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Cys, Glu, Asn, Gln, Lys, His, Ala,
        Tyr, Ile, Val, or Gly"

(ix) FEATURE:
    (A) NAME/KEY: Modified-site
    (B) LOCATION: 33
    (D) OTHER INFORMATION: /note= "Xaa at position 33 is Ile,
        Gly, Val, Ser, Arg, Pro, or His"

(ix) FEATURE:
    (A) NAME/KEY: Modified-site
    (B) LOCATION: 34
    (D) OTHER INFORMATION: /note= "Xaa at position 34 is Leu,
        Ser, Cys, Arg, Ile, His, Phe, Glu, Lys, Thr, Ala,
        Met, Val, or Asn"

(ix) FEATURE:
    (A) NAME/KEY: Modified-site
    (B) LOCATION: 35
    (D) OTHER INFORMATION: /note= "Xaa at position 35 is Met,
        Arg, Ala, Gly, Pro, Asn, His, or Asp"

(ix) FEATURE:
    (A) NAME/KEY: Modified-site
    (B) LOCATION: 36
    (D) OTHER INFORMATION: /note= "Xaa at position 36 is Glu,
        Leu, Thr, Asp, Tyr, Lys, Asn, Ser, Ala, Ile, Val,
        His, Phe, Met, or Gln"

(ix) FEATURE:
    (A) NAME/KEY: Modified-site
    (B) LOCATION: 37
    (D) OTHER INFORMATION: /note= "Xaa at position 37 is Asn,
        Arg, Met, Pro, Ser, Thr, or His"

(ix) FEATURE:
    (A) NAME/KEY: Modified-site
    (B) LOCATION: 38
    (D) OTHER INFORMATION: /note= "Xaa at position 38 is Asn,
        His, Arg, Leu, Gly, Ser, or Thr"
```

```
(ix) FEATURE:
    (A) NAME/KEY: Modified-site
    (B) LOCATION: 39
    (D) OTHER INFORMATION: /note= "Xaa at position 39 is
        Leu, Thr, Ala, Gly, Glu, Pro, Lys, Ser, or Met"

(ix) FEATURE:
    (A) NAME/KEY: Modified-site
    (B) LOCATION: 40
    (D) OTHER INFORMATION: /note= "Xaa at position 40 is Arg,
        Asp, Ile, Ser, Val, Thr, Gln, Asn, Lys, His,
        Ala, or Leu"

(ix) FEATURE:
    (A) NAME/KEY: Modified-site
    (B) LOCATION: 41
    (D) OTHER INFORMATION: /note= "Xaa at position 41 is Arg,
        Thr, Val, Ser, Leu, or Gly"

(ix) FEATURE:
    (A) NAME/KEY: Modified-site
    (B) LOCATION: 42
    (D) OTHER INFORMATION: /note= "Xaa at position 42 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 43
    (D) OTHER INFORMATION: /note= "Xaa at position 43 is Asn
        or Gly"

(ix) FEATURE:
    (A) NAME/KEY: Modified-site
    (B) LOCATION: 44
    (D) OTHER INFORMATION: /note= "Xaa at position 44 is Leu,
        Ser, Asp, Arg, Gln, Val, or Cys"

(ix) FEATURE:
    (A) NAME/KEY: Modified-site
    (B) LOCATION: 45
    (D) OTHER INFORMATION: /note= "Xaa at position 45 is Glu,
        Tyr, His, Leu, Pro, or Arg"

(ix) FEATURE:
    (A) NAME/KEY: Modified-site
    (B) LOCATION: 46
    (D) OTHER INFORMATION: /note= "Xaa at position 46 is Ala,
        Ser, Pro, Tyr, Asn, or Thr"

(ix) FEATURE:
    (A) NAME/KEY: Modified-site
    (B) LOCATION: 47
    (D) OTHER INFORMATION: /note= "Xaa at position 47 is Phe,
        Asn, Glu, Pro, Lys, Arg, or Ser"

(ix) FEATURE:
    (A) NAME/KEY: Modified-site
    (B) LOCATION: 48
    (D) OTHER INFORMATION: /note= "Xaa at position 48 is Asn,
        His, Val, Arg, Pro, Thr, Asp, or Ile"

(ix) FEATURE:
    (A) NAME/KEY: Modified-site
    (B) LOCATION: 49
    (D) OTHER INFORMATION: /note= "Xaa at position 49 is Arg,
        Tyr, Trp, Lys, Ser, His, Pro, or Val"

(ix) FEATURE:
    (A) NAME/KEY: Modified-site
    (B) LOCATION: 50
    (D) OTHER INFORMATION: /note= "Xaa at position 50 is Ala,
        Asn, Pro, Ser, or Lys"

(ix) FEATURE:
    (A) NAME/KEY: Modified-site
    (B) LOCATION: 51
    (D) OTHER INFORMATION: /note= "Xaa at position 51 is Val,
        Thr, Pro, His, Leu, Phe, or Ser"
```

```
(ix) FEATURE:
     (A) NAME/KEY: Modified-site
     (B) LOCATION: 52
     (D) OTHER INFORMATION: /note= "Xaa at position 52 is Lys,
         Ile, Arg, Val, Asn, Glu, or Ser"

(ix) FEATURE:
     (A) NAME/KEY: Modified-site
     (B) LOCATION: 53
     (D) OTHER INFORMATION: /note= "Xaa at position 53 is Ser,
         Ala, Phe, Val, Gly, Asn, Ile, Pro, or His"

(ix) FEATURE:
     (A) NAME/KEY: Modified-site
     (B) LOCATION: 54
     (D) OTHER INFORMATION: /note= "Xaa at position 54 is Leu,
         Val, Trp, Ser, Ile, Phe, Thr, or His"

(ix) FEATURE:
     (A) NAME/KEY: Modified-site
     (B) LOCATION: 55
     (D) OTHER INFORMATION: /note= "Xaa at position 55 is Gln,
         Ala, Pro, Thr, Glu, Arg, Trp, Gly, or Leu"

(ix) FEATURE:
     (A) NAME/KEY: Modified-site
     (B) LOCATION: 56
     (D) OTHER INFORMATION: /note= "Xaa at position 56 is Asn,
         Leu, Val, Trp, Pro, or Ala"

(ix) FEATURE:
     (A) NAME/KEY: Modified-site
     (B) LOCATION: 57
     (D) OTHER INFORMATION: /note= "Xaa at position 57 is Ala,
         Met, Leu, Pro, Arg, Glu, Thr, Gln, Trp, or Asn"

(ix) FEATURE:
     (A) NAME/KEY: Modified-site
     (B) LOCATION: 58
     (D) OTHER INFORMATION: /note= "Xaa at position 58 is Ser,
         Glu, Met, Ala, His, Asn, Arg, or Asp"

(ix) FEATURE:
     (A) NAME/KEY: Modified-site
     (B) LOCATION: 59
     (D) OTHER INFORMATION: /note= "Xaa at position 59 is Ala,
         Glu, Asp, Leu, Ser, Gly, Thr, or Arg"

(ix) FEATURE:
     (A) NAME/KEY: Modified-site
     (B) LOCATION: 60
     (D) OTHER INFORMATION: /note= "Xaa at position 60 is Ile,
         Met, Thr, Pro, Arg, Gly, Ala"

(ix) FEATURE:
     (A) NAME/KEY: Modified-site
     (B) LOCATION: 61
     (D) OTHER INFORMATION: /note= "Xaa at position 61 is
         Glu, Lys, Gly, Asp, Pro, Trp, Arg, Ser, Gln,
         or Leu"

(ix) FEATURE:
     (A) NAME/KEY: Modified-site
     (B) LOCATION: 62
     (D) OTHER INFORMATION: /note= "Xaa at position 62 is Ser,
         Val, Ala, Asn, Trp, Glu, Pro, Gly, or Asp"

(ix) FEATURE:
     (A) NAME/KEY: Modified-site
     (B) LOCATION: 63
     (D) OTHER INFORMATION: /note= "Xaa at position 63 is Ile,
         Ser, Arg, Thr, or Leu"

(ix) FEATURE:
     (A) NAME/KEY: Modified-site
     (B) LOCATION: 64
     (D) OTHER INFORMATION: /note= "Xaa at position 64 is Leu,
         Ala, Ser, Glu, Phe, Gly, or Arg"
```

```
(ix) FEATURE:
    (A) NAME/KEY: Modified-site
    (B) LOCATION: 65
    (D) OTHER INFORMATION: /note= "Xaa at position 65 is Lys,
        Thr, Gly, Asn, Met, Arg, Ile, or Asp"

(ix) FEATURE:
    (A) NAME/KEY: Modified-site
    (B) LOCATION: 66
    (D) OTHER INFORMATION: /note= "Xaa at position 66 is Asn,
        Trp, Val, Gly, Thr, Leu, Glu, or Arg"

(ix) FEATURE:
    (A) NAME/KEY: Modified-site
    (B) LOCATION: 67
    (D) OTHER INFORMATION: /note= "Xaa at position 67 is Leu,
        Gln, Gly, Ala, Trp, Arg, Val, or Lys"

(ix) FEATURE:
    (A) NAME/KEY: Modified-site
    (B) LOCATION: 68
    (D) OTHER INFORMATION: /note= "Xaa at position 68 is Leu,
        Gln, Lys, Trp, Arg, Asp, Glu, Asn, His, Thr, Ser, Ala,
        Tyr, Phe, Ile, Met, or Val"

(ix) FEATURE:
    (A) NAME/KEY: Modified-site
    (B) LOCATION: 69
    (D) OTHER INFORMATION: /note= "Xaa at position 69 is Pro,
        Ala, Thr, Trp, Arg, or Met"

(ix) FEATURE:
    (A) NAME/KEY: Modified-site
    (B) LOCATION: 70
    (D) OTHER INFORMATION: /note= "Xaa at position 70 is Cys,
        Glu, Gly, Arg, Met, or Val"

(ix) FEATURE:
    (A) NAME/KEY: Modified-site
    (B) LOCATION: 71
    (D) OTHER INFORMATION: /note= "Xaa at position 71 is Leu,
        Asn, Val, or Gln"

(ix) FEATURE:
    (A) NAME/KEY: Modified-site
    (B) LOCATION: 72
    (D) OTHER INFORMATION: /note= "Xaa at position 72 is Pro,
        Cys, Arg, Ala, or Lys"

(ix) FEATURE:
    (A) NAME/KEY: Modified-site
    (B) LOCATION: 73
    (D) OTHER INFORMATION: /note= "Xaa at position 73 is Leu,
        Ser, Trp, or Gly"

(ix) FEATURE:
    (A) NAME/KEY: Modified-site
    (B) LOCATION: 74
    (D) OTHER INFORMATION: /note= "Xaa at position 74 is Ala,
        Lys, Arg, Val, or Trp"

(ix) FEATURE:
    (A) NAME/KEY: Modified-site
    (B) LOCATION: 75
    (D) OTHER INFORMATION: /note= "Xaa at position 75 is Thr,
        Asp, Cys, Leu, Val, Glu, His, Asn, or Ser"

(ix) FEATURE:
    (A) NAME/KEY: Modified-site
    (B) LOCATION: 76
    (D) OTHER INFORMATION: /note= "Xaa at position 76 is Ala,
        Pro, Ser, Thr, Gly, Asp, Ile, or Met"

(ix) FEATURE:
    (A) NAME/KEY: Modified-site
    (B) LOCATION: 77
    (D) OTHER INFORMATION: /note= "Xaa at position 77 is Ala,
        Pro, Ser, Thr, Phe, Leu, Asp, or His"
```

(ix) FEATURE:
      (A) NAME/KEY: Modified-site
      (B) LOCATION: 78
      (D) OTHER INFORMATION: /note= "Xaa at position 78 is Pro,
          Phe, Arg, Ser, Lys, His, Ala, Gly, Ile, or Leu"

(ix) FEATURE:
      (A) NAME/KEY: Modified-site
      (B) LOCATION: 79
      (D) OTHER INFORMATION: /note= "Xaa at position 79 is Thr,
          Asp, Ser, Asn, Pro, Ala, Leu, or Arg"

(ix) FEATURE:
      (A) NAME/KEY: Modified-site
      (B) LOCATION: 80
      (D) OTHER INFORMATION: /note= "Xaa at position 80 is Arg,
          Ile, Ser, Glu, Leu, Val, Gln, Lys, His, Ala, or Pro"

(ix) FEATURE:
      (A) NAME/KEY: Modified-site
      (B) LOCATION: 81
      (D) OTHER INFORMATION: /note= "Xaa at position 81 is His,
          Gln, Pro, Arg, Val, Leu, Gly, Thr, Asn, Lys, Ser,
          Ala, Trp, Phe, Ile, or Tyr"

(ix) FEATURE:
      (A) NAME/KEY: Modified-site
      (B) LOCATION: 82
      (D) OTHER INFORMATION: /note= "Xaa at position 82 is Pro,
          Lys, Tyr, Gly, Ile, or Thr"

(ix) FEATURE:
      (A) NAME/KEY: Modified-site
      (B) LOCATION: 83
      (D) OTHER INFORMATION: /note= "Xaa at position 83 is Ile,
          Val, Lys, Ala, or Asn"

(ix) FEATURE:
      (A) NAME/KEY: Modified-site
      (B) LOCATION: 84
      (D) OTHER INFORMATION: /note= "Xaa at position 84 is His,
          Ile, Asn, Leu, Asp, Ala, Thr, Glu, Gln, Ser,
          Phe, Met, Val, Lys, Arg, Tyr, or Pro"

(ix) FEATURE:
      (A) NAME/KEY: Modified-site
      (B) LOCATION: 85
      (D) OTHER INFORMATION: /note= "Xaa at position 85 is
          Ile, Leu, Arg, Asp, Val, Pro, Gln, Gly, Ser,
          Phe, or His"

(ix) FEATURE:
      (A) NAME/KEY: Modified-site
      (B) LOCATION: 86
      (D) OTHER INFORMATION: /note= "Xaa at position 86 is
          Lys, Tyr, Leu, His, Arg, Ile, Ser, Gln, or Pro"

(ix) FEATURE:
      (A) NAME/KEY: Modified-site
      (B) LOCATION: 87
      (D) OTHER INFORMATION: /note= "Xaa at position 87 is
          Asp, Pro, Met, Lys, His, Thr, Val, Tyr, Glu, Asn,
          Ser, Ala, Gly, Ile, Leu, or Gln"

(ix) FEATURE:
      (A) NAME/KEY: Modified-site
      (B) LOCATION: 88
      (D) OTHER INFORMATION: /note= "Xaa at position 88 Gly,
          Leu, Glu, Lys, Ser, Tyr, or Pro"

(ix) FEATURE:
      (A) NAME/KEY: Modified-site
      (B) LOCATION: 89
      (D) OTHER INFORMATION: /note= "Xaa at position 89 is Asp
          or Ser"

(ix) FEATURE:
      (A) NAME/KEY: Modified-site

```
        (B) LOCATION: 90
        (D) OTHER INFORMATION: /note= "Xaa at position 90 is
            Trp, Val, Cys, Tyr, Thr, Met, Pro, Leu, Gln, Lys,
            Ala, Phe, or Gly"

(ix) FEATURE:
        (A) NAME/KEY: Modified-site
        (B) LOCATION: 91
        (D) OTHER INFORMATION: /note= "Xaa at position 91 is
            Asn, Pro, Ala, Phe, Ser, Trp, Gln, Tyr, Leu, Lys,
            Ile, Asp, or His"

(ix) FEATURE:
        (A) NAME/KEY: Modified-site
        (B) LOCATION: 92
        (D) OTHER INFORMATION: /note= "Xaa at position 92 is Glu,
            Ser, Ala, Lys, Thr, Ile, Gly, or Pro"

(ix) FEATURE:
        (A) NAME/KEY: Modified-site
        (B) LOCATION: 94
        (D) OTHER INFORMATION: /note= "Xaa at position 94 is Arg,
            Lys, Asp, Leu, Thr, Ile, Gln, His, Ser, Ala, or Pro"

(ix) FEATURE:
        (A) NAME/KEY: Modified-site
        (B) LOCATION: 95
        (D) OTHER INFORMATION: /note= "Xaa at position 95 is Arg,
            Thr, Pro, Glu, Tyr, Leu, Ser, or Gly"

(ix) FEATURE:
        (A) NAME/KEY: Modified-site
        (B) LOCATION: 96
        (D) OTHER INFORMATION: /note= "Xaa at position 96 is Lys,
            Asn, Thr, Leu, Gln, Arg, His, Glu, Ser, Ala,
            or Trp"

(ix) FEATURE:
        (A) NAME/KEY: Modified-site
        (B) LOCATION: 97
        (D) OTHER INFORMATION: /note= "Xaa at position 97 is Leu,
            Ile, Arg, Asp, or Met"

(ix) FEATURE:
        (A) NAME/KEY: Modified-site
        (B) LOCATION: 98
        (D) OTHER INFORMATION: /note= "Xaa at position 98 is Thr,
            Val, Gln, Tyr, Glu, His, Ser, or Phe"

(ix) FEATURE:
        (A) NAME/KEY: Modified-site
        (B) LOCATION: 99
        (D) OTHER INFORMATION: /note= "Xaa at position 99 is Phe,
            Ser, Cys, His, Gly, Trp, Tyr, Asp, Lys, Leu, Ile,
            Val, or Asn"

(ix) FEATURE:
        (A) NAME/KEY: Modified-site
        (B) LOCATION: 100
        (D) OTHER INFORMATION: /note= "Xaa at position 100 is Tyr,
            Cys, His, Ser, Trp, Arg, or Leu"

(ix) FEATURE:
        (A) NAME/KEY: Modified-site
        (B) LOCATION: 101
        (D) OTHER INFORMATION: /note= "Xaa at position 101 is Leu,
            Asn, Val, Pro, Arg, Ala, His, Thr, Trp, or Met"

(ix) FEATURE:
        (A) NAME/KEY: Modified-site
        (B) LOCATION: 102
        (D) OTHER INFORMATION: /note= "Xaa at position 102 is
            Lys, Leu, Pro, Thr, Met, Asp, Val, Glu, Arg, Trp,
            Ser, Asn, His, Ala, Tyr, Phe, Gln, or Ile"

(ix) FEATURE:
        (A) NAME/KEY: Modified-site
        (B) LOCATION: 103
        (D) OTHER INFORMATION: /note= "Xaa at position 103 is Thr,
```

-continued

Ser, Asn, Ile, Trp, Lys, or Pro"

(ix) FEATURE:
(A) NAME/KEY: Modified-site
(B) LOCATION: 104
(D) OTHER INFORMATION: /note= "Xaa at position 104 is Leu, Ser, Pro, Ala, Glu, Cys, Asp, or Tyr"

(ix) FEATURE:
(A) NAME/KEY: Modified-site
(B) LOCATION: 105
(D) OTHER INFORMATION: /note= "Xaa at position 105 is Glu, Ser, Lys, Pro, Leu, Thr, Tyr, or Arg"

(ix) FEATURE:
(A) NAME/KEY: Modified-site
(B) LOCATION: 106
(D) OTHER INFORMATION: /note= "Xaa at position 106 is Asn, Ala, Pro, Leu, His, Val or Gln"

(ix) FEATURE:
(A) NAME/KEY: Modified-site
(B) LOCATION: 107
(D) OTHER INFORMATION: /note= "Xaa at position 107 is Ala, Ser, Ile, Asn, Pro, Lys, Asp, or Gly"

(ix) FEATURE:
(A) NAME/KEY: Modified-site
(B) LOCATION: 108
(D) OTHER INFORMATION: /note= "Xaa at position 108 is Gln, Ser, Met, Trp, Arg, Phe, Pro, His, Ile, Tyr, or Cys"

(ix) FEATURE:
(A) NAME/KEY: Modified-site
(B) LOCATION: 109
(D) OTHER INFORMATION: /note= "Xaa at position 109 is Ala, Met, Glu, His, Ser, Pro, Tyr, or Leu"

(xi) SEQUENCE DESCRIPTION: SEQ ID NO:4:

```
Asn Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Asn Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Phe Xaa Xaa Xaa
                85                  90                  95

Xaa Xaa Xaa Xaa Xaa Xaa Xaa Xaa Xaa Xaa Xaa Xaa Xaa Gln Gln
            100                 105                 110
```

(2) INFORMATION FOR SEQ ID NO:5:

(i) SEQUENCE CHARACTERISTICS:
(A) LENGTH: 111 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Met- or Met-Ala- may or may not precede the amino acid in position 1"

(ix) FEATURE:

```
            (A) NAME/KEY: Modified-site
            (B) LOCATION: 3
            (D) OTHER INFORMATION: /note= "Xaa at position 3 is Ser,
                Gly, Asp, Met, or Gln"

(ix) FEATURE:
            (A) NAME/KEY: Modified-site
            (B) LOCATION: 4
            (D) OTHER INFORMATION: /note= "Xaa at position 4 is Asn,
                His, or Ile"

(ix) FEATURE:
            (A) NAME/KEY: Modified-site
            (B) LOCATION: 5
            (D) OTHER INFORMATION: /note= "Xaa at position 5 is Met
                or Ile"

(ix) FEATURE:
            (A) NAME/KEY: Modified-site
            (B) LOCATION: 7
            (C) OTHER INFORMATION: /note= "Xaa at position 7 is Asp or
                Glu"

(ix) FEATURE:
            (A) NAME/KEY: Modified-site
            (B) LOCATION: 9
            (D) OTHER INFORMATION: /note= "Xaa at position 9 is Ile,
                Ala, Leu, or Gly"

(ix) FEATURE:
            (A) NAME/KEY: Modified-site
            (B) LOCATION: 10
            (D) OTHER INFORMATION: /note= "Xaa at position 10 is Ile,
                Val, or Leu"

(ix) FEATURE:
            (A) NAME/KEY: Modified-site
            (B) LOCATION: 11
            (D) OTHER INFORMATION: /note= "Xaa at position 11 is Thr,
                His, Gln, or Ala"

(ix) FEATURE:
            (A) NAME/KEY: Modified-site
            (B) LOCATION: 12
            (D) OTHER INFORMATION: /note= "Xaa at position 12 is His
                or Ala"

(ix) FEATURE:
            (A) NAME/KEY: Modified-site
            (B) LOCATION: 15
            (D) OTHER INFORMATION: /note= "Xaa at position 15 is Gln,
                Asn, or Val"

(ix) FEATURE:
            (A) NAME/KEY: Modified-site
            (B) LOCATION: 16
            (D) OTHER INFORMATION: /note= "Xaa at position 16 is Pro,
                Gly, or Gln"

(ix) FEATURE:
            (A) NAME/KEY: Modified-site
            (B) LOCATION: 17
            (D) OTHER INFORMATION: /note= "Xaa at position 17 is Pro,
                Asp, Gly, or Gln"

(ix) FEATURE:
            (A) NAME/KEY: Modified-site
            (B) LOCATION: 18
            (D) OTHER INFORMATION: /note= "Xaa at position 18 is Leu,
                Arg, Gln, Asn, Gly, Ala, or Glu"

(ix) FEATURE:
            (A) NAME/KEY: Modified-site
            (B) LOCATION: 19
            (D) OTHER INFORMATION: /note= "Xaa at position 19 is Pro
                or Glu"

(ix) FEATURE:
            (A) NAME/KEY: Modified-site
```

```
          (B) LOCATION: 20
          (D) OTHER INFORMATION: /note= "Xaa at position 20 is Leu,
              Val, Gly, Ser, Lys, Ala, Arg, Gln, Glu, Ile, Phe,
              Thr, or Met"

(ix) FEATURE:
          (A) NAME/KEY: Modified-site
          (B) LOCATION: 21
          (D) OTHER INFORMATION: /note= "Xaa at position 21 is Leu,
              Ala, Asn, Pro, Gln, or Val"

(ix) FEATURE:
          (A) NAME/KEY: Modified-site
          (B) LOCATION: 23
          (D) OTHER INFORMATION: /note= "Xaa at position 23 is Phe,
              Ser, Pro, or Trp"

(ix) FEATURE:
          (A) NAME/KEY: Modified-site
          (B) LOCATION: 24
          (D) OTHER INFORMATION: /note= "Xaa at position 24 is Asn
              or Ala"

(ix) FEATURE:
          (A) NAME/KEY: Modified-site
          (B) LOCATION: 28
          (D) OTHER INFORMATION: /note= "Xaa at position 28 is Gly,
              Asp, Ser, Cys, Ala, Asn, Ile, Leu, Met, Tyr, or Arg"

(ix) FEATURE:
          (A) NAME/KEY: Modified-site
          (B) LOCATION: 30
          (D) OTHER INFORMATION: /note= "Xaa at position 30 is Asp
              or Glu"

(ix) FEATURE:
          (A) NAME/KEY: Modified-site
          (B) LOCATION: 31
          (D) OTHER INFORMATION: /note= "Xaa at position 31 is Gln,
              Val, Met, Leu, Thr, Ala, Asn, Glu, Ser, or Lys"

(ix) FEATURE:
          (A) NAME/KEY: Modified-site
          (B) LOCATION: 32
          (D) OTHER INFORMATION: /note= "Xaa at position 32 is Asp,
              Phe, Ser, Thr, Ala, Asn, Gln, Glu, His, Ile, Lys,
              Tyr, Val, or Cys"

(ix) FEATURE:
          (A) NAME/KEY: Modified-site
          (B) LOCATION: 36
          (D) OTHER INFORMATION: /note= "Xaa at position 36 is Glu,
              Ala, Asn, Ser, or Asp"

(ix) FEATURE:
          (A) NAME/KEY: Modified-site
          (B) LOCATION: 37
          (D) OTHER INFORMATION: /note= "Xaa at position 37 is Asn,
              Arg, Met, Pro, Ser, Thr, or His"

(ix) FEATURE:
          (A) NAME/KEY: Modified-site
          (B) LOCATION: 40
          (D) OTHER INFORMATION: /note= "Xaa at position 40 is Arg
              or Ala"

(ix) FEATURE:
          (A) NAME/KEY: Modified-site
          (B) LOCATION: 41
          (D) OTHER INFORMATION: /note= "Xaa at position 41 is Arg,
              Thr, Val, Leu, or Gly"

(ix) FEATURE:
          (A) NAME/KEY: Modified-site
          (B) LOCATION: 42
          (D) OTHER INFORMATION: /note= "Xaa at position 42 is Pro,
              Gly, Ser, Gln, Ala, Arg, Asn, Glu, Leu, Thr, Val,
              or Lys"
```

```
-continued (ix) FEATURE:
     (A) NAME/KEY: Modified-site
     (B) LOCATION: 46
     (D) OTHER INFORMATION: /note= "Xaa at position 46 is Ala
         or Ser"

(ix) FEATURE:
     (A) NAME/KEY: Modified-site
     (B) LOCATION: 48
     (D) OTHER INFORMATION: /note= "Xaa at position 48 is Asn,
         Pro, Thr, or Ile"

(ix) FEATURE:
     (A) NAME/KEY: Modified-site
     (B) LOCATION: 49
     (D) OTHER INFORMATION: /note= "Xaa at position 49 is Arg
         or Lys"

(ix) FEATURE:
     (A) NAME/KEY: Modified-site
     (B) LOCATION: 50
     (D) OTHER INFORMATION: /note= "Xaa at position 50 is Ala
         or Asn"

(ix) FEATURE:
     (A) NAME/KEY: Modified-site
     (B) LOCATION: 51
     (D) OTHER INFORMATION: /note= "Xaa at position 51 is Val
         or Thr"

(ix) FEATURE:
     (A) NAME/KEY: Modified-site
     (B) LOCATION: 52
     (D) OTHER INFORMATION: /note= "Xaa at position 52 is Lys
         or Arg"

(ix) FEATURE:
     (A) NAME/KEY: Modified-site
     (B) LOCATION: 53
     (D) OTHER INFORMATION: /note= "Xaa at position 53 is Ser,
         Phe, or His"

(ix) FEATURE:
     (A) NAME/KEY: Modified-site
     (B) LOCATION: 54
     (D) OTHER INFORMATION: /note= "Xaa at position 54 is Leu,
         Ile, Phe, or His"

(ix) FEATURE:
     (A) NAME/KEY: Modified-site
     (B) LOCATION: 55
     (D) OTHER INFORMATION: /note= "Xaa at position 55 is Gln,
         Ala, Pro, Thr, Glu, Arg, or Gly"

(ix) FEATURE:
     (A) NAME/KEY: Modified-site
     (B) LOCATION: 57
     (D) OTHER INFORMATION: /note= "Xaa at position 57 is Ala,
         Pro, or Arg"

(ix) FEATURE:
     (A) NAME/KEY: Modified-site
     (B) LOCATION: 58
     (D) OTHER INFORMATION: /note= "Xaa at position 58 is Ser,
         Glu, Arg, or Asp"

(ix) FEATURE:
     (A) NAME/KEY: Modified-site
     (B) LOCATION: 59
     (D) OTHER INFORMATION: /note= "Xaa at position 59 is Ala
         or Leu"

(ix) FEATURE:
     (A) NAME/KEY: Modified-site
     (B) LOCATION: 62
     (D) OTHER INFORMATION: /note= "Xaa at position 62 is Ser,
         Val, Ala, Asn, Glu, Pro, or Gly"

(ix) FEATURE:
```

```
        (A) NAME/KEY: Modified-site
        (B) LOCATION: 63
        (D) OTHER INFORMATION: /note= "Xaa at position 63 is Ile
            or Leu"

(ix) FEATURE:
        (A) NAME/KEY: Modified-site
        (B) LOCATION: 65
        (D) OTHER INFORMATION: /note= "Xaa at position 65 is Lys,
            Thr, Gly, Asn, Met, Arg, Ile, or Asp"

(ix) FEATURE:
        (A) NAME/KEY: Modified-site
        (B) LOCATION: 66
        (D) OTHER INFORMATION: /note= "Xaa at position 66 is Asn,
            Gly, Glu, or Arg"

(ix) FEATURE:
        (A) NAME/KEY: Modified-site
        (B) LOCATION: 68
        (D) OTHER INFORMATION: /note= "Xaa at position 68 is Leu,
            Gln, Trp, Arg, Asp, Ala, Asn, Glu, His, Ile, Met,
            Phe, Ser, Thr, Tyr, or Val"

(ix) FEATURE:
        (A) NAME/KEY: Modified-site
        (B) LOCATION: 69
        (D) OTHER INFORMATION: /note= "Xaa at position 69 is Pro
            or Thr"

(ix) FEATURE:
        (A) NAME/KEY: Modified-site
        (B) LOCATION: 71
        (D) OTHER INFORMATION: /note= "Xaa at position 71 is Leu
            or Val"

(ix) FEATURE:
        (A) NAME/KEY: Modified-site
        (B) LOCATION: 73
        (D) OTHER INFORMATION: /note= "Xaa at position 73 is Leu
            or Ser"

(ix) FEATURE:
        (A) NAME/KEY: Modified-site
        (B) LOCATION: 74
        (D) OTHER INFORMATION: /note= "Xaa at position 74 is Ala
            or Trp"

(ix) FEATURE:
        (A) NAME/KEY: Modified-site
        (B) LOCATION: 77
        (D) OTHER INFORMATION: /note= "Xaa at position 77 is Ala
            or Pro"

(ix) FEATURE:
        (A) NAME/KEY: Modified-site
        (B) LOCATION: 79
        (D) OTHER INFORMATION: /note= "Xaa at position 79 is Thr,
            Asp, Ser, Pro, Ala, Leu, or Arg"

(ix) FEATURE:
        (A) NAME/KEY: Modified-site
        (B) LOCATION: 81
        (D) OTHER INFORMATION: /note= "Xaa at position 81 is His,
            Pro, Arg, Val, Leu, Gly, Asn, Phe, Ser, or Thr"

(ix) FEATURE:
        (A) NAME/KEY: Modified-site
        (B) LOCATION: 82
        (D) OTHER INFORMATION: /note= "Xaa at position 82 is Pro
            or Tyr"

(ix) FEATURE:
        (A) NAME/KEY: Modified-site
        (B) LOCATION: 83
        (D) OTHER INFORMATION: /note= "Xaa at position 83 is Ile
            or Val"

(ix) FEATURE:
```

```
         (A) NAME/KEY: Modified-site
         (B) LOCATION: 84
         (D) OTHER INFORMATION: /note= "Xaa at position 84 is His,
             Ile, Asn, Leu, Ala, Thr, Arg, Gln, Lys,
             Met, Ser, Tyr, Val, or Pro"

(ix) FEATURE:
         (A) NAME/KEY: Modified-site
         (B) LOCATION: 85
         (D) OTHER INFORMATION: /note= "Xaa at position 85 is Ile,
             Leu, or Val"

(ix) FEATURE:
         (A) NAME/KEY: Modified-site
         (B) LOCATION: 86
         (D) OTHER INFORMATION: /note= "Xaa at position 86 is Lys,
             Arg, Ile, Gln, Pro, or Ser"

(ix) FEATURE:
         (A) NAME/KEY: Modified-site
         (B) LOCATION: 87
         (D) OTHER INFORMATION: /note= "Xaa at position 87 is Asp,
             Pro, Met, Lys, His, Thr, Asn, Ile, Leu, or Tyr"

(ix) FEATURE:
         (A) NAME/KEY: Modified-site
         (B) LOCATION: 90
         (D) OTHER INFORMATION: /note= "Xaa at position 90 is Trp
             or Leu"

(ix) FEATURE:
         (A) NAME/KEY: Modified-site
         (B) LOCATION: 91
         (D) OTHER INFORMATION: /note="Xaa at position 91 is Asn,
             Pro, Ala, Ser, Trp, Gln, Tyr, Leu, Lys, Ile, Asp,
             or His"

(ix) FEATURE:
         (A) NAME/KEY: Modified-site
         (B) LOCATION: 92
         (D) OTHER INFORMATION: /note= "Xaa at position 92 is Glu
             or Gly"

(ix) FEATURE:
         (A) NAME/KEY: Modified-site
         (B) LOCATION: 94
         (C) OTHER INFORMATION: /note= "Xaa at position 94 is Arg,
             Ala, or Ser"

(ix) FEATURE:
         (A) NAME/KEY: Modified-site
         (B) LOCATION: 95
         (D) OTHER INFORMATION: /note= "Xaa at position 95 is Arg,
             Thr, Glu, Leu, or Ser"

(ix) FEATURE:
         (A) NAME/KEY: Modified-site
         (B) LOCATION: 98
         (D) OTHER INFORMATION: /note= "Xaa at position 98 is Thr,
             Val, or Gln"

(ix) FEATURE:
         (A) NAME/KEY: Modified-site
         (B) LOCATION: 100
         (D) OTHER INFORMATION: /note= "Xaa at position 100 is Tyr
             or Trp"

(ix) FEATURE:
         (A) NAME/KEY: Modified-site
         (B) LOCATION: 101
         (D) OTHER INFORMATION: /note= "Xaa at position 101 is Leu
             or Ala"

(ix) FEATURE:
         (A) NAME/KEY: Modified-site
         (B) LOCATION: 102
         (D) OTHER INFORMATION: /note= "Xaa at position 102 is Lys,
             Thr, Val, Trp, Ser, Ala, His, Met, Phe, Tyr, or Ile"
```

(ix) FEATURE:
  (A) NAME/KEY: Modified-site
  (B) LOCATION: 103
  (D) OTHER INFORMATION: /note= "Xaa at position 103 is Thr or Ser"

(ix) FEATURE:
  (A) NAME/KEY: Modified-site
  (B) LOCATION: 106
  (D) OTHER INFORMATION: /note= "Xaa at position 106 is Asn, Pro, Leu, His, Val, or Gln"

(ix) FEATURE:
  (A) NAME/KEY: Modified-site
  (B) LOCATION: 107
  (D) OTHER INFORMATION: /note= "Xaa at position 107 is Ala, Ser, Ile, Asn, Pro, Asp, or Gly"

(ix) FEATURE:
  (A) NAME/KEY: Modified-site
  (B) LOCATION: 108
  (D) OTHER INFORMATION: /note= "Xaa at position 108 is Gln, Ser, Met, Trp, Arg, Phe, Pro, His, Ile, Tyr, or Cys"

(ix) FEATURE:
  (A) NAME/KEY: Modified-site
  (B) LOCATION: 109
  (D) OTHER INFORMATION: /note= "Xaa at position 109 is Ala, Met, Glu, His, Ser, Pro, Tyr, or Leu"

(xi) SEQUENCE DESCRIPTION: SEQ ID NO:5:

```
Asn Cys Xaa Xaa Xaa Ile Xaa Glu Xaa Xaa Xaa Xaa Leu Lys Xaa Xaa
1               5                   10                  15

Xaa Xaa Xaa Xaa Xaa Asp Xaa Xaa Asn Leu Asn Xaa Glu Xaa Xaa Xaa
            20                  25                  30

Ile Leu Met Xaa Xaa Asn Leu Xaa Xaa Xaa Asn Leu Glu Xaa Phe Xaa
            35                  40                  45

Xaa Xaa Xaa Xaa Xaa Xaa Xaa Asn Xaa Xaa Xaa Ile Glu Xaa Xaa Leu
50                  55                  60

Xaa Xaa Leu Xaa Xaa Cys Xaa Pro Xaa Xaa Thr Ala Xaa Pro Xaa Arg
65                  70                  75                  80

Xaa Xaa Xaa Xaa Xaa Xaa Xaa Gly Asp Xaa Xaa Xaa Phe Xaa Xaa Lys
            85                  90                  95

Leu Xaa Phe Xaa Xaa Xaa Xaa Leu Glu Xaa Xaa Xaa Xaa Gln Gln
            100                 105                 110
```

(2) INFORMATION FOR SEQ ID NO:6:

(i) SEQUENCE CHARACTERISTICS:
    (A) LENGTH: 111 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Met- or Met-Ala- may or may not precede the amino acid in position 1"

(ix) FEATURE:
    (A) NAME/KEY: Modified-site
    (B) LOCATION: 3
    (D) OTHER INFORMATION: /note= "Xaa at position 3 is Ser, Gly, Asp, or Gln"

(ix) FEATURE:
    (A) NAME/KEY: Modified-site
    (B) LOCATION: 4
    (D) OTHER INFORMATION: /note= "Xaa at position 4 is Asn, His, or Ile"

(ix) FEATURE:
    (A) NAME/KEY: Modified-site
    (B) LOCATION: 9
    (D) OTHER INFORMATION: /note= "Xaa at position 9 is Ile,
        Ala, Leu, or Gly"

(ix) FEATURE:
    (A) NAME/KEY: Modified-site
    (B) LOCATION: 11
    (D) OTHER INFORMATION: /note= "Xaa at position 11 is Thr,
        His, or Gln"

(ix) FEATURE:
    (A) NAME/KEY: Modified-site
    (B) LOCATION: 12
    (D) OTHER INFORMATION: /note= "Xaa at position 12 is His
        or Ala"

(ix) FEATURE:
    (A) NAME/KEY: Modified-site
    (B) LOCATION: 15
    (D) OTHER INFORMATION: /note= "Xaa at position 15 is Gln
        or Asn"

(ix) FEATURE:
    (A) NAME/KEY: Modified-site
    (B) LOCATION: 16
    (D) OTHER INFORMATION: /note= "Xaa at position 16 is Pro
        or Gly"

(ix) FEATURE:
    (A) NAME/KEY: Modified-site
    (B) LOCATION: 18
    (D) OTHER INFORMATION: /note= "Xaa at position 18 is Leu,
        Arg, Asn, or Ala"

(ix) FEATURE:
    (A) NAME/KEY: Modified-site
    (B) LOCATION: 20
    (D) OTHER INFORMATION: /note= "Xaa at position 20 is Leu,
        Val, Ser, Ala, Arg, Gln, Glu, Ile, Phe, Thr, or Met"

(ix) FEATURE:
    (A) NAME/KEY: Modified-site
    (B) LOCATION: 21
    (D) OTHER INFORMATION: /note= "Xaa at position 21 is Leu,
        Ala, Asn, or Pro"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Asp, Ser, Ala, Asn, Ile, Leu, Met, Tyr, or Arg"

(ix) FEATURE:
    (A) NAME/KEY: Modified-site
    (B) LOCATION: 31
    (D) OTHER INFORMATION: /note= "Xaa at position 31 is Gln,
        Val, Met, Leu, Ala, Asn, Glu, or Lys"

(ix) FEATURE:
    (A) NAME/KEY: Modified-site
    (B) LOCATION: 32
    (D) OTHER INFORMATION: /note= "Xaa at position 32 is Asp,
        Phe, Ser, Ala, Gln, Glu, His, Val, or Thr"

(ix) FEATURE:
    (A) NAME/KEY: Modified-site
    (B) LOCATION: 36
    (D) OTHER INFORMATION: /note= "Xaa at position 36 is Glu,
        Asn, Ser, or Asp"

```
(ix) FEATURE:
    (A) NAME/KEY: Modified-site
    (B) LOCATION: 37
    (D) OTHER INFORMATION: /note= "Xaa at position 37 is Asn,
        Arg, Pro, Thr, or His"

(ix) FEATURE:
    (A) NAME/KEY: Modified-site
    (B) LOCATION: 41
    (D) OTHER INFORMATION: /note= "Xaa at position 41 is Arg,
        Leu, or Gly"

(ix) FEATURE:
    (A) NAME/KEY: Modified-site
    (B) LOCATION: 42
    (D) OTHER INFORMATION: /note= "Xaa at position 42 is Pro,
        Gly, Ser, Ala, Asn, Val, Leu, or Gln"

(ix) FEATURE:
    (A) NAME/KEY: Modified-site
    (B) LOCATION: 48
    (D) OTHER INFORMATION: /note= "Xaa at position 48 is Asn,
        Pro, or Thr"

(ix) FEATURE:
    (A) NAME/KEY: Modified-site
    (B) LOCATION: 50
    (D) OTHER INFORMATION: /note= "Xaa at position 50 is Ala
        or Asn"

(ix) FEATURE:
    (A) NAME/KEY: Modified-site
    (B) LOCATION: 51
    (D) OTHER INFORMATION: /note= "Xaa at position 51 is Val
        or Thr"

(ix) FEATURE:
    (A) NAME/KEY: Modified-site
    (B) LOCATION: 53
    (D) OTHER INFORMATION: /note= "Xaa at position 53 is Ser
        or Phe"

(ix) FEATURE:
    (A) NAME/KEY: Modified-site
    (B) LOCATION: 54
    (D) OTHER INFORMATION: /note= "Xaa at position 54 is Leu
        or Phe"

(ix) FEATURE:
    (A) NAME/KEY: Modified-site
    (B) LOCATION: 55
    (D) OTHER INFORMATION: /note= "Xaa at position 55 is Gln,
        Ala, Glu, or Arg"

(ix) FEATURE:
    (A) NAME/KEY: Modified-site
    (B) LOCATION: 62
    (D) OTHER INFORMATION: /note= "Xaa at position 62 is Ser,
        Val, Asn, Pro, or Gly"

(ix) FEATURE:
    (A) NAME/KEY: Modified-site
    (B) LOCATION: 63
    (D) OTHER INFORMATION: /note= "Xaa at position 63 is Ile
        or Leu"

(ix) FEATURE:
    (A) NAME/KEY: Modified-site
    (B) LOCATION: 65
    (D) OTHER INFORMATION: /note= "Xaa at position 65 is Lys,
        Asn, Met, Arg, Ile, or Gly"

(ix) FEATURE:
    (A) NAME/KEY: Modified-site
    (B) LOCATION: 66
    (D) OTHER INFORMATION: /note= "Xaa at position 66 is Asn,
        Gly, Glu, or Arg"
```

```
(ix) FEATURE:
    (A) NAME/KEY: Modified-site
    (B) LOCATION: 68
    (D) OTHER INFORMATION: /note= "Xaa at position 68 is Leu,
        Gln, Trp, Arg, Asp, Asn, Glu, His, Met, Phe, Ser,
        Thr, Tyr, or Val"

(ix) FEATURE:
    (A) NAME/KEY: Modified-site
    (B) LOCATION: 73
    (D) OTHER INFORMATION: /note= "Xaa at position 73 is Leu
        or Ser"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
    (A) NAME/KEY: Modified-site
    (B) LOCATION: 79
    (D) OTHER INFORMATION: /note= "Xaa at position 79 is Thr,
        Asp, or Ala"

(ix) FEATURE:
    (A) NAME/KEY: Modified-site
    (B) LOCATION: 81
    (D) OTHER INFORMATION: /note= "Xaa at position 81 is His,
        Pro, Arg, Val, Gly, Asn, Ser, or Thr"

(ix) FEATURE:
    (A) NAME/KEY: Modified-site
    (B) LOCATION: 84
    (D) OTHER INFORMATION: /note= "Xaa at position 84 is His,
        Ile, Asn, Ala, Thr, Arg, Gln, Glu, Lys, Met,
        Ser, Tyr, Val, or Leu"

(ix) FEATURE:
    (A) NAME/KEY: Modified-site
    (B) LOCATION: 85
    (D) OTHER INFORMATION: /note= "Xaa at position 85 is Ile
        or Leu"

(ix) FEATURE:
    (A) NAME/KEY: Modified-site
    (B) LOCATION: 86
    (D) OTHER INFORMATION: /note= "Xaa at position 86 is Lys
        or Arg"

(ix) FEATURE:
    (A) NAME/KEY: Modified-site
    (B) LOCATION: 87
    (D) OTHER INFORMATION: /note= "Xaa at position 87 is Asp,
        Pro, Met, Lys, His, Pro, Asn, Ile, Leu, or Tyr"

(ix) FEATURE:
    (A) NAME/KEY: Modified-site
    (B) LOCATION: 91
    (D) OTHER INFORMATION: /note= "Xaa at position 91 is Asn,
        Pro, Ser, Ile, or Asp"

(ix) FEATURE:
    (A) NAME/KEY: Modified-site
    (B) LOCATION: 94
    (D) OTHER INFORMATION: /note="Xaa at position 94 is Arg,
        Ala, or Ser"

(ix) FEATURE:
    (A) NAME/KEY: Modified-site
    (B) LOCATION: 95
    (D) OTHER INFORMATION: /note= "Xaa at position 95 is Arg,
        Thr, Glu, Leu, or Ser"
```

```
    (ix) FEATURE:
         (A) NAME/KEY: Modified-site
         (B) LOCATION: 98
         (D) OTHER INFORMATION: /note= "Xaa at position 98 is Thr
             or Gln"

(ix) FEATURE:
         (A) NAME/KEY: Modified-site
         (B) LOCATION: 102
         (D) OTHER INFORMATION: /note= "Xaa at position 102 is Lys,
             Val, Trp, or Ile"

(ix) FEATURE:
         (A) NAME/KEY: Modified-site
         (B) LOCATION: 103
         (D) OTHER INFORMATION: /note= "Xaa at position 103 is Thr,
             Ala, His, Phe, Tyr, or Ser"

(ix) FEATURE:
         (A) NAME/KEY: Modified-site
         (B) LOCATION: 106
         (D) OTHER INFORMATION: /note= "Xaa at position 106 is Asn,
             Pro, Leu, His, Val, or Gln"

(ix) FEATURE:
         (A) NAME/KEY: Modified-site
         (B) LOCATION: 107
         (D) OTHER INFORMATION: /note= "Xaa at position 107 is Ala,
             Ser, Ile, Pro, or Asp"

(ix) FEATURE:
         (A) NAME/KEY: Modified-site
         (B) LOCATION: 108
         (D) OTHER INFORMATION: /note= "Xaa at position 108 is Gln,
             Met, Trp, Phe, Pro, His, Ile, or Tyr"

(ix) FEATURE:
         (A) NAME/KEY: Modified-site
         (B) LOCATION: 109
         (D) OTHER INFORMATION: /note= "Xaa at position 109 is Ala,
             Met, Glu, Ser, or Leu"

(xi) SEQUENCE DESCRIPTION: SEQ ID NO:6:

Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
                20                  25                  30

Ile Leu Met Xaa Xaa Asn Leu Arg Xaa Xaa Asn Leu Glu Ala Phe Xaa
            35                  40                  45

Arg Xaa Xaa Lys Xaa Xaa Xaa Asn Ala Ser Ala Ile Glu Xaa Xaa Leu
    50                  55                  60

Xaa Xaa Leu Xaa Pro Cys Leu Pro Xaa Xaa Thr Ala Xaa Pro Xaa Arg
65                  70                  75                  80

Xaa Pro Ile Xaa Xaa Xaa Xaa Gly Asp Trp Xaa Glu Phe Xaa Xaa Lys
                85                  90                  95

Leu Xaa Phe Tyr Leu Xaa Xaa Leu Glu Xaa Xaa Xaa Xaa Gln Gln
                100                 105                 110

(2) INFORMATION FOR SEQ ID NO:7:

(i) SEQUENCE CHARACTERISTICS:
         (A) LENGTH: 133 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1
```

(D) OTHER INFORMATION: /note= "Met- may or may not precede
                   the amino acid in position 1"

(ix) FEATURE:
               (A) NAME/KEY: Modified-site
               (B) LOCATION: 18
               (D) OTHER INFORMATION: /note= "Xaa at position 18 is Asn
                   or Ile"

(ix) FEATURE:
               (A) NAME/KEY: Modified-site
               (B) LOCATION: 19
               (D) OTHER INFORMATION: /note= "Xaa at position 19 is Met,
                   Ala, or Ile"

(ix) FEATURE:
               (A) NAME/KEY: Modified-site
               (B) LOCATION: 20
               (D) OTHER INFORMATION: /note= "Xaa at position 20 is Ile,
                   Pro, or Leu"

(ix) FEATURE:
               (A) NAME/KEY: Modified-site
               (B) LOCATION: 23
               (D) OTHER INFORMATION: /note= "Xaa at position 23 is Ile,
                   Ala, or Leu"

(ix) FEATURE:
               (A) NAME/KEY: Modified-site
               (B) LOCATION: 25
               (D) OTHER INFORMATION: /note= "Xaa at position 25 is Thr
                   or His"

(ix) FEATURE:
               (A) NAME/KEY: Modified-site
               (B) LOCATION: 29
               (D) OTHER INFORMATION: /note= "Xaa at position 29 is Gln,
                   Arg, Val, or Ile"

(ix) FEATURE:
               (A) NAME/KEY: Modified-site
               (B) LOCATION: 32
               (D) OTHER INFORMATION: /note= "Xaa at position 32 is Leu,
                   Ala, Asn, or Arg"

(ix) FEATURE:
               (A) NAME/KEY: Modified-site
               (B) LOCATION: 34
               (D) OTHER INFORMATION: /note= "Xaa at position 34 is Leu
                   or Ser"

(ix) FEATURE:
               (A) NAME/KEY: Modified-site
               (B) LOCATION: 37
               (D) OTHER INFORMATION: /note= "Xaa at position 37 is Phe,
                   Pro, or Ser"

(ix) FEATURE:
               (A) NAME/KEY: Modified-site
               (B) LOCATION:; 38
               (D) OTHER INFORMATION: /note= "Xaa at position 38 is Asn
                   or Ala"

(ix) FEATURE:
               (A) NAME/KEY: Modified-site
               (B) LOCATION: 42
               (D) OTHER INFORMATION: /note= "Xaa at position 42 is Gly,
                   Ala, Ser, Asp, or Asn"

(ix) FEATURE:
               (A) NAME/KEY: Modified-site
               (B) LOCATION: 45
               (D) OTHER INFORMATION: /note= "Xaa at position 45 is Gln,
                   Val, or Met"

(ix) FEATURE:
               (A) NAME/KEY: Modified-site
               (B) LOCATION: 46
               (D) OTHER INFORMATION: /note= "Xaa at position 46 is Asp

```
                       or Ser"

(ix) FEATURE:
    (A) NAME/KEY: Modified-site
    (B) LOCATION: 49
    (D) OTHER INFORMATION: /note= "Xaa at position 49 is Met,
        Ile, Leu, or Asp"

(ix) FEATURE:
    (A) NAME/KEY: Modified-site
    (B) LOCATION: 50
    (D) OTHER INFORMATION: /note= "Xaa at position 50 is Glu
        or Asp"

(ix) FEATURE:
    (A) NAME/KEY: Modified-site
    (B) LOCATION: 51
    (D) OTHER INFORMATION: /note= "Xaa at position 51 is Asn,
        Arg, or Ser"

(ix) FEATURE:
    (A) NAME/KEY: Modified-site
    (B) LOCATION: 55
    (D) OTHER INFORMATION: /note= "Xaa at position 55 is Arg,
        Leu, or Thr"

(ix) FEATURE:
    (A) NAME/KEY: Modified-site
    (B) LOCATION: 56
    (D) OTHER INFORMATION: /note= "Xaa at position 56 is Pro
        or Ser"

(ix) FEATURE:
    (A) NAME/KEY: Modified-site
    (B) LOCATION: 59
    (D) OTHER INFORMATION: /note= "Xaa at position 59 is Glu
        or Leu"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn
        Val, or Pro"

(ix) FEATURE:
    (A) NAME/KEY: Modified-site
    (B) LOCATION: 63
    (D) OTHER INFORMATION: /note= "Xaa at position 63 is Arg
        or His"

(ix) FEATURE:
    (A) NAME/KEY: Modified-site
    (B) LOCATION: 65
    (D) OTHER INFORMATION: /note= "Xaa at position 65 is Val
        or Ser"

(ix) FEATURE:
    (A) NAME/KEY: Modified-site
    (B) LOCATION: 67
    (D) OTHER INFORMATION: /note= "Xaa at position 67 is Ser,
        Asn, His, or Gln"

(ix) FEATURE:
    (A) NAME/KEY: Modified-site
    (B) LOCATION: 69
    (D) OTHER INFORMATION: /note= "Xaa at position 69 is Gln
        or Glu"

(ix) FEATURE:
    (A) NAME/KEY: Modified-site
    (B) LOCATION: 73
    (D) OTHER INFORMATION: /note= "Xaa at position 73 is Ala
        or Gly"
```

```
(ix) FEATURE:
    (A) NAME/KEY: Modified-site
    (B) LOCATION: 76
    (D) OTHER INFORMATION: /note= "Xaa at position 76 is Ser,
        Ala, or Pro"

(ix) FEATURE:
    (A) NAME/KEY: Modified-site
    (B) LOCATION: 79
    (D) OTHER INFORMATION: /note= "Xaa at position 79 is Lys,
        Arg, or Ser"

(ix) FEATURE:
    (A) NAME/KEY: Modified-site
    (B) LOCATION: 82
    (D) OTHER INFORMATION: /note= "Xaa at position 82 is Leu,
        Glu, Val, or Trp"

(ix) FEATURE:
    (A) NAME/KEY: Modified-site
    (B) LOCATION: 85
    (D) OTHER INFORMATION: /note= "Xaa at position 85 is Leu
        or Val"

(ix) FEATURE:
    (A) NAME/KEY: Modified-site
    (B) LOCATION: 87
    (D) OTHER INFORMATION: /note= "Xaa at position 87 is Leu,
        Ser, or Tyr"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Pro
        or Ser"

(ix) FEATURE:
    (A) NAME/KEY: Modified-site
    (B) LOCATION: 95
    (D) OTHER INFORMATION: /note= "Xaa at position 95 is His
        or Thr"

(ix) FEATURE:
    (A) NAME/KEY: Modified-site
    (B) LOCATION: 98
    (D) OTHER INFORMATION: /note= "Xaa at position 98 is His,
        Ile, or Thr"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Ala, or Met"

(ix) FEATURE:
    (A) NAME/KEY: Modified-site
    (B) LOCATION: 105
    (D) OTHER INFORMATION: /note= "Xaa at position 105 is Asn
        or Glu"
```

(ix) FEATURE:
            (A) NAME/KEY: Modified-site
            (B) LOCATION: 109
            (D) OTHER INFORMATION: /note= "Xaa at position 109 is Arg,
                Glu, or Leu"

(ix) FEATURE:
            (A) NAME/KEY: Modified-site
            (B) LOCATION: 112
            (D) OTHER INFORMATION: /note= "Xaa at position 112 is Thr
                or Gln"

(ix) FEATURE:
            (A) NAME/KEY: Modified-site
            (B) LOCATION: 116
            (D) OTHER INFORMATION: /note= "Xaa at position 116 is Lys,
                Val, Trp, or Ser"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Gln, or His"

(ix) FEATURE:
            (A) NAME/KEY: Modified-site
            (B) LOCATION: 123
            (D) OTHER INFORMATION: /note= "Xaa at position 123 is Ala
                or Glu"

(xi) SEQUENCE DESCRIPTION: SEQ ID NO:7:

Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
50                  55                  60

Xaa Lys Xaa Leu Xaa Asn Ala Ser Xaa Ile Glu Xaa Ile Leu Xaa Asn
65                  70                  75                  80

Leu Xaa Pro Cys Xaa Pro Xaa Xaa Thr Ala Xaa Pro Xaa Arg Xaa Pro
        85                  90                  95

Ile Xaa Ile Xaa Xaa Gly Asp Trp Xaa Glu Phe Arg Xaa Lys Leu Xaa
        100                 105                 110

Phe Tyr Leu Xaa Xaa Leu Glu Xaa Ala Gln Xaa Gln Gln Thr Thr Leu
        115                 120                 125

Ser Leu Ala Ile Phe
        130

(2) INFORMATION FOR SEQ ID NO:8:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala may or may

```
            not precede the amino acid in position 1"

(ix) FEATURE:
      (A) NAME/KEY: Modified-site
      (B) LOCATION: 4
      (D) OTHER INFORMATION: /note= "Xaa at position 4 is Asn or
          Ile"

(ix) FEATURE:
      (A) NAME/KEY: Modified-site
      (B) LOCATION: 5
      (D) OTHER INFORMATION: /note= "Xaa at position 5 is Met,
          Ala, or Ile"

(ix) FEATURE:
      (A) NAME/KEY: Modified-site
      (B) LOCATION: 6
      (D) OTHER INFORMATION: /note= "Xaa at position 6 is Ile,
          Pro, or Leu"

(ix) FEATURE:
      (A) NAME/KEY: Modified-site
      (B) LOCATION: 9
      (D) OTHER INFORMATION: /note= "Xaa at position 9 is Ile,
          Ala, or Leu"

(ix) FEATURE:
      (A) NAME/KEY: Modified-site
      (B) LOCATION: 11
      (D) OTHER INFORMATION: /note= "Xaa at position 11 is Thr
          or His"

(ix) FEATURE:
      (A) NAME/KEY: Modified-site
      (B) LOCATION: 15
      (D) OTHER INFORMATION: /note= "Xaa at position 15 is Gln,
          Arg, Val, or Ile"

(ix) FEATURE:
      (A) NAME/KEY: Modified-site
      (B) LOCATION: 18
      (D) OTHER INFORMATION: /note= "Xaa at position 18 is Leu,
          Ala, Asn, or Arg"

(ix) FEATURE:
      (A) NAME/KEY: Modified-site
      (B) LOCATION: 20
      (D) OTHER INFORMATION: /note= "Xaa at position 20 is Leu
          or Ser"

(ix) FEATURE:
      (A) NAME/KEY: Modified-site
      (B) LOCATION: 23
      (D) OTHER INFORMATION: /note= "Xaa at position 23 is Phe,
          Pro, or Ser"

(ix) FEATURE:
      (A) NAME/KEY: Modified-site
      (B) LOCATION: 24
      (D) OTHER INFORMATION: /note= "Xaa at position 24 is Asn
          or Ala"

(ix) FEATURE:
      (A) NAME/KEY: Modified-site
      (B) LOCATION: 28
      (D) OTHER INFORMATION: /note= "Xaa at position 28 is Gly,
          Ala, Ser, Asp, or Asn"

(ix) FEATURE:
      (A) NAME/KEY: Modified-site
      (B) LOCATION: 31
      (D) OTHER INFORMATION: /note= "Xaa at position 31 is Gln,
          Val, or Met"

(ix) FEATURE:
      (A) NAME/KEY: Modified-site
      (B) LOCATION: 32
      (D) OTHER INFORMATION: /note= "Xaa at position 32 is Asp
          or Ser"
```

-continued

```
(ix) FEATURE:
     (A) NAME/KEY: Modified-site
     (B) LOCATION: 35
     (D) OTHER INFORMATION: /note= "Xaa at position 35 is Met,
         Ile, or Asp"

(ix) FEATURE:
     (A) NAME/KEY: Modified-site
     (B) LOCATION: 36
     (D) OTHER INFORMATION: /note= "Xaa at position 36 is Glu
         or Asp"

(ix) FEATURE:
     (A) NAME/KEY: Modified-site
     (B) LOCATION: 37
     (D) OTHER INFORMATION: /note= "Xaa at position 37 is Asn,
         Arg, or Ser"

(ix) FEATURE:
     (A) NAME/KEY: Modified-site
     (B) LOCATION: 41
     (D) OTHER INFORMATION: /note= "Xaa at position 41 is Arg,
         Leu, or Thr"

(ix) FEATURE:
     (A) NAME/KEY: Modified-site
     (B) LOCATION: 42
     (D) OTHER INFORMATION: /note= "Xaa at position 42 is Pro
         or Ser"

(ix) FEATURE:
     (A) NAME/KEY: Modified-site
     (B) LOCATION: 45
     (D) OTHER INFORMATION: /note= "Xaa at position 45 is Glu
         or Leu"

(ix) FEATURE:
     (A) NAME/KEY: Modified-site
     (B) LOCATION: 46
     (D) OTHER INFORMATION: /note= "Xaa at position 46 is Ala
         or Ser"

(ix) FEATURE:
     (A) NAME/KEY: Modified-site
     (B) LOCATION: 48
     (D) OTHER INFORMATION: /note= "Xaa at position 48 is Asn,
         Val, or Pro"

(ix) FEATURE:
     (A) NAME/KEY: Modified-site
     (B) LOCATION: 49
     (D) OTHER INFORMATION: /note= "Xaa at position 49 is Arg
         or His"

(ix) FEATURE:
     (A) NAME/KEY: Modified-site
     (B) LOCATION: 51
     (D) OTHER INFORMATION: /note= "Xaa at position 51 is Val
         or Ser"

(ix) FEATURE:
     (A) NAME/KEY: Modified-site
     (B) LOCATION: 53
     (D) OTHER INFORMATION: /note= "Xaa at position 53 is Ser,
         Asn, His, or Gln"

(ix) FEATURE:
     (A) NAME/KEY: Modified-site
     (B) LOCATION: 55
     (D) OTHER INFORMATION: /note= "Xaa at position 55 is Gln
         or Glu"

(ix) FEATURE:
     (A) NAME/KEY: Modified-site
     (B) LOCATION: 59
     (D) OTHER INFORMATION: /note= "Xaa at position 59 is Ala
         or Gly"
```

```
(ix) FEATURE:
    (A) NAME/KEY: Modified-site
    (B) LOCATION: 62
    (D) OTHER INFORMATION: /note= "Xaa at position 62 is Ser,
         Ala, or Pro"

(ix) FEATURE:
    (A) NAME/KEY: Modified-site
    (B) LOCATION: 65
    (D) OTHER INFORMATION: /note= "Xaa at position 65 is Lys,
         Arg, or Ser"

(ix) FEATURE:
    (A) NAME/KEY: Modified-site
    (B) LOCATION: 67
    (D) OTHER INFORMATION: /note= "Xaa at position 67 is Leu,
         Glu, or Val"

(ix) FEATURE:
    (A) NAME/KEY: Modified-site
    (B) LOCATION: 68
    (D) OTHER INFORMATION: /note= "Xaa at position 68 is Leu,
         Glu, Val, or Trp"

(ix) FEATURE:
    (A) NAME/KEY: Modified-site
    (B) LOCATION: 71
    (D) OTHER INFORMATION: /note= "Xaa at position 71 is Leu
         or Val"

(ix) FEATURE:
    (A) NAME/KEY: Modified-site
    (B) LOCATION: 73
    (D) OTHER INFORMATION: /note= "Xaa at position 73 is Leu,
         Ser, or Tyr"

(ix) FEATURE:
    (A) NAME/KEY: Modified-site
    (B) LOCATION: 74
    (D) OTHER INFORMATION: /note= "Xaa at position 74 is Ala
         or Trp"

(ix) FEATURE:
    (A) NAME/KEY: Modified-site
    (B) LOCATION: 77
    (D) OTHER INFORMATION: /note= "Xaa at position 77 is Ala
         or Pro"

(ix) FEATURE:
    (A) NAME/KEY: Modified-site
    (B) LOCATION: 79
    (D) OTHER INFORMATION: /note= "Xaa at position 79 is Pro
         or Ser"

(ix) FEATURE:
    (A) NAME/KEY: Modified-site
    (B) LOCATION: 81
    (D) OTHER INFORMATION: /note= "Xaa at position 81 is His
         or Thr"

(ix) FEATURE:
    (A) NAME/KEY: Modified-site
    (B) LOCATION: 84
    (D) OTHER INFORMATION: /note= "Xaa at position 84 is His,
         Ile, or Thr"

(ix) FEATURE:
    (A) NAME/KEY: Modified-site
    (B) LOCATION: 86
    (D) OTHER INFORMATION: /note= "Xaa at position 86 is Lys
         or Arg"

(ix) FEATURE:
    (A) NAME/KEY: Modified-site
    (B) LOCATION: 87
    (D) OTHER INFORMATION: /note= "Xaa at position 87 is Asp,
         Ala, or Met"

(ix) FEATURE:
```

(A) NAME/KEY: Modified-site
        (B) LOCATION: 91
        (D) OTHER INFORMATION: /note= "Xaa at position 91 is Asn
            or Glu"

(ix) FEATURE:
        (A) NAME/KEY: Modified-site
        (B) LOCATION: 95
        (D) OTHER INFORMATION: /note= "Xaa at position 95 is Arg,
            Glu, or Leu"

(ix) FEATURE:
        (A) NAME/KEY: Modified-site
        (B) LOCATION: 98
        (D) OTHER INFORMATION: /note= "Xaa at position 98 is Thr
            or Gln"

(ix) FEATURE:
        (A) NAME/KEY: Modified-site
        (B) LOCATION: 102
        (D) OTHER INFORMATION: /note= "Xaa at position 102 is Lys,
            Val, Trp, or Ser"

(ix) FEATURE:
        (A) NAME/KEY: Modified-site
        (B) LOCATION: 103
        (D) OTHER INFORMATION: /note= "Xaa at position 103 is Thr
            or Ser"

(ix) FEATURE:
        (A) NAME/KEY: Modified-site
        (B) LOCATION: 106
        (D) OTHER INFORMATION: /note= "Xaa at position 106 is Asn,
            Gln, or His"

(ix) FEATURE:
        (A) NAME/KEY: Modified-site
        (B) LOCATION: 109
        (D) OTHER INFORMATION: /note= "Xaa at position 109 is Ala
            or Glu"

(xi) SEQUENCE DESCRIPTION: SEQ ID NO:8:

Asn Cys Ser Xaa Xaa Xaa Asp Glu Xaa Ile Xaa His Leu Lys Xaa Pro
1               5                   10                  15

Pro Xaa Pro Xaa Leu Asp Xaa Xaa Asn Leu Asn Xaa Glu Asp Xaa Xaa
            20                  25                  30

Ile Leu Xaa Xaa Xaa Asn Leu Arg Xaa Xaa Asn Leu Xaa Xaa Phe Xaa
        35                  40                  45

Xaa Ala Xaa Lys Xaa Leu Xaa Asn Ala Ser Xaa Ile Glu Xaa Ile Leu
50                  55                  60

Xaa Asn Xaa Xaa Pro Cys Xaa Pro Xaa Xaa Thr Ala Xaa Pro Xaa Arg
65                  70                  75                  80

Xaa Pro Ile Xaa Ile Xaa Xaa Gly Asp Trp Xaa Glu Phe Arg Xaa Lys
            85                  90                  95

Leu Xaa Phe Tyr Leu Xaa Xaa Leu Glu Xaa Ala Gln Xaa Gln Gln
            100                 105                 110

(2) INFORMATION FOR SEQ ID NO:9:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:9:

Asn Cys Ser Ile Met Ile Asp Glu Ile Ile His His Leu Lys Arg Pro
1               5                   10                  15

```
Pro Ala Pro Leu Leu Asp Pro Asn Asn Leu Asn Ala Glu Asp Val Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:10:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:10:

```
Asn Cys Ser Ile Met Ile Asp Glu Ile Ile His His Leu Lys Arg Pro
 1               5                  10                  15

Pro Asn Pro Leu Leu Asp Pro Asn Asn Leu Asn Ser Glu Asp Met Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:11:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:11:

```
Asn Cys Ser Ile Met Ile Asp Glu Ile Ile His His Leu Lys Val Pro
 1               5                  10                  15

Pro Ala Pro Leu Leu Asp Ser Asn Asn Leu Asn Ser Glu Asp Met Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
```

```
                      85                  90                  95
Leu Thr Phe Tyr Leu Lys Thr Leu Glu Asn Ala Gln Ala Gln Gln
                    100                 105                 110

(2) INFORMATION FOR SEQ ID NO:12:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:12:

Asn Cys Ser Asn Met Ile Asp Glu Ile Ile Thr His Leu Lys Gln Pro
1               5                  10                  15

Pro Leu Pro Leu Leu Asp Phe Asn Asn Leu Asn Gly Glu Asp Gln Asp
                20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:13:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:13:

Asn Cys Ser Asn Met Ile Asp Glu Ile Ile Thr His Leu Lys Gln Pro
1               5                  10                  15

Pro Leu Pro Leu Leu Asp Phe Asn Asn Leu Asn Gly Glu Asp Gln Asp
                20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:14:

(i) SEQUENCE CHARACTERISTICS:
        (A) LENGTH: 111 amino acids
        (B) TYPE: amino acid
        (D) TOPOLOGY: linear
```

(ii) MOLECULE TYPE: peptide (xi) SEQUENCE DESCRIPTION: SEQ ID NO:14:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:15:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
        50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:16:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:16:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45
```

Arg Ala Val Lys Ser Leu Gln Asn Ala Ser Gly Ile Glu Ala Ile Leu
 50              55              60

Arg Asn Leu Val Pro Cys Leu Pro Ser Ala Thr Ala Ala Pro Ser Arg
 65              70              75              80

His Pro Ile Thr Ile Lys Ala Gly Asp Trp Gln Glu Phe Arg Arg Lys
                 85              90              95

Leu Thr Phe Tyr Leu Lys Thr Leu Glu Asn Ala Gln Ala Gln Gln
                100             105             110

(2) INFORMATION FOR SEQ ID NO:17:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:17:

Asn Cys Ser Asn Met Ile Asp Glu Ile Ile Thr His Leu Lys Gln Pro
 1               5               10              15

Pro Leu Pro Leu Leu Asp Phe Asn Asn Leu Asn Gly Glu Asp Gln Asp
                 20              25              30

Ile Leu Met Glu Asn Asn Leu Arg Arg Pro Asn Leu Glu Ala Phe Asn
                 35              40              45

Arg Ala Val Lys Ser Leu Gln Asn Ala Ser Ala Ile Glu Ser Ile Leu
 50              55              60

Lys Asn Leu Leu Pro Cys Leu Pro Leu Ala Thr Ala Ala Pro Thr Arg
 65              70              75              80

His Pro Ile His Ile Lys Asp Gly Asp Trp Asn Glu Phe Arg Glu Lys
                 85              90              95

Leu Thr Phe Tyr Leu Val Thr Leu Glu Gln Ala Gln Glu Gln Gln
                100             105             110

(2) INFORMATION FOR SEQ ID NO:18:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:18:

Asn Cys Ser Asn Met Ile Asp Glu Ile Ile Thr His Leu Lys Gln Pro
 1               5               10              15

Pro Leu Pro Leu Leu Asp Phe Asn Asn Leu Asn Gly Glu Asp Gln Asp
                 20              25              30

Ile Leu Met Glu Asn Asn Leu Arg Arg Pro Asn Leu Glu Ala Phe Asn
                 35              40              45

Arg Ala Val Lys Ser Leu Gln Asn Ala Ser Ala Ile Glu Ser Ile Leu
 50              55              60

Lys Asn Leu Leu Pro Cys Leu Pro Leu Ala Thr Ala Ala Pro Thr Arg
 65              70              75              80

His Pro Ile His Ile Lys Asp Gly Asp Trp Asn Glu Phe Arg Glu Lys
                 85              90              95

Leu Thr Phe Tyr Leu Val Ser Leu Glu His Ala Gln Glu Gln Gln
                100             105             110

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:19:

```
Asn Cys Ser Asn Met Ile Asp Glu Ile Ile Thr His Leu Lys Gln Pro
 1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
            50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:20:

```
Asn Cys Ser Asn Met Ile Asp Glu Ile Ile Thr His Leu Lys Gln Pro
 1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
            50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:21:

```
Asn Cys Ser Asn Met Ile Asp Glu Ile Ile Thr His Leu Lys Gln Pro
 1               5                   10                  15
```

```
Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
 50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Glu Lys
                 85                  90                  95

Leu Thr Phe Tyr Leu Val Ser Leu Glu His Ala Gln Glu Gln Gln
                100                 105                 110

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:22:

Asn Cys Ser Ile Met Ile Asp Glu Ile Ile His His Leu Lys Arg Pro
 1                   5                  10                  15

Pro Ala Pro Leu Leu Asp Pro Asn Asn Leu Asn Ala Glu Asp Val Asp
            20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110

(2) INFORMATION FOR SEQ ID NO:23:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:23:

Asn Cys Ser Ile Met Ile Asp Glu Ile Ile His His Leu Lys Arg Pro
 1                   5                  10                  15

Pro Asn Pro Leu Leu Asp Pro Ser Asn Leu Asn Ser Glu Asp Met Asp
            20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80
```

```
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
            100                 105                 110

(2) INFORMATION FOR SEQ ID NO:24:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:24:

Asn Cys Ser Ile Met Ile Asp Glu Ile Ile His His Leu Lys Val Pro
1               5                   10                  15
Pro Ala Pro Leu Leu Asp Ser Asn Asn Leu Asn Ser Glu Asp Met Asp
            20                  25                  30
Ile Leu Met Glu Arg Asn Leu Arg Leu Pro Asn Leu Leu Ala Phe Val
            35                  40                  45
Arg Ala Val Lys Asn Leu Glu Asn Ala Ser Ala Ile Glu Ser Ile Leu
50                  55                  60
Lys Asn Leu Leu Pro Cys Leu Pro Leu Ala Thr Ala Ala Pro Thr Arg
65                  70                  75                  80
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
            100                 105                 110

(2) INFORMATION FOR SEQ ID NO:25:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:25:

Met Ala Asn Cys Ser Asn Met Ile Asp Glu Ile Ile Thr His Leu Lys
1               5                   10                  15
Gln Pro Pro Leu Pro Leu Leu Asp Phe Asn Asn Leu Asn Gly Glu Asp
            20                  25                  30
Gln Asp Ile Leu Met Glu Asn Asn Leu Arg Arg Pro Asn Leu Glu Ala
            35                  40                  45
Phe Asn Arg Ala Val Lys Ser Leu Gln Asn Ala Ser Gly Ile Glu Ala
50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln (2) INFORMATION FOR SEQ ID NO:26:

(i) SEQUENCE CHARACTERISTICS:
        (A) LENGTH: 113 amino acids
```

(B) TYPE: amino acid
        (D) TOPOLOGY: linear (ii) MOLECULE TYPE: peptide (xi) SEQUENCE DESCRIPTION: SEQ ID NO:26:

Met Ala Asn Cys Ser Asn Met Ile Asp Glu Ile Ile Thr His Leu Lys
1               5                   10                  15

Gln Pro Pro Leu Pro Leu Asp Phe Asn Asn Leu Asn Gly Glu Asp
            20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
50                      55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:27:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:27:

Met Ala Asn Cys Ser Asn Met Ile Asp Glu Ile Ile Thr His Leu Lys
1               5                   10                  15

Gln Pro Pro Leu Pro Leu Asp Phe Asn Asn Leu Asn Gly Glu Asp
            20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
50                      55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln (2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:28:

Met Ala Asn Cys Ser Ile Met Ile Asp Glu Ile Ile His His Leu Lys
1               5                   10                  15

```
Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Ala Ile Glu Ser
            50                  55                  60

Ile Leu Lys Asn Leu Leu Pro Cys Leu Pro Leu Ala Thr Ala Ala Pro
65                      70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:29:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:29:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Ala Ile Glu Ser
            50                  55                  60

Ile Leu Lys Asn Leu Leu Pro Cys Leu Pro Leu Ala Thr Ala Ala Pro
65                      70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:30:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:30:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Ala Ile Glu Ser
            50                  55                  60
```

```
Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
               100                 105                 110

Gln
```

(2) INFORMATION FOR SEQ ID NO:31:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:31:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
               35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:32:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:32:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
               35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110
```

Gln (2) INFORMATION FOR SEQ ID NO:33:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:33:

```
Met Ala Asn Cys Ser Ile Met Ile Asp Glu Ile Ile His His Leu Lys
 1               5                  10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:34:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:34:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:35:

(i) SEQUENCE CHARACTERISTICS:
        (A) LENGTH: 113 amino acids
        (B) TYPE: amino acid (D) TOPOLOGY: linear (ii) MOLECULE TYPE: peptide (xi) SEQUENCE DESCRIPTION: SEQ ID NO:35:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:36:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:36:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln (2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:37:

Met Ala Asn Cys Ser Ile Met Ile Asp Glu Ile Ile His His Leu Lys
1               5                   10                  15

```
Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
            50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:38:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:38:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
            50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:39:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:39:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
            50                  55                  60
```

```
Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:40:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:40:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
                 20                  25                  30

Val Asp Ile Leu Met Asp Arg Asn Leu Arg Leu Ser Asn Leu Glu Ser
                 35                  40                  45

Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:41:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:41:

```
Met Ala Asn Cys Ser Ile Met Ile Asp Glu Ala Ile His His Leu Lys
 1               5                  10                  15

Arg Pro Pro Ala Pro Ser Leu Asp Pro Asn Asn Leu Asn Asp Glu Asp
                 20                  25                  30

Met Ser Ile Leu Met Glu Arg Asn Leu Arg Leu Pro Asn Leu Glu Ser
                 35                  40                  45

Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110
```

Gln (2) INFORMATION FOR SEQ ID NO:42:

(i) SEQUENCE CHARACTERISTICS:
  (A) LENGTH: 113 amino acids
  (B) TYPE: amino acid
  (D) TOPOLOGY: linear (ii) MOLECULE TYPE: peptide (xi) SEQUENCE DESCRIPTION: SEQ ID NO:42:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Met Ser Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:43:

(i) SEQUENCE CHARACTERISTICS:
  (A) LENGTH: 113 amino acids
  (B) TYPE: amino acid
  (D) TOPOLOGY: linear (ii) MOLECULE TYPE: peptide (xi) SEQUENCE DESCRIPTION: SEQ ID NO:43:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:44:

(i) SEQUENCE CHARACTERISTICS:
  (A) LENGTH: 113 amino acids
  (B) TYPE: amino acid
  (D) TOPOLOGY: linear (ii) MOLECULE TYPE: peptide (xi) SEQUENCE DESCRIPTION: SEQ ID NO:44:

```
Met Ala Asn Cys Ser Ile Met Ile Asp Glu Ile Ile His His Leu Lys
  1               5                  10                  15
Arg Pro Pro Ala Pro Leu Leu Asp Pro Asn Asn Leu Asn Asp Glu Asp
                 20                  25                  30
Val Ser Ile Leu Met Glu Arg Asn Leu Arg Leu Pro Asn Leu Glu Ser
             35                  40                  45
Phe Val Arg Ala Val Lys Asn Leu Glu Asn Ala Ser Gly Ile Glu Ala
 50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:45:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:45:

```
Met Ala Asn Cys Ser Ile Met Ile Asp Glu Ile Ile His His Leu Lys
  1               5                  10                  15
Arg Pro Pro Ala Pro Leu Leu Asp Pro Asn Asn Leu Asn Asp Glu Asp
                 20                  25                  30
Met Ser Ile Leu Met Glu Arg Asn Leu Arg Leu Pro Asn Leu Glu Ser
             35                  40                  45
Phe Val Arg Ala Val Lys Asn Leu Glu Asn Ala Ser Gly Ile Glu Ala
 50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:46:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:46:

```
Met Ala Tyr Pro Glu Thr Asp Tyr Lys Asp Asp Asp Lys Asn Cys
  1               5                  10                  15
Ser Ile Met Ile Asp Glu Ile Ile His His Leu Lys Arg Pro Pro Ala
```

```
                    20                  25                  30

Pro Leu Leu Asp Pro Asn Asn Leu Asn Ala Glu Asp Val Asp Ile Leu
            35                  40                  45

Met Glu Arg Asn Leu Arg Leu Pro Asn Leu Glu Ser Phe Val Arg Ala
 50                  55                  60

Val Lys Asn Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
            115                 120                 125

(2) INFORMATION FOR SEQ ID NO:47:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:47:

Met Ala Tyr Pro Glu Thr Asp Tyr Lys Asp Asp Asp Lys Asn Cys
  1               5                  10                  15

Ser Ile Met Ile Asp Glu Ile Ile His Leu Lys Arg Pro Pro Asn
                20                  25                  30

Pro Leu Leu Asp Pro Asn Asn Leu Asn Ser Glu Asp Met Asp Ile Leu
            35                  40                  45

Met Glu Arg Asn Leu Arg Thr Pro Asn Leu Leu Ala Phe Val Arg Ala
 50                  55                  60

Val Lys His Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
            115                 120                 125

(2) INFORMATION FOR SEQ ID NO:48:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:48:

Met Ala Asn Cys Ser Ile Met Ile Asp Glu Leu Ile His His Leu Lys
  1               5                  10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
 50                  55                  60
```

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:49:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:49:

Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
                20                  25                  30

Leu Pro Leu Leu Asp Phe Asn Asn Leu Asn Gly Glu Asp Gln Asp Ile
            35                  40                  45

Leu Met Glu Asn Asn Leu Arg Arg Pro Asn Leu Glu Ala Phe Asn Arg
        50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
            100                 105                 110

Thr Phe Tyr Leu Lys Thr Leu Glu Asn Ala Gln Ala Gln Gln Thr Thr
        115                 120                 125

Leu Ser Leu Ala Ile Phe
    130

(2) INFORMATION FOR SEQ ID NO:50:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:50:

CATGGCAAGA TCTCCGGCCA GAATGGAGCT GACTGA                           36

(2) INFORMATION FOR SEQ ID NO:51:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:51:

AATAGCTGAA TTCTTACCCT TCCTGAGACA GATT                                    34

(2) INFORMATION FOR SEQ ID NO:52:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:52:

ACGTCCATGG CNTCNCCNGC NCCNCCTGCT TGTGACCTCC GAGTC                         45

(2) INFORMATION FOR SEQ ID NO:53:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:53:

TGACAAGCTT ACCTGACGCA GAGGGTGGAC CCT                                     33

(2) INFORMATION FOR SEQ ID NO:54:

(i) SEQUENCE CHARACTERISTICS:
          (A) LENGTH: 465 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:54:

ATGGCGTCTC CGGCGCCGCC TGCTTGTGAC CTCCGAGTCC TCAGTAAACT GCTTCGTGAC         60

TCCCATGTCC TTCACAGCAG ACTGAGCCAG TGCCCAGAGG TTCACCCTTT GCCTACACCT        120

GTCCTGCTGC CTGCTGTGGA CTTTAGCTTG GGAGAATGGA AAACCCAGAT GGAGGAGACC        180

AAGGCACAGG ACATTCTGGG AGCAGTGACC CTTCTGCTGG AGGGAGTGAT GGCAGCACGG        240

GGACAACTGG GACCCACTTG CCTCTCATCC CTCCTGGGGC AGCTTTCTGG ACAGGTCCGT        300

CTCCTCCTTG GGGCCCTGCA GAGCCTCCTT GGAACCCAGC TTCCTCCACA GGGCAGGACC        360

ACAGCTCACA AGGATCCCAA TGCCATCTTC CTGAGCTTCC AACACCTGCT CCGAGGAAAG        420

GTGCGTTTCC TGATGCTTGT AGGAGGGTCC ACCCTCTGCG TCAGG                        465

(2) INFORMATION FOR SEQ ID NO:55:

(i) SEQUENCE CHARACTERISTICS:
          (A) LENGTH: 353 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:55:

Met Glu Leu Thr Glu Leu Leu Leu Val Val Met Leu Leu Leu Thr Ala

```
1               5                    10                   15
Arg Leu Thr Leu Ser Ser Pro Ala Pro Ala Cys Asp Leu Arg Val
                20              25              30

Leu Ser Lys Leu Leu Arg Asp Ser His Val Leu His Ser Arg Leu Ser
        35              40              45

Gln Cys Pro Glu Val His Pro Leu Pro Thr Pro Val Leu Leu Pro Ala
    50              55              60

Val Asp Phe Ser Leu Gly Glu Trp Lys Thr Gln Met Glu Glu Thr Lys
65              70              75              80

Ala Gln Asp Ile Leu Gly Ala Val Thr Leu Leu Glu Gly Val Met
                85              90              95

Ala Ala Arg Gly Gln Leu Gly Pro Thr Cys Leu Ser Ser Leu Leu Gly
            100             105             110

Gln Leu Ser Gly Gln Val Arg Leu Leu Leu Gly Ala Leu Gln Ser Leu
        115             120             125

Leu Gly Thr Gln Leu Pro Pro Gln Gly Arg Thr Thr Ala His Lys Asp
    130             135             140

Pro Asn Ala Ile Phe Leu Ser Phe Gln His Leu Leu Arg Gly Lys Val
145             150             155             160

Arg Phe Leu Met Leu Val Gly Gly Ser Thr Leu Cys Val Arg Arg Ala
                165             170             175

Pro Pro Thr Thr Ala Val Pro Ser Arg Thr Ser Leu Val Leu Thr Leu
            180             185             190

Asn Glu Leu Pro Asn Arg Thr Ser Gly Leu Leu Glu Thr Asn Phe Thr
        195             200             205

Ala Ser Ala Arg Thr Thr Gly Ser Gly Leu Leu Lys Trp Gln Gln Gly
    210             215             220

Phe Arg Ala Lys Ile Pro Gly Leu Leu Asn Gln Thr Ser Arg Ser Leu
225             230             235             240

Asp Gln Ile Pro Gly Tyr Leu Asn Arg Ile His Glu Leu Leu Asn Gly
                245             250             255

Thr Arg Gly Leu Phe Pro Gly Pro Ser Arg Arg Thr Leu Gly Ala Pro
            260             265             270

Asp Ile Ser Ser Gly Thr Ser Asp Thr Gly Ser Leu Pro Pro Asn Leu
        275             280             285

Gln Pro Gly Tyr Ser Pro Ser Pro Thr His Pro Pro Thr Gly Gln Tyr
    290             295             300

Thr Leu Phe Pro Leu Pro Pro Thr Leu Pro Thr Pro Val Val Gln Leu
305             310             315             320

His Pro Leu Leu Pro Asp Pro Ser Ala Pro Thr Pro Thr Pro Thr Ser
                325             330             335

Pro Leu Leu Asn Thr Ser Tyr Thr His Ser Gln Asn Leu Ser Gln Glu
            340             345             350

Gly
```

(2) INFORMATION FOR SEQ ID NO:56:

(i) SEQUENCE CHARACTERISTICS:
        (A) LENGTH: 174 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:56:

```
Met Glu Leu Thr Glu Leu Leu Val Val Met Leu Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
            115                 120                 125

Leu Gly Thr Gln Leu Pro Pro Gln Gly Arg Thr Thr Ala His Lys Asp
        130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg
                165                 170
```

(2) INFORMATION FOR SEQ ID NO:57:

(i) SEQUENCE CHARACTERISTICS:
        (A) LENGTH: 1059 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

```
ATGGAGCTGA CTGAATTGCT CCTCGTGGTC ATGCTTCTCC TAACTGCAAG GCTAACGCTG    60

TCCAGCCCGG CTCCTCCTGC TTGTGACCTC CGAGTCCTCA GTAAACTGCT TCGTGACTCC   120

CATGTCCTTC ACAGCAGACT GAGCCAGTGC CCAGAGGTTC ACCCTTTGCC TACACCTGTC   180

CTGCTGCCTG CTGTGGACTT TAGCTTGGGA GAATGGAAAA CCCAGATGGA GGAGACCAAG   240

GCACAGGACA TTCTGGGAGC AGTGACCCTT CTGCTGGAGG GAGTGATGGC AGCACGGGGA   300

CAACTGGGAC CCACTTGCCT CTCATCCCTC CTGGGGCAGC TTTCTGGACA GGTCCGTCTC   360

CTCCTTGGGG CCCTGCAGAG CCTCCTTGGA ACCCAGCTTC CTCCACAGGG CAGGACCACA   420

GCTCACAAGG ATCCCAATGC CATCTTCCTG AGCTTCCAAC ACCTGCTCCG AGGAAAGGTG   480

CGTTTCCTGA TGCTTGTAGG AGGGTCCACC CTCTGCGTCA GGCGGGCCCC ACCCACCACA   540

GCTGTCCCCA GCAGAACCTC TCTAGTCCTC ACACTGAACG AGCTCCCAAA CAGGACTTCT   600

GGATTGTTGG AGACAAACTT CACTGCCTCA GCCAGAACTA CTGGCTCTGG GCTTCTGAAG   660

TGGCAGCAGG GATTCAGAGC CAAGATTCCT GGTCTGCTGA ACCAAACCTC CAGGTCCCTG   720

GACCAAATCC CCGGATACCT GAACAGGATA CACGAACTCT TGAATGGAAC TCGTGGACTC   780

TTTCCTGGAC CCTCACGCAG GACCCTAGGA GCCCCGGACA TTTCCTCAGG AACATCAGAC   840

ACAGGCTCCC TGCCACCCAA CCTCCAGCCT GGATATTCTC CTTCCCCAAC CCATCCTCCT   900

ACTGGACAGT ATACGCTCTT CCCTCTTCCA CCCACCTTGC CCACCCCTGT GGTCCAGCTC   960
```

```
CACCCCCTGC TTCCTGACCC TTCTGCTCCA ACGCCCACCC CTACCAGCCC TCTTCTAAAC    1020

ACATCCTACA CCCACTCCCA GAATCTGTCT CAGGAAGGG                            1059
```